US012697298B2

(12) United States Patent
Weiner et al.

(10) Patent No.: US 12,697,298 B2
(45) Date of Patent: Aug. 4, 2026

(54) OPTIMIZED SYNTHETIC CONSENSUS IMMUNOGENIC COMPOSITIONS TARGETING FIBROBLAST ACTIVATION PROTEIN

(71) Applicants: The Trustees of the University of Pennsylvania, Philadelphia, PA (US); THE WISTAR INSTITUTE OF ANATOMY AND BIOLOGY, Philadelphia, PA (US)

(72) Inventors: David Weiner, Merion, PA (US); Elizabeth Duperret, Philadelphia, PA (US)

(73) Assignees: The Trustees of the University of Pennsylvania, Philadelphia, PA (US); The Wistar Institute of Anatomy and Biology, Philadelphia, PA (US)

( * ) Notice: Subject to any disclaimer, the term of this patent is extended or adjusted under 35 U.S.C. 154(b) by 453 days.

(21) Appl. No.: 16/335,355

(22) PCT Filed: Sep. 21, 2017

(86) PCT No.: PCT/US2017/052701
§ 371 (c)(1),
(2) Date: Mar. 21, 2019

(87) PCT Pub. No.: WO2018/057727
PCT Pub. Date: Mar. 29, 2018

(65) Prior Publication Data
US 2019/0328855 A1 Oct. 31, 2019

Related U.S. Application Data

(60) Provisional application No. 62/397,469, filed on Sep. 21, 2016.

(51) Int. Cl.

| | |
|---|---|
| *A61K 9/00* | (2006.01) |
| *A61K 39/00* | (2006.01) |
| *A61K 41/00* | (2020.01) |
| *A61P 35/00* | (2006.01) |
| *A61P 37/04* | (2006.01) |
| *C07K 14/47* | (2006.01) |
| *C12N 9/64* | (2006.01) |
| *C12N 15/86* | (2006.01) |

(52) U.S. Cl.
CPC ........ *A61K 9/0019* (2013.01); *A61K 39/0011* (2013.01); *A61K 41/0047* (2013.01); *A61P 35/00* (2018.01); *A61P 37/04* (2018.01); *C07K 14/47* (2013.01); *C12N 9/6424* (2013.01); *C12N 15/86* (2013.01); *A61K 2039/53* (2013.01); *A61K 2039/54* (2013.01); *C12Y 304/21026* (2013.01)

(58) Field of Classification Search
CPC .. A61K 38/00; A61K 9/0019; A61K 39/0011; A61K 41/0047; A61P 37/04; A61P 35/00; C07K 14/47; C12N 9/6424; C12N 15/86
See application file for complete search history.

(56) References Cited

U.S. PATENT DOCUMENTS

| | | | |
|---|---|---|---|
| 6,472,375 B1 | 10/2002 | Hoon | |
| 11,464,841 B2 * | 10/2022 | Weiner | A61K 39/39 |
| 2009/0253778 A1 | 10/2009 | Reisfeld | |
| 2011/0064751 A1 | 3/2011 | Moessner | |
| 2014/0113960 A1 | 4/2014 | Bancel | |
| 2014/0271724 A1 | 9/2014 | Ertl | |
| 2016/0114030 A1 | 4/2016 | Weiner | |
| 2016/0264671 A1 * | 9/2016 | Kufer | C07K 16/2863 |
| 2018/0186891 A1 * | 7/2018 | DeLuca | C07K 16/40 |

FOREIGN PATENT DOCUMENTS

WO 2013151672 10/2013

OTHER PUBLICATIONS

NCBI Reference Sequence: NP_004451.2; Sep. 6, 2021; pp. 1-4.*
BLAST search; Sep. 13, 2021; p. 1.*
Scanlan et al. (Proc. Natl. Acad. Sci. USA. Jun. 7, 1994; 91 (12): 5657-61).*
Lazar et al. (Molecular and Cellular Biology, 1988, 8: 1247-52).*
Kost et al. (Nat. Biotechnol. May 2005; 23 (5): 567-75).*
Liu et al. (Emerg. Microbes Infect. Apr. 6, 2016; 5 (4): e33; pp. 1-6).*
Kumar et al. (DNA Cell Biol. Jul. 2006; 25 (7): 383-92).*
Chen et al., 2015, "A whole-cell tumor vaccine modified to express fibroblast activation protein induces antitumor immunity against both tumor cells and cancer-associated fibroblasts," Sci Rep, 5:14421.
Xia et al., 2016, "Anti-tumor effects of DNA vaccine targeting human fibroblast activation protein α by producing specific immune responses and altering tumor microenvironment in the 4T1 murine breast cancer model," Cancer Immunol Immunother, 65:613-624.
Zhang and Ertl, 2016, "Depletion of FAP+ cells reduces immuno-suppressive cells and improves metabolism and functions CD8+T cells within tumors," Oncotarget, 7:23282-23299.

* cited by examiner

*Primary Examiner* — Gregory S Emch
(74) *Attorney, Agent, or Firm* — Riverside Law LLP

(57) ABSTRACT

Provided herein is an immunogenic composition comprising a synthetic consensus FAP antigen. Also disclosed herein is a method of treating or preventing a tumor associated pathology in a subject in need thereof, by administering the immunogenic composition to the subject.

9 Claims, 15 Drawing Sheets
Specification includes a Sequence Listing.

A

B

C

A   TRAMPC2 prostate cancer model

| Native | Synthetic consensus |
|---|---|
| KDGGLTFWYKMILPP (SEQ ID NO:13) | EVDGTLWYKMILPP (SEQ ID NO:22) |
| AVNWTYLASKEGIV (SEQ ID NO:14) | AVNWISYLASKEGIV (SEQ ID NO:23) |
| YLASKEGIVIALVDG (SEQ ID NO:15) | YLASKEGIVIALVDG (SEQ ID NO:15) |
| LEHYKNSTVMARAEY (SEQ ID NO:16) | LEHYKNSTVMARAEY (SEQ ID NO:16) |
| HGTADDNVHFQNSAQ (SEQ ID NO:17) | HGTADDNVHFQNSAQ (SEQ ID NO:17) |
| VDFQAMWYSDQNHGI (SEQ ID NO:18) | VDFQAMWYSDQNHGI (SEQ ID NO:18) |
| NIETRESYIILSNST (SEQ ID NO:19) | NIETGESYIILSNST (SEQ ID NO:24) |
| GLSPDRQFVYLESDY (SEQ ID NO:20) | GLSPDRQFVYLESDY (SEQ ID NO:20) |
| ATYYIYDLQNGEFVR (SEQ ID NO:21) | ATYYIYDLQNGEFVR (SEQ ID NO:21) |

SEQUENCE LISTING

```
<160> NUMBER OF SEQ ID NOS: 24

<210> SEQ ID NO 1
<211> LENGTH: 2202
<212> TYPE: DNA
<213> ORGANISM: Artificial sequence
<220> FEATURE:
<223> OTHER INFORMATION: synthetic consensus nucleotide sequence for
      human FAP

<400> SEQUENCE: 1
ctgaggcctt ctagagtgca caactccgag ggcccaacca gagccctgac actgaaggac      60
atcctgaatg gcaccttttc ttacaagaca ttctttccca actggatctc tggccaggag     120
tatctgcacc agagcgccga taacaacatc atcctgtaca acatcgagac aggcgagagc     180
tacacaatcc tgtccaactc taccatgaag agcgtgaacg cctccaatta cggcctgagc     240
cctgacaggc agttcgccta cctggagtct gattatagca agctgtggag atactcctat     300
accgccacat accacatcta tgatctgatc aatggcgagt ttgtgcggga gaacgagctg     360
ccccgcccta tccagtacct gtgctggagc cccgtgggca gcaagctggc atacgtgtat     420
cagaacaata tctatctgaa gcagaggccc agggaccctc ccttccagat cacatccaac     480
ggcaaggaga ataagatctt taacggcatc cccgattggg tgtacgagga ggagatgctg     540
gccaccaagt atgccctgtg gtggagccct aatggcaagt tcctggccta cgccgagttt     600
aacgacacag atatcccagt gatcgcctat tcctactatg gcgacgagca gtacccccgg     660
```

-continued

```
accatcaata tcccatatcc caaggcagga gcaaagaacc caacagtgcg cgtgttcatc        720
atcgatacca catacccaga gcacgtggga ccaaaggagg tgcctgtgcc agccatgatc        780
gccagctccg actactactt cagctggctg acctgggtga cagatgagag gatctgtctg        840
cagtggctga agagaatcca gaacgtgagc gtgctgtcta tctgcgactt cagggaggat        900
tggaacacct gggactgtcc taagacacag gagcacatcg aggagagcag aaccggatgg        960
gccggcggct tcttcgtgag cacaccagtg ttctctagcg acgccatcag ctactataag       1020
atcttttccg acaaggatgg ctacaagcac atccactata tcaaggatac cgtggagaat       1080
gccatccaga tcacatctgg caagtgggag gccatcaaca tcttcagggt gacccaggac       1140
agcctgttct actcctctaa tgagtttgag ggctacccag gcaggagaaa catctataga       1200
atcagcatcg gctcctaccc acccagcaag aagtgcgtga cctgtcacct gcggaaggag       1260
aggtgccagt actatacagc cagcttttcc gattacgcca agtactatgc cctgatctgt       1320
tatggccccg gcatccctat ctccaccctg cacgacggcc ggacagatca ggagatcaag       1380
atcctggagg agaataagga gctggagaat gccctgaaga acatccagct gcctaaggag       1440
gagatcaaga agctggaggt ggacggcatc accctgtggt acaagatgat cctgcctcca       1500
cagttcgatc ggtctaagaa gtatcccctg ctgatccagg tgtacggcgg accttgctct       1560
cagagcgtgc gcagcgtgtt ttccatctct tggatctcct acctggcctc taaggagggc       1620
atcgtggtgg ccctggtgga cggaagggga accgccttcc agggcgataa gctgctgtac       1680
gccgtgtatc gcaagctggg cgtgtacgag gtggaggacc agatcacagc cgtgcggaag       1740
ttcatcgaga tgggctttat cgatgagaag aggatcgcaa tctggggatg ggcatacggc       1800
ggatatgtga gctccctggc cctggcatct ggaaccggcc tgttcaagtg tggcatcgcc       1860
gtggccccag tgtctagctg ggagtactat gcctccatct acaccgagag gttcatgggc       1920
ctgcccacaa gtccgacaa tctggagcac tataagaact ctaccgtgat ggccagggcc       1980
gagtacttca gaaacgtgga ttatctgctg atccacggca cagccgacga taatgtgcac       2040
ttccagaact ccgcccagat cgccaaggcc ctggtgaatg cccaggtgga ctttcaggcc       2100
atgtggtact ctgatcagaa ccacggcatc tctggcctga gcaccaagca cctgtatacc       2160
cacatgacac acttcctgaa gcagtgcttt agcctgtccg ac                          2202
```

```
<210> SEQ ID NO 2
<211> LENGTH: 734
<212> TYPE: PRT
<213> ORGANISM: Artificial sequence
<220> FEATURE:
<223> OTHER INFORMATION: synthetic consensus amino acid sequence for
      human FAP

<400> SEQUENCE: 2

Leu Arg Pro Ser Arg Val His Asn Ser Glu Gly Pro Thr Arg Ala Leu
1               5                   10                  15

Thr Leu Lys Asp Ile Leu Asn Gly Thr Phe Ser Tyr Lys Thr Phe Phe
            20                  25                  30

Pro Asn Trp Ile Ser Gly Gln Glu Tyr Leu His Gln Ser Ala Asp Asn
        35                  40                  45

Asn Ile Ile Leu Tyr Asn Ile Glu Thr Gly Glu Ser Tyr Thr Ile Leu
    50                  55                  60

Ser Asn Ser Thr Met Lys Ser Val Asn Ala Ser Asn Tyr Gly Leu Ser
65                  70                  75                  80

Pro Asp Arg Gln Phe Ala Tyr Leu Glu Ser Asp Tyr Ser Lys Leu Trp
```

-continued

```
                    85              90              95

Arg Tyr Ser Tyr Thr Ala Thr Tyr His Ile Tyr Asp Leu Ile Asn Gly
            100             105             110

Glu Phe Val Arg Glu Asn Glu Leu Pro Arg Pro Ile Gln Tyr Leu Cys
            115             120             125

Trp Ser Pro Val Gly Ser Lys Leu Ala Tyr Val Tyr Gln Asn Asn Ile
    130             135             140

Tyr Leu Lys Gln Arg Pro Arg Asp Pro Pro Phe Gln Ile Thr Ser Asn
145             150             155             160

Gly Lys Glu Asn Lys Ile Phe Asn Gly Ile Pro Asp Trp Val Tyr Glu
            165             170             175

Glu Glu Met Leu Ala Thr Lys Tyr Ala Leu Trp Trp Ser Pro Asn Gly
            180             185             190

Lys Phe Leu Ala Tyr Ala Glu Phe Asn Asp Thr Asp Ile Pro Val Ile
            195             200             205

Ala Tyr Ser Tyr Tyr Gly Asp Glu Gln Tyr Pro Arg Thr Ile Asn Ile
    210             215             220

Pro Tyr Pro Lys Ala Gly Ala Lys Asn Pro Thr Val Arg Val Phe Ile
225             230             235             240

Ile Asp Thr Thr Tyr Pro Glu His Val Gly Pro Lys Glu Val Pro Val
            245             250             255

Pro Ala Met Ile Ala Ser Ser Asp Tyr Tyr Phe Ser Trp Leu Thr Trp
            260             265             270

Val Thr Asp Glu Arg Ile Cys Leu Gln Trp Leu Lys Arg Ile Gln Asn
            275             280             285

Val Ser Val Leu Ser Ile Cys Asp Phe Arg Glu Asp Trp Asn Thr Trp
    290             295             300

Asp Cys Pro Lys Thr Gln Glu His Ile Glu Glu Ser Arg Thr Gly Trp
305             310             315             320

Ala Gly Gly Phe Phe Val Ser Thr Pro Val Phe Ser Ser Asp Ala Ile
            325             330             335

Ser Tyr Tyr Lys Ile Phe Ser Asp Lys Asp Gly Tyr Lys His Ile His
            340             345             350

Tyr Ile Lys Asp Thr Val Glu Asn Ala Ile Gln Ile Thr Ser Gly Lys
    355             360             365

Trp Glu Ala Ile Asn Ile Phe Arg Val Thr Gln Asp Ser Leu Phe Tyr
    370             375             380

Ser Ser Asn Glu Phe Glu Gly Tyr Pro Gly Arg Arg Asn Ile Tyr Arg
385             390             395             400

Ile Ser Ile Gly Ser Tyr Pro Pro Ser Lys Lys Cys Val Thr Cys His
            405             410             415

Leu Arg Lys Glu Arg Cys Gln Tyr Tyr Thr Ala Ser Phe Ser Asp Tyr
            420             425             430

Ala Lys Tyr Tyr Ala Leu Ile Cys Tyr Gly Pro Gly Ile Pro Ile Ser
            435             440             445

Thr Leu His Asp Gly Arg Thr Asp Gln Glu Ile Lys Ile Leu Glu Glu
    450             455             460

Asn Lys Glu Leu Glu Asn Ala Leu Lys Asn Ile Gln Leu Pro Lys Glu
465             470             475             480

Glu Ile Lys Lys Leu Glu Val Asp Gly Ile Thr Leu Trp Tyr Lys Met
            485             490             495

Ile Leu Pro Pro Gln Phe Asp Arg Ser Lys Lys Tyr Pro Leu Leu Ile
            500             505             510
```

-continued

```
Gln Val Tyr Gly Gly Pro Cys Ser Gln Ser Val Arg Ser Val Phe Ser
        515                 520                 525

Ile Ser Trp Ile Ser Tyr Leu Ala Ser Lys Glu Gly Ile Val Val Ala
        530                 535                 540

Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
                565                 570                 575

Ala Val Arg Lys Phe Ile Glu Met Gly Phe Ile Asp Glu Lys Arg Ile
                580                 585                 590

Ala Ile Trp Gly Trp Ala Tyr Gly Gly Tyr Val Ser Ser Leu Ala Leu
                595                 600                 605

Ala Ser Gly Thr Gly Leu Phe Lys Cys Gly Ile Ala Val Ala Pro Val
        610                 615                 620

Ser Ser Trp Glu Tyr Tyr Ala Ser Ile Tyr Thr Glu Arg Phe Met Gly
625                 630                 635                 640

Leu Pro Thr Lys Ser Asp Asn Leu Glu His Tyr Lys Asn Ser Thr Val
                645                 650                 655

Met Ala Arg Ala Glu Tyr Phe Arg Asn Val Asp Tyr Leu Leu Ile His
                660                 665                 670

Gly Thr Ala Asp Asp Asn Val His Phe Gln Asn Ser Ala Gln Ile Ala
        675                 680                 685

Lys Ala Leu Val Asn Ala Gln Val Asp Phe Gln Ala Met Trp Tyr Ser
        690                 695                 700

Asp Gln Asn His Gly Ile Ser Gly Leu Ser Thr Lys His Leu Tyr Thr
705                 710                 715                 720

His Met Thr His Phe Leu Lys Gln Cys Phe Ser Leu Ser Asp
                725                 730
```

```
<210> SEQ ID NO 3
<211> LENGTH: 2256
<212> TYPE: DNA
<213> ORGANISM: Artificial sequence
<220> FEATURE:
<223> OTHER INFORMATION: synthetic consensus nucleotide sequence for
      human FAP operably linked to sequence encoding an IgE leader

<400> SEQUENCE: 3
atggactgga cctggattct gttcctggtg gcagcagcaa caagggtgca ctccctgagg      60
ccttctagag tgcacaactc cgagggccca accagagccc tgacactgaa ggacatcctg     120
aatggcacct tttcttacaa gacattcttt cccaactgga tctctggcca ggagtatctg     180
caccagagcg ccgataacaa catcatcctg tacaacatcg agacaggcga gagctacaca     240
atcctgtcca actctaccat gaagagcgtg aacgcctcca attacggcct gagccctgac     300
aggcagttcg cctacctgga gtctgattat agcaagctgt ggagatactc ctataccgcc     360
acataccaca tctatgatct gatcaatggc gagtttgtgc gggagaacga gctgcccgc      420 cctatccagt acctgtgctg gagccccgtg ggcagcaagc tggcatacgt gtatcagaac     480
aatatctatc tgaagcagag gcccagggac cctcccttcc agatcacatc caacggcaag     540
gagaataaga tctttaacgg catccccgat tgggtgtacg aggaggagat gctggccacc     600
aagtatgccc tgtggtggag ccctaatggc aagttcctgg cctacgccga gtttaacgac     660
acagatatcc agtgatcgc ctattcctac tatggcgacg agcagtaccc ccggaccatc     720
aatatcccat atcccaaggc aggagcaaag aacccaacag tgcgcgtgtt catcatcgat     780
```

-continued

```
accacatacc cagagcacgt gggaccaaag gaggtgcctg tgccagccat gatcgccagc    840
tccgactact acttcagctg gctgacctgg gtgacagatg agaggatctg tctgcagtgg    900
ctgaagagaa tccagaacgt gagcgtgctg tctatctgcg acttcaggga ggattggaac    960
acctgggact gtcctaagac acaggagcac atcgaggaga gcagaaccgg atgggccggc   1020
ggcttcttcg tgagcacacc agtgttctct agcgacgcca tcagctacta taagatcttt   1080
tccgacaagg atggctacaa gcacatccac tatatcaagg ataccgtgga gaatgccatc   1140
cagatcacat ctggcaagtg ggaggccatc aacatcttca gggtgaccca ggacagcctg   1200
ttctactcct ctaatgagtt tgagggctac ccaggcagga gaaacatcta tagaatcagc   1260
atcggctcct acccacccag caagaagtgc gtgacctgtc acctgcggaa ggagaggtgc   1320
cagtactata cagccagctt ttccgattac gccaagtact atgccctgat ctgttatggc   1380
cccggcatcc ctatctccac cctgcacgac ggccggacag atcaggagat caagatcctg   1440
gaggagaata aggagctgga gaatgccctg aagaacatcc agctgcctaa ggaggagatc   1500
aagaagctgg aggtggacgg catcaccctg tggtacaaga tgatcctgcc tccacagttc   1560
gatcggtcta agaagtatcc cctgctgatc caggtgtacg gcggaccttg ctctcagagc   1620
gtgcgcagcg tgttttccat ctcttggatc tcctacctgg cctctaagga gggcatcgtg   1680
gtggccctgg tggacggaag gggaaccgcc ttccagggcg ataagctgct gtacgccgtg   1740
tatcgcaagc tgggcgtgta cgaggtggag gaccagatca cagccgtgcg gaagttcatc   1800
gagatgggct ttatcgatga gaagaggatc gcaatctggg gatgggcata cggcggatat   1860
gtgagctccc tggccctggc atctggaacc ggcctgttca gtgtggcat cgccgtggcc   1920 ccagtgtcta gctgggagta ctatgcctcc atctacaccg agaggttcat gggcctgccc   1980
acaaagtccg acaatctgga gcactataag aactctaccg tgatggccag ggccgagtac   2040
ttcagaaacg tggattatct gctgatccac ggcacagccg acgataatgt gcacttccag   2100
aactccgccc agatcgccaa ggccctggtg aatgcccagg tggactttca ggccatgtgg   2160
tactctgatc agaaccacgg catctctggc ctgagcacca gcacctgta tacccacatg   2220 acacacttcc tgaagcagtg ctttagcctg tccgac                            2256
```

```
<210> SEQ ID NO 4
<211> LENGTH: 752
<212> TYPE: PRT
<213> ORGANISM: Artificial sequence
<220> FEATURE:
<223> OTHER INFORMATION: synthetic consensus amino acid sequence for
      human FAP operably linked to an IgE leader sequence

<400> SEQUENCE: 4

Met Asp Trp Thr Trp Ile Leu Phe Leu Val Ala Ala Ala Thr Arg Val
1               5                   10                  15

His Ser Leu Arg Pro Ser Arg Val His Asn Ser Glu Gly Pro Thr Arg
            20                  25                  30

Ala Leu Thr Leu Lys Asp Ile Leu Asn Gly Thr Phe Ser Tyr Lys Thr
        35                  40                  45

Phe Phe Pro Asn Trp Ile Ser Gly Gln Glu Tyr Leu His Gln Ser Ala
    50                  55                  60

Asp Asn Asn Ile Ile Leu Tyr Asn Ile Glu Thr Gly Glu Ser Tyr Thr
65                  70                  75                  80

Ile Leu Ser Asn Ser Thr Met Lys Ser Val Asn Ala Ser Asn Tyr Gly
                85                  90                  95
```

-continued

```
Leu Ser Pro Asp Arg Gln Phe Ala Tyr Leu Glu Ser Asp Tyr Ser Lys
            100                 105                 110

Leu Trp Arg Tyr Ser Tyr Thr Ala Thr Tyr His Ile Tyr Asp Leu Ile
            115                 120                 125

Asn Gly Glu Phe Val Arg Glu Asn Glu Leu Pro Arg Pro Ile Gln Tyr
            130                 135                 140

Leu Cys Trp Ser Pro Val Gly Ser Lys Leu Ala Tyr Val Tyr Gln Asn
145                 150                 155                 160

Asn Ile Tyr Leu Lys Gln Arg Pro Arg Asp Pro Pro Phe Gln Ile Thr
                165                 170                 175

Ser Asn Gly Lys Glu Asn Lys Ile Phe Asn Gly Ile Pro Asp Trp Val
            180                 185                 190

Tyr Glu Glu Glu Met Leu Ala Thr Lys Tyr Ala Leu Trp Trp Ser Pro
            195                 200                 205

Asn Gly Lys Phe Leu Ala Tyr Ala Glu Phe Asn Asp Thr Asp Ile Pro
            210                 215                 220

Val Ile Ala Tyr Ser Tyr Tyr Gly Asp Glu Gln Tyr Pro Arg Thr Ile
225                 230                 235                 240

Asn Ile Pro Tyr Pro Lys Ala Gly Ala Lys Asn Pro Thr Val Arg Val
                245                 250                 255

Phe Ile Ile Asp Thr Thr Tyr Pro Glu His Val Gly Pro Lys Glu Val
                260                 265                 270

Pro Val Pro Ala Met Ile Ala Ser Ser Asp Tyr Tyr Phe Ser Trp Leu
            275                 280                 285

Thr Trp Val Thr Asp Glu Arg Ile Cys Leu Gln Trp Leu Lys Arg Ile
            290                 295                 300

Gln Asn Val Ser Val Leu Ser Ile Cys Asp Phe Arg Glu Asp Trp Asn
305                 310                 315                 320

Thr Trp Asp Cys Pro Lys Thr Gln Glu His Ile Glu Glu Ser Arg Thr
                325                 330                 335

Gly Trp Ala Gly Gly Phe Phe Val Ser Thr Pro Val Phe Ser Ser Asp
            340                 345                 350

Ala Ile Ser Tyr Tyr Lys Ile Phe Ser Asp Lys Asp Gly Tyr Lys His
            355                 360                 365

Ile His Tyr Ile Lys Asp Thr Val Glu Asn Ala Ile Gln Ile Thr Ser
            370                 375                 380

Gly Lys Trp Glu Ala Ile Asn Ile Phe Arg Val Thr Gln Asp Ser Leu
385                 390                 395                 400

Phe Tyr Ser Ser Asn Glu Phe Glu Gly Tyr Pro Gly Arg Arg Asn Ile
                405                 410                 415

Tyr Arg Ile Ser Ile Gly Ser Tyr Pro Pro Ser Lys Lys Cys Val Thr
                420                 425                 430

Cys His Leu Arg Lys Glu Arg Cys Gln Tyr Tyr Thr Ala Ser Phe Ser
            435                 440                 445

Asp Tyr Ala Lys Tyr Tyr Ala Leu Ile Cys Tyr Gly Pro Gly Ile Pro
            450                 455                 460

Ile Ser Thr Leu His Asp Gly Arg Thr Asp Gln Glu Ile Lys Ile Leu
465                 470                 475                 480

Glu Glu Asn Lys Glu Leu Glu Asn Ala Leu Lys Asn Ile Gln Leu Pro
                485                 490                 495

Lys Glu Glu Ile Lys Lys Leu Glu Val Asp Gly Ile Thr Leu Trp Tyr
                500                 505                 510
```

-continued

```
Lys Met Ile Leu Pro Pro Gln Phe Asp Arg Ser Lys Lys Tyr Pro Leu
        515             520             525

Leu Ile Gln Val Tyr Gly Gly Pro Cys Ser Gln Ser Val Arg Ser Val
        530             535             540

Phe Ser Ile Ser Trp Ile Ser Tyr Leu Ala Ser Lys Glu Gly Ile Val
545                 550             555                 560

Val Ala Leu Val Asp Gly Arg Gly Thr Ala Phe Gln Gly Asp Lys Leu
                565             570             575

Leu Tyr Ala Val Tyr Arg Lys Leu Gly Val Tyr Glu Val Glu Asp Gln
            580             585             590

Ile Thr Ala Val Arg Lys Phe Ile Glu Met Gly Phe Ile Asp Glu Lys
            595             600             605

Arg Ile Ala Ile Trp Gly Trp Ala Tyr Gly Gly Tyr Val Ser Ser Leu
        610             615             620

Ala Leu Ala Ser Gly Thr Gly Leu Phe Lys Cys Gly Ile Ala Val Ala
625                 630             635                 640

Pro Val Ser Ser Trp Glu Tyr Tyr Ala Ser Ile Tyr Thr Glu Arg Phe
                645             650             655

Met Gly Leu Pro Thr Lys Ser Asp Asn Leu Glu His Tyr Lys Asn Ser
            660             665             670

Thr Val Met Ala Arg Ala Glu Tyr Phe Arg Asn Val Asp Tyr Leu Leu
            675             680             685

Ile His Gly Thr Ala Asp Asp Asn Val His Phe Gln Asn Ser Ala Gln
        690             695             700

Ile Ala Lys Ala Leu Val Asn Ala Gln Val Asp Phe Gln Ala Met Trp
705                 710             715                 720

Tyr Ser Asp Gln Asn His Gly Ile Ser Gly Leu Ser Thr Lys His Leu
                725             730             735

Tyr Thr His Met Thr His Phe Leu Lys Gln Cys Phe Ser Leu Ser Asp
            740             745             750
```

<210> SEQ ID NO 5
<211> LENGTH: 2205
<212> TYPE: DNA
<213> ORGANISM: Artificial sequence
<220> FEATURE:
<223> OTHER INFORMATION: synthetic consensus nucleotide sequence for
      mouse FAP

<400> SEQUENCE: 5

```
ctgcggcctt cccgcgtgta caagccagag ggcaacacca agcgcgccct gacactgaag       60
gatatcctga acggaacctt cagctacaag acattctttc ccaactggat ctccggccag      120
gagtacctgc accagtctga ggacgataac atcgtgtttt acaacatcga gacaggagag      180
tcctacatca tcctgtccaa ctctacaatg aagtctgtga acgctagcga ctacggcctg      240
tctcctgata ggcagttcgt gtacctggag agcgactact ccaagctgtg agatacagc      300 tacaccgcca catactacat ctacgatctg cagaacggcg agtttgtgag gggatacgag      360
ctgcccagac ctatccagta cctgtgctgg tccctgtgg  gatctaagct ggcctacgtg      420
taccagaaca acatctacct gaagcagcgg ccaggcgacc ctcccttcca gatcacctac      480
aacggccgcg agaacaagat ctttaacgga atccccgatt gggtgtacga ggaggagatg      540
ctggctacaa gtacgccct gtggtggagc cccaacggca agttcctggc ttacgccgag      600
tttaacgaca ccgatatccc agtgatcgcc tacagctact acggcgacgg acagtacccc      660
aggacaatca acatcccata ccccaaggct ggagccaaga accccgtggt gagagtgttc      720
```

```
atcgtggata ccacatacccc acaccacgtg ggaccaatgg aggtgcctgt gccagagatg        780
atcgctagct ccgactacta ctttagctgg ctgacctggg tgacagatga gagggtgtgc        840
ctgcagtggc tgaagcgcgt gcagaacgtg tctgtgctga gcatctgcga cttcagggag        900
gattggcacg cctgggagtg tcctaagaac caggagcacg tggaggagtc cagaaccgga        960
tgggccggcg gcttcttcgt gagcacacca gtgttcagcc aggacgccat ctcctactac       1020
aagatctttt ctgacaagga tggatacaag cacatccact acatcaagga taccgtggag       1080
aacgctatcc agatcacaag cggcaagtgg gaggccatct acatcttccg ggtgacccag       1140
gactccctgt tctactctag caacgagttt gagggctacc caggaaggag aaacatctac       1200
cgcatctcta tcggctcctc tccacccagc aagaagtgcg tgacctgtca cctgaggaag       1260
gagagatgcc agtactacac agctagcttt tccgactacg ctaagtacta cgctctggtg       1320
tgctacggac caggactgcc tatctccacc ctgcacgacg gaagaacaga tcaggagatc       1380
aagatcctgg aggagaacaa ggagctggag aacgccctga gaacatcca gctgcccaag       1440 gaggagatca gaagctgga ggtggacggc atcaccctgt ggtacaagat gatcctgcct       1500
ccacagttcg atcggtccaa gaagtacccc ctgctgatcc aggtgtacgg cggaccttgc       1560
tctcagagcg tgaagagcgt gttcgctgtg aactggatca gctacctggc ctccaaggag       1620
ggcatcgtga tcgctctggt ggacggaagg ggaaccgctt tccagggcga taagtttctg       1680
tacgccgtgt accgcaagct gggagtgtac gaggtggagg accagatcac agccgtgagg       1740
aagttcatcg agatgggctt tatcgatgag aagagaatcg ctatctgggg atgggcctac       1800
ggcggatacg tgagctccct ggctctggct tccggaaccg gactgttcaa gtgtggaatc       1860
gctgtggccc cagtgtctag ctgggagtac tacgcctcta tctacaccga gaggtttatg       1920
ggcctgccca caaaggacga taacctggag cactacaaga acagcaccgt gatggctcgg       1980
gccgagtact ccgcaacgt ggactacctg ctgatccacg gaacagctga cgataacgtg       2040
cacttccaga acagcgccca gatcgctaag gccctggtga cgctcaggt ggactttcag       2100 gccatgtggt actccgatca gaaccacggc atctccggcg gatctacaaa ccacctgtac       2160
acccacatga cacacttcct gaagcagtgc ttttcccctgt ctgac                        2205
```

<210> SEQ ID NO 6
<211> LENGTH: 735
<212> TYPE: PRT
<213> ORGANISM: Artificial sequence
<220> FEATURE:
<223> OTHER INFORMATION: synthetic consensus amino acid sequence for
      mouse FAP

<400> SEQUENCE: 6

```
Leu Arg Pro Ser Arg Val Tyr Lys Pro Glu Gly Asn Thr Lys Arg Ala
1               5                   10                  15

Leu Thr Leu Lys Asp Ile Leu Asn Gly Thr Phe Ser Tyr Lys Thr Phe
            20                  25                  30

Phe Pro Asn Trp Ile Ser Gly Gln Glu Tyr Leu His Gln Ser Glu Asp
        35                  40                  45

Asp Asn Ile Val Phe Tyr Asn Ile Glu Thr Gly Glu Ser Tyr Ile Ile
        50                  55                  60

Leu Ser Asn Ser Thr Met Lys Ser Val Asn Ala Ser Asp Tyr Gly Leu
65                  70                  75                  80

Ser Pro Asp Arg Gln Phe Val Tyr Leu Glu Ser Asp Tyr Ser Lys Leu
                85                  90                  95
```

-continued

```
Trp Arg Tyr Ser Tyr Thr Ala Thr Tyr Tyr Ile Tyr Asp Leu Gln Asn
            100                 105                 110

Gly Glu Phe Val Arg Gly Tyr Glu Leu Pro Arg Pro Ile Gln Tyr Leu
            115                 120                 125

Cys Trp Ser Pro Val Gly Ser Lys Leu Ala Tyr Val Tyr Gln Asn Asn
            130                 135                 140

Ile Tyr Leu Lys Gln Arg Pro Gly Asp Pro Pro Phe Gln Ile Thr Tyr
145                 150                 155                 160

Asn Gly Arg Glu Asn Lys Ile Phe Asn Gly Ile Pro Asp Trp Val Tyr
                165                 170                 175

Glu Glu Glu Met Leu Ala Thr Lys Tyr Ala Leu Trp Trp Ser Pro Asn
            180                 185                 190

Gly Lys Phe Leu Ala Tyr Ala Glu Phe Asn Asp Thr Asp Ile Pro Val
            195                 200                 205

Ile Ala Tyr Ser Tyr Tyr Gly Asp Gly Gln Tyr Pro Arg Thr Ile Asn
            210                 215                 220

Ile Pro Tyr Pro Lys Ala Gly Ala Lys Asn Pro Val Val Arg Val Phe
225                 230                 235                 240

Ile Val Asp Thr Thr Tyr Pro His His Val Gly Pro Met Glu Val Pro
                245                 250                 255

Val Pro Glu Met Ile Ala Ser Ser Asp Tyr Tyr Phe Ser Trp Leu Thr
            260                 265                 270

Trp Val Thr Asp Glu Arg Val Cys Leu Gln Trp Leu Lys Arg Val Gln
            275                 280                 285

Asn Val Ser Val Leu Ser Ile Cys Asp Phe Arg Glu Asp Trp His Ala
            290                 295                 300

Trp Glu Cys Pro Lys Asn Gln Glu His Val Glu Glu Ser Arg Thr Gly
305                 310                 315                 320

Trp Ala Gly Gly Phe Phe Val Ser Thr Pro Val Phe Ser Gln Asp Ala
                325                 330                 335

Ile Ser Tyr Tyr Lys Ile Phe Ser Asp Lys Asp Gly Tyr Lys His Ile
                340                 345                 350

His Tyr Ile Lys Asp Thr Val Glu Asn Ala Ile Gln Ile Thr Ser Gly
            355                 360                 365

Lys Trp Glu Ala Ile Tyr Ile Phe Arg Val Thr Gln Asp Ser Leu Phe
            370                 375                 380

Tyr Ser Ser Asn Glu Phe Glu Gly Tyr Pro Gly Arg Arg Asn Ile Tyr
385                 390                 395                 400

Arg Ile Ser Ile Gly Ser Ser Pro Pro Ser Lys Lys Cys Val Thr Cys
                405                 410                 415

His Leu Arg Lys Glu Arg Cys Gln Tyr Tyr Thr Ala Ser Phe Ser Asp
                420                 425                 430

Tyr Ala Lys Tyr Tyr Ala Leu Val Cys Tyr Gly Pro Gly Leu Pro Ile
            435                 440                 445

Ser Thr Leu His Asp Gly Arg Thr Asp Gln Glu Ile Lys Ile Leu Glu
            450                 455                 460

Glu Asn Lys Glu Leu Glu Asn Ala Leu Lys Asn Ile Gln Leu Pro Lys
465                 470                 475                 480

Glu Glu Ile Lys Lys Leu Glu Val Asp Gly Ile Thr Leu Trp Tyr Lys
                485                 490                 495

Met Ile Leu Pro Pro Gln Phe Asp Arg Ser Lys Lys Tyr Pro Leu Leu
            500                 505                 510
```

-continued

```
Ile Gln Val Tyr Gly Gly Pro Cys Ser Gln Ser Val Lys Ser Val Phe
        515                 520                 525

Ala Val Asn Trp Ile Ser Tyr Leu Ala Ser Lys Glu Gly Ile Val Ile
        530                 535                 540

Ala Leu Val Asp Gly Arg Gly Thr Ala Phe Gln Gly Asp Lys Phe Leu
545                 550                 555                 560

Tyr Ala Val Tyr Arg Lys Leu Gly Val Tyr Glu Val Glu Asp Gln Ile
                565                 570                 575

Thr Ala Val Arg Lys Phe Ile Glu Met Gly Phe Ile Asp Glu Lys Arg
                580                 585                 590

Ile Ala Ile Trp Gly Trp Ala Tyr Gly Gly Tyr Val Ser Ser Leu Ala
                595                 600                 605

Leu Ala Ser Gly Thr Gly Leu Phe Lys Cys Gly Ile Ala Val Ala Pro
        610                 615                 620

Val Ser Ser Trp Glu Tyr Tyr Ala Ser Ile Tyr Thr Glu Arg Phe Met
625                 630                 635                 640

Gly Leu Pro Thr Lys Asp Asp Asn Leu Glu His Tyr Lys Asn Ser Thr
                645                 650                 655

Val Met Ala Arg Ala Glu Tyr Phe Arg Asn Val Asp Tyr Leu Leu Ile
                660                 665                 670

His Gly Thr Ala Asp Asp Asn Val His Phe Gln Asn Ser Ala Gln Ile
                675                 680                 685

Ala Lys Ala Leu Val Asn Ala Gln Val Asp Phe Gln Ala Met Trp Tyr
        690                 695                 700

Ser Asp Gln Asn His Gly Ile Ser Gly Gly Ser Thr Asn His Leu Tyr
705                 710                 715                 720

Thr His Met Thr His Phe Leu Lys Gln Cys Phe Ser Leu Ser Asp
                725                 730                 735
```

<210> SEQ ID NO 7
<211> LENGTH: 2259
<212> TYPE: DNA
<213> ORGANISM: Artificial sequence
<220> FEATURE:
<223> OTHER INFORMATION: synthetic consensus nucleotide sequence for
      mouse FAP operably linked to sequence encoding an IgE leader

<400> SEQUENCE: 7

```
atggactgga cctggattct gttcctggtg gctgctgcta cacgggtgca cagcctgcgg      60
ccttcccgcg tgtacaagcc agagggcaac accaagcgcg ccctgacact gaaggatatc     120
ctgaacggaa ccttcagcta caagacattc tttcccaact ggatctccgg ccaggagtac     180
ctgcaccagt ctgaggacga taacatcgtg ttttacaaca tcgagacagg agagtcctac     240
atcatcctgt ccaactctac aatgaagtct gtgaacgcta cgactacgg cctgtctcct      300 gataggcagt tcgtgtacct ggagagcgac tactccaagc tgtggagata cagctacacc     360
gccacatact acatctacga tctgcagaac ggcgagtttg tgaggggata cgagctgccc     420
agacctatcc agtacctgtg ctggtcccct gtgggatcta agctggccta cgtgtaccag     480
aacaacatct acctgaagca gcggccaggc gaccctccct tccagatcac ctacaacggc     540
cgcgagaaca agatctttaa cggaatcccc gattgggtgt acgaggagga gatgctggct     600
acaaagtacg ccctgtggtg gagccccaac ggcaagttcc tggcttacgc cgagtttaac     660
gacaccgata tccagtgat cgcctacagc tactacggcg acggacagta ccccaggaca     720
atcaacatcc ataccccaa ggctggagcc aagaaccccg tggtgagagt gttcatcgtg     780
```

-continued

```
gataccacat acccacacca cgtgggacca atggaggtgc ctgtgccaga gatgatcgct    840
agctccgact actactttag ctggctgacc tgggtgacag atgagagggt gtgcctgcag    900
tggctgaagc gcgtgcagaa cgtgtctgtg ctgagcatct gcgacttcag ggaggattgg    960
cacgcctggg agtgtcctaa gaaccaggag cacgtggagg agtccagaac cggatgggcc   1020
ggcggcttct tcgtgagcac accagtgttc agccaggacg ccatctccta ctacaagatc   1080
ttttctgaca aggatggata caagcacatc cactacatca aggataccgt ggagaacgct   1140
atccagatca caagcggcaa gtgggaggcc atctacatct tccgggtgac ccaggactcc   1200
ctgttctact ctagcaacga gtttgagggc tacccaggaa ggagaaacat ctaccgcatc   1260
tctatcggct cctctccacc cagcaagaag tgcgtgacct gtcacctgag gaaggagaga   1320
tgccagtact acacagctag cttttccgac tacgctaagt actacgctct ggtgtgctac   1380
ggaccaggac tgcctatctc caccctgcac gacggaagaa cagatcagga gatcaagatc   1440
ctggaggaga caaggagct ggagaacgcc ctgaagaaca tccagctgcc caaggaggag   1500
atcaagaagc tggaggtgga cggcatcacc ctgtggtaca gatgatcct gcctccacag   1560 ttcgatcggt ccaagaagta cccccctgctg atccaggtgt acggcggacc ttgctctcag   1620
agcgtgaaga gcgtgttcgc tgtgaactgg atcagctacc tggcctccaa ggagggcatc   1680
gtgatcgctc tggtggacgg aagggggaacc gctttccagg gcgataagtt tctgtacgcc   1740
gtgtaccgca agctgggagt gtacgaggtg gaggaccaga tcacagccgt gaggaagttc   1800
atcgagatgg gctttatcga tgagaagaga atcgctatct ggggatgggc ctacggcgga   1860
tacgtgagct ccctggctct ggcttccgga accggactgt tcaagtgtgg aatcgctgtg   1920
gccccagtgt ctagctggga gtactacgcc tctatctaca ccgagaggtt tatgggcctg   1980
cccacaaagg acgataacct ggagcactac aagaacagca ccgtgatggc tcgggccgag   2040
tacttccgca acgtggacta cctgctgatc cacggaacag ctgacgataa cgtgcacttc   2100
cagaacagcg cccagatcgc taaggccctg gtgaacgctc aggtggactt tcaggccatg   2160
tggtactccg atcagaacca cggcatctcc ggcggatcta caaaccacct gtacacccac   2220
atgacacact tcctgaagca gtgctttttcc ctgtctgac                          2259
```

```
<210> SEQ ID NO 8
<211> LENGTH: 753
<212> TYPE: PRT
<213> ORGANISM: Artificial sequence
<220> FEATURE:
<223> OTHER INFORMATION: synthetic consensus amino acid sequence for
      mouse FAP operably linked to an IgE leader sequence

<400> SEQUENCE: 8

Met Asp Trp Thr Trp Ile Leu Phe Leu Val Ala Ala Ala Thr Arg Val
1               5                   10                  15

His Ser Leu Arg Pro Ser Arg Val Tyr Lys Pro Glu Gly Asn Thr Lys
            20                  25                  30

Arg Ala Leu Thr Leu Lys Asp Ile Leu Asn Gly Thr Phe Ser Tyr Lys
        35                  40                  45

Thr Phe Phe Pro Asn Trp Ile Ser Gly Gln Glu Tyr Leu His Gln Ser
    50                  55                  60

Glu Asp Asp Asn Ile Val Phe Tyr Asn Ile Glu Thr Gly Glu Ser Tyr
65                  70                  75                  80

Ile Ile Leu Ser Asn Ser Thr Met Lys Ser Val Asn Ala Ser Asp Tyr
                85                  90                  95
```

Gly Leu Ser Pro Asp Arg Gln Phe Val Tyr Leu Glu Ser Asp Tyr Ser
            100                 105                 110

Lys Leu Trp Arg Tyr Ser Tyr Thr Ala Thr Tyr Tyr Ile Tyr Asp Leu
            115                 120                 125

Gln Asn Gly Glu Phe Val Arg Gly Tyr Glu Leu Pro Arg Pro Ile Gln
        130                 135             140

Tyr Leu Cys Trp Ser Pro Val Gly Ser Lys Leu Ala Tyr Val Tyr Gln
145                 150             155                 160

Asn Asn Ile Tyr Leu Lys Gln Arg Pro Gly Asp Pro Pro Phe Gln Ile
                165                 170                 175

Thr Tyr Asn Gly Arg Glu Asn Lys Ile Phe Asn Gly Ile Pro Asp Trp
            180                 185                 190

Val Tyr Glu Glu Glu Met Leu Ala Thr Lys Tyr Ala Leu Trp Trp Ser
            195                 200                 205

Pro Asn Gly Lys Phe Leu Ala Tyr Ala Glu Phe Asn Asp Thr Asp Ile
        210                 215             220

Pro Val Ile Ala Tyr Ser Tyr Tyr Gly Asp Gly Gln Tyr Pro Arg Thr
225                 230             235                 240

Ile Asn Ile Pro Tyr Pro Lys Ala Gly Ala Lys Asn Pro Val Val Arg
                245             250                 255

Val Phe Ile Val Asp Thr Thr Tyr Pro His His Val Gly Pro Met Glu
            260                 265             270

Val Pro Val Pro Glu Met Ile Ala Ser Ser Asp Tyr Tyr Phe Ser Trp
            275             280                 285

Leu Thr Trp Val Thr Asp Glu Arg Val Cys Leu Gln Trp Leu Lys Arg
        290             295             300

Val Gln Asn Val Ser Val Leu Ser Ile Cys Asp Phe Arg Glu Asp Trp
305                 310             315                 320

His Ala Trp Glu Cys Pro Lys Asn Gln Glu His Val Glu Glu Ser Arg
                325             330             335

Thr Gly Trp Ala Gly Gly Phe Phe Val Ser Thr Pro Val Phe Ser Gln
            340             345             350

Asp Ala Ile Ser Tyr Tyr Lys Ile Phe Ser Asp Lys Asp Gly Tyr Lys
            355             360             365

His Ile His Tyr Ile Lys Asp Thr Val Glu Asn Ala Ile Gln Ile Thr
        370             375             380

Ser Gly Lys Trp Glu Ala Ile Tyr Ile Phe Arg Val Thr Gln Asp Ser
385                 390             395                 400

Leu Phe Tyr Ser Ser Asn Glu Phe Glu Gly Tyr Pro Gly Arg Arg Asn
                405             410                 415

Ile Tyr Arg Ile Ser Ile Gly Ser Ser Pro Pro Ser Lys Lys Cys Val
            420             425             430

Thr Cys His Leu Arg Lys Glu Arg Cys Gln Tyr Tyr Thr Ala Ser Phe
        435             440             445

Ser Asp Tyr Ala Lys Tyr Tyr Ala Leu Val Cys Tyr Gly Pro Gly Leu
        450             455             460

Pro Ile Ser Thr Leu His Asp Gly Arg Thr Asp Gln Glu Ile Lys Ile
465             470             475                 480

Leu Glu Glu Asn Lys Glu Leu Glu Asn Ala Leu Lys Asn Ile Gln Leu
                485             490                 495

Pro Lys Glu Glu Ile Lys Lys Leu Glu Val Asp Gly Ile Thr Leu Trp
            500             505             510

Tyr Lys Met Ile Leu Pro Pro Gln Phe Asp Arg Ser Lys Lys Tyr Pro

-continued

```
              515                520                525
Leu Leu Ile Gln Val Tyr Gly Gly Pro Cys Ser Gln Ser Val Lys Ser
    530                535                540

Val Phe Ala Val Asn Trp Ile Ser Tyr Leu Ala Ser Lys Glu Gly Ile
545                550                555                560

Val Ile Ala Leu Val Asp Gly Arg Gly Thr Ala Phe Gln Gly Asp Lys
                565                570                575

Phe Leu Tyr Ala Val Tyr Arg Lys Leu Gly Val Tyr Glu Val Glu Asp
            580                585                590

Gln Ile Thr Ala Val Arg Lys Phe Ile Glu Met Gly Phe Ile Asp Glu
            595                600                605

Lys Arg Ile Ala Ile Trp Gly Trp Ala Tyr Gly Gly Tyr Val Ser Ser
    610                615                620

Leu Ala Leu Ala Ser Gly Thr Gly Leu Phe Lys Cys Gly Ile Ala Val
625                630                635                640

Ala Pro Val Ser Ser Trp Glu Tyr Tyr Ala Ser Ile Tyr Thr Glu Arg
                645                650                655

Phe Met Gly Leu Pro Thr Lys Asp Asp Asn Leu Glu His Tyr Lys Asn
            660                665                670

Ser Thr Val Met Ala Arg Ala Glu Tyr Phe Arg Asn Val Asp Tyr Leu
            675                680                685

Leu Ile His Gly Thr Ala Asp Asp Asn Val His Phe Gln Asn Ser Ala
    690                695                700

Gln Ile Ala Lys Ala Leu Val Asn Ala Gln Val Asp Phe Gln Ala Met
705                710                715                720

Trp Tyr Ser Asp Gln Asn His Gly Ile Ser Gly Gly Ser Thr Asn His
                725                730                735

Leu Tyr Thr His Met Thr His Phe Leu Lys Gln Cys Phe Ser Leu Ser
            740                745                750

Asp

<210> SEQ ID NO 9
<211> LENGTH: 2208
<212> TYPE: DNA
<213> ORGANISM: Artificial sequence
<220> FEATURE:
<223> OTHER INFORMATION: Native nucleotide sequence for mouse FAP

<400> SEQUENCE: 9
ctgcggcctt ctcgcgtgta caagccagag ggcaacacca agcgcgctct gacactgaag        60
gatatcctga acggaacctt ctcttacaag acatactttc ccaactggat ctctgagcag       120
gagtacctgc accagagcga ggacgataac atcgtgtttt acaacatcga gacaagggag       180
agctacatca tcctgagcaa ctccaccatg aagagcgtga cgctacaga ctacggcctg        240 tcccctgata ggcagttcgt gtacctggag tctgactaca gcaagctgtg agatactcc        300 tacaccgcca catactacat ctacgatctg cagaacggcg agtttgtgcg gggatacgag       360
ctgccccgcc ctatccagta cctgtgctgg agccctgtgg gctccaagct ggcctacgtg       420
taccagaaca acatctacct gaagcagagg cccggcgacc ctcccttcca gatcacctac       480
acaggcaggg agaacagaat ctttaacgga atccccgact gggtgtacga ggaggagatg       540
ctggctacca gtacgccct gtggtggtcc ctgatggca agttcctggc ttacgtggag         600
tttaacgact ccgatatccc aatcatcgcc tactcttact acggcgatgg acagtacccc       660
aggacaatca acatcccata ccccaaggct ggcgccaaga accccgtggt gagagtgttc       720
```

-continued

```
atcgtggaca ccacataccc acaccacgtg ggacccatgg aggtgcctgt gccagagatg      780
atcgccagct ccgattacta cttttcttgg ctgacctggg tgtctagcga gagggtgtgc      840
ctgcagtggc tgaagagagt gcagaacgtg tccgtgctgt ctatctgcga cttcagggag      900
gattggcacg cttgggagtg tcctaagaac caggagcacg tggaggagtc cagaacagga      960
tgggccggcg gcttcttcgt gagcacccca gctttcagcc aggacgccac atcctactac     1020
aagatctttt ctgacaagga tggctacaag cacatccact acatcaagga taccgtggag     1080
aacgctatcc agatcacaag cggaaagtgg gaggccatct acatcttcag ggtgacccag     1140
gactccctgt tctactcctc taacgagttt gagggctacc caggaaggag aaacatctac     1200
agaatctcca tcggcaacag cccaccctcc aagaagtgcg tgacctgtca cctgcggaag     1260
gagaggtgcc agtactacac agcctctttt agctacaagg ctaagtacta cgctctggtg     1320
tgctacggac caggactgcc tatctctacc ctgcacgacg gacggacaga tcaggagatc     1380
caggtgctgg aggagaacaa gggagctgga aacagcctgc gcaacatcca gctgcccaag     1440
gtggagatca gaagctgaa ggacggcgga ctgacattct ggtacaagat gatcctgcct     1500
ccacagtttg ataggagcaa gaagtacccc ctgctgatcc aggtgtacgg cggaccttgc     1560
tcccagtctg tgaagtccgt gttcgctgtg aactggatca cctacctggc ctctaaggag     1620
ggcatcgtga tcgctctggt ggacggaagg ggaacagctt tccagggcga taagtttctg     1680
cacgccgtgt accgcaagct gggagtgtac gaggtggagg accagctgac cgccgtgcgg     1740
aagttcatcg agatgggctt tatcgatgag gagcgcatcg ctatctgggg atgggcctac     1800
ggcggatacg tgagctccct ggctctggct agcggaacag gactgttcaa gtgtggcatc     1860
gctgtggccc cagtgtctag ctgggagtac tacgcctcta tctacagcga gcggtttatg     1920
ggactgccca ccaaggacga taacctggag cactacaaga acagcacagt gatggctagg     1980
gccgagtact tcagaaacgt ggactacctg ctgatccacg gcaccgctga cgataacgtg     2040
cacttccaga actccgccca gatcgctaag gccctggtga acgctcaggt ggactttcag     2100
gccatgtggt actctgatca gaaccacggc atctcctctg gacgcagcca gaaccacctg     2160
tacacccaca tgacacactt cctgaagcag tgctttagcc tgtccgac                  2208
```

```
<210> SEQ ID NO 10
<211> LENGTH: 736
<212> TYPE: PRT
<213> ORGANISM: Artificial sequence
<220> FEATURE:
<223> OTHER INFORMATION: Native amino acid sequence for mouse FAP

<400> SEQUENCE: 10

Leu Arg Pro Ser Arg Val Tyr Lys Pro Glu Gly Asn Thr Lys Arg Ala
1               5                   10                  15

Leu Thr Leu Lys Asp Ile Leu Asn Gly Thr Phe Ser Tyr Lys Thr Tyr
            20                  25                  30

Phe Pro Asn Trp Ile Ser Glu Gln Glu Tyr Leu His Gln Ser Glu Asp
        35                  40                  45

Asp Asn Ile Val Phe Tyr Asn Ile Glu Thr Arg Glu Ser Tyr Ile Ile
    50                  55                  60

Leu Ser Asn Ser Thr Met Lys Ser Val Asn Ala Thr Asp Tyr Gly Leu
65                  70                  75                  80

Ser Pro Asp Arg Gln Phe Val Tyr Leu Glu Ser Asp Tyr Ser Lys Leu
                85                  90                  95
```

```
Trp Arg Tyr Ser Tyr Thr Ala Thr Tyr Tyr Ile Tyr Asp Leu Gln Asn
        100                 105                 110

Gly Glu Phe Val Arg Gly Tyr Glu Leu Pro Arg Pro Ile Gln Tyr Leu
        115                 120                 125

Cys Trp Ser Pro Val Gly Ser Lys Leu Ala Tyr Val Tyr Gln Asn Asn
        130                 135                 140

Ile Tyr Leu Lys Gln Arg Pro Gly Asp Pro Pro Phe Gln Ile Thr Tyr
145                 150                 155                 160

Thr Gly Arg Glu Asn Arg Ile Phe Asn Gly Ile Pro Asp Trp Val Tyr
                165                 170                 175

Glu Glu Glu Met Leu Ala Thr Lys Tyr Ala Leu Trp Trp Ser Pro Asp
                180                 185                 190

Gly Lys Phe Leu Ala Tyr Val Glu Phe Asn Asp Ser Asp Ile Pro Ile
        195                 200                 205

Ile Ala Tyr Ser Tyr Tyr Gly Asp Gly Gln Tyr Pro Arg Thr Ile Asn
        210                 215                 220

Ile Pro Tyr Pro Lys Ala Gly Ala Lys Asn Pro Val Val Arg Val Phe
225                 230                 235                 240

Ile Val Asp Thr Thr Tyr Pro His His Val Gly Pro Met Glu Val Pro
                245                 250                 255

Val Pro Glu Met Ile Ala Ser Ser Asp Tyr Tyr Phe Ser Trp Leu Thr
                260                 265                 270

Trp Val Ser Ser Glu Arg Val Cys Leu Gln Trp Leu Lys Arg Val Gln
        275                 280                 285

Asn Val Ser Val Leu Ser Ile Cys Asp Phe Arg Glu Asp Trp His Ala
        290                 295                 300

Trp Glu Cys Pro Lys Asn Gln Glu His Val Glu Glu Ser Arg Thr Gly
305                 310                 315                 320

Trp Ala Gly Gly Phe Phe Val Ser Thr Pro Ala Phe Ser Gln Asp Ala
                325                 330                 335

Thr Ser Tyr Tyr Lys Ile Phe Ser Asp Lys Asp Gly Tyr Lys His Ile
        340                 345                 350

His Tyr Ile Lys Asp Thr Val Glu Asn Ala Ile Gln Ile Thr Ser Gly
        355                 360                 365

Lys Trp Glu Ala Ile Tyr Ile Phe Arg Val Thr Gln Asp Ser Leu Phe
        370                 375                 380

Tyr Ser Ser Asn Glu Phe Glu Gly Tyr Pro Gly Arg Arg Asn Ile Tyr
385                 390                 395                 400

Arg Ile Ser Ile Gly Asn Ser Pro Pro Ser Lys Lys Cys Val Thr Cys
                405                 410                 415

His Leu Arg Lys Glu Arg Cys Gln Tyr Tyr Thr Ala Ser Phe Ser Tyr
        420                 425                 430

Lys Ala Lys Tyr Tyr Ala Leu Val Cys Tyr Gly Pro Gly Leu Pro Ile
        435                 440                 445

Ser Thr Leu His Asp Gly Arg Thr Asp Gln Glu Ile Gln Val Leu Glu
        450                 455                 460

Glu Asn Lys Glu Leu Glu Asn Ser Leu Arg Asn Ile Gln Leu Pro Lys
465                 470                 475                 480

Val Glu Ile Lys Lys Leu Lys Asp Gly Gly Leu Thr Phe Trp Tyr Lys
                485                 490                 495

Met Ile Leu Pro Pro Gln Phe Asp Arg Ser Lys Lys Tyr Pro Leu Leu
                500                 505                 510

Ile Gln Val Tyr Gly Gly Pro Cys Ser Gln Ser Val Lys Ser Val Phe
```

-continued

```
                515                 520                 525

Ala Val Asn Trp Ile Thr Tyr Leu Ala Ser Lys Glu Gly Ile Val Ile
    530                 535                 540

Ala Leu Val Asp Gly Arg Gly Thr Ala Phe Gln Gly Asp Lys Phe Leu
545                 550                 555                 560

His Ala Val Tyr Arg Lys Leu Gly Val Tyr Glu Val Glu Asp Gln Leu
                565                 570                 575

Thr Ala Val Arg Lys Phe Ile Glu Met Gly Phe Ile Asp Glu Glu Arg
                580                 585                 590

Ile Ala Ile Trp Gly Trp Ala Tyr Gly Gly Tyr Val Ser Ser Leu Ala
                595                 600                 605

Leu Ala Ser Gly Thr Gly Leu Phe Lys Cys Gly Ile Ala Val Ala Pro
    610                 615                 620

Val Ser Ser Trp Glu Tyr Tyr Ala Ser Ile Tyr Ser Glu Arg Phe Met
625                 630                 635                 640

Gly Leu Pro Thr Lys Asp Asp Asn Leu Glu His Tyr Lys Asn Ser Thr
                645                 650                 655

Val Met Ala Arg Ala Glu Tyr Phe Arg Asn Val Asp Tyr Leu Leu Ile
                660                 665                 670

His Gly Thr Ala Asp Asp Asn Val His Phe Gln Asn Ser Ala Gln Ile
                675                 680                 685

Ala Lys Ala Leu Val Asn Ala Gln Val Asp Phe Gln Ala Met Trp Tyr
    690                 695                 700

Ser Asp Gln Asn His Gly Ile Ser Ser Gly Arg Ser Gln Asn His Leu
705                 710                 715                 720

Tyr Thr His Met Thr His Phe Leu Lys Gln Cys Phe Ser Leu Ser Asp
                725                 730                 735
```

```
<210> SEQ ID NO 11
<211> LENGTH: 2262
<212> TYPE: DNA
<213> ORGANISM: Artificial sequence
<220> FEATURE:
<223> OTHER INFORMATION: nucleotide sequence for native mouse FAP
      operably linked to an IgE leader sequence

<400> SEQUENCE: 11
atggactgga cctggattct gttcctggtg gctgctgcta cacgggtgca ctccctgcgg      60
ccttctcgcg tgtacaagcc agagggcaac accaagcgcg ctctgacact gaaggatatc     120
ctgaacggaa ccttctctta caagacatac tttcccaact ggatctctga gcaggagtac     180
ctgcaccaga gcgaggacga taacatcgtg ttttacaaca tcgagacaag ggagagctac     240
atcatcctga gcaactccac catgaagagc gtgaacgcta cagactacgg cctgtcccct     300
gataggcagt tcgtgtacct ggagtctgac tacagcaagc tgtggagata tcctacacc      360 gccacatact acatctacga tctgcagaac ggcgagtttg tgcggggata cgagctgccc     420
cgccctatcc agtacctgtg ctggagccct gtgggctcca agctggccta cgtgtaccag     480
aacaacatct acctgaagca gaggcccggc gaccctccct tccagatcac ctacacaggc     540
agggagaaca gaatctttaa cggaatcccc gactgggtgt acgaggagga gatgctggct     600
accaagtacg ccctgtggtg gtcccctgat ggcaagttcc tggcttacgt ggagtttaac     660
gactccgata tcccaatcat cgcctactct tactacggcg atggacagta ccccaggaca     720
atcaacatcc ataccccaa ggctggcgcc aagaaccccg tggtgagagt gttcatcgtg     780
gacaccacat acccacacca cgtgggaccc atggaggtgc ctgtgccaga gatgatcgcc     840
```

```
agctccgatt actactttc ttggctgacc tgggtgtcta gcgagagggt gtgcctgcag     900
tggctgaaga gagtgcagaa cgtgtccgtg ctgtctatct gcgacttcag ggaggattgg     960
cacgcttggg agtgtcctaa gaaccaggag cacgtggagg agtccagaac aggatgggcc    1020
ggcggcttct tcgtgagcac cccagctttc agccaggacg ccacatccta ctacaagatc    1080
ttttctgaca aggatggcta caagcacatc cactacatca aggataccgt ggagaacgct    1140
atccagatca caagcggaaa gtgggaggcc atctacatct tcagggtgac ccaggactcc    1200
ctgttctact cctctaacga gtttgagggc tacccaggaa ggagaaacat ctacagaatc    1260
tccatcggca acagcccacc ctccaagaag tgcgtgacct gtcacctgcg gaaggagagg    1320
tgccagtact acacagcctc ttttagctac aaggctaagt actacgctct ggtgtgctac    1380
ggaccaggac tgcctatctc taccctgcac gacggacgga cagatcagga gatccaggtg    1440
ctggaggaga acaaggagct ggagaacagc ctgcgcaaca tccagctgcc caaggtggag    1500
atcaagaagc tgaaggacgg cggactgaca ttctggtaca agatgatcct gcctccacag    1560
tttgatagga gcaagaagta cccctgctg atccaggtgt acggcggacc ttgctcccag    1620
tctgtgaagt ccgtgttcgc tgtgaactgg atcacctacc tggcctctaa ggagggcatc    1680
gtgatcgctc tggtggacgg aaggggaaca gctttccagg gcgataagtt tctgcacgcc    1740
gtgtaccgca gctgggagt gtacgaggtg gaggaccagc tgaccgccgt gcggaagttc    1800
atcgagatgg gctttatcga tgaggagcgc atcgctatct ggggatgggc ctacggcgga    1860
tacgtgagct ccctggctct ggctagcgga acaggactgt tcaagtgtgg catcgctgtg    1920
gccccagtgt ctagctggga gtactacgcc tctatctaca gcgagcggtt tatgggactg    1980
cccaccaagg acgataacct ggagcactac aagaacagca cagtgatggc tagggccgag    2040
tacttcagaa acgtggacta cctgctgatc cacggcaccg ctgacgataa cgtgcacttc    2100
cagaactccg cccagatcgc taaggccctg gtgaacgctc aggtggactt tcaggccatg    2160
tggtactctg atcagaacca cggcatctcc tctggacgca gccagaacca cctgtacacc    2220
cacatgacac acttcctgaa gcagtgcttt agcctgtccg ac                        2262
```

\<210\> SEQ ID NO 12
\<211\> LENGTH: 754
\<212\> TYPE: PRT
\<213\> ORGANISM: Artificial sequence
\<220\> FEATURE:
\<223\> OTHER INFORMATION: amino acid sequence for native mouse FAP
      operably linked to an IgE leader sequence

\<400\> SEQUENCE: 12

```
Met Asp Trp Thr Trp Ile Leu Phe Leu Val Ala Ala Ala Thr Arg Val
1               5                   10                  15

His Ser Leu Arg Pro Ser Arg Val Tyr Lys Pro Glu Gly Asn Thr Lys
            20                  25                  30

Arg Ala Leu Thr Leu Lys Asp Ile Leu Asn Gly Thr Phe Ser Tyr Lys
        35                  40                  45

Thr Tyr Phe Pro Asn Trp Ile Ser Glu Gln Glu Tyr Leu His Gln Ser
    50                  55                  60

Glu Asp Asp Asn Ile Val Phe Tyr Asn Ile Glu Thr Arg Glu Ser Tyr
65                  70                  75                  80

Ile Ile Leu Ser Asn Ser Thr Met Lys Ser Val Asn Ala Thr Asp Tyr
                85                  90                  95

Gly Leu Ser Pro Asp Arg Gln Phe Val Tyr Leu Glu Ser Asp Tyr Ser
```

```
            100              105              110
Lys Leu Trp Arg Tyr Ser Tyr Thr Ala Thr Tyr Tyr Ile Tyr Asp Leu
        115              120              125

Gln Asn Gly Glu Phe Val Arg Gly Tyr Glu Leu Pro Arg Pro Ile Gln
        130              135              140

Tyr Leu Cys Trp Ser Pro Val Gly Ser Lys Leu Ala Tyr Val Tyr Gln
145              150              155              160

Asn Asn Ile Tyr Leu Lys Gln Arg Pro Gly Asp Pro Pro Phe Gln Ile
                165              170              175

Thr Tyr Thr Gly Arg Glu Asn Arg Ile Phe Asn Gly Ile Pro Asp Trp
            180              185              190

Val Tyr Glu Glu Glu Met Leu Ala Thr Lys Tyr Ala Leu Trp Trp Ser
            195              200              205

Pro Asp Gly Lys Phe Leu Ala Tyr Val Glu Phe Asn Asp Ser Asp Ile
        210              215              220

Pro Ile Ile Ala Tyr Ser Tyr Tyr Gly Asp Gly Gln Tyr Pro Arg Thr
225              230              235              240

Ile Asn Ile Pro Tyr Pro Lys Ala Gly Ala Lys Asn Pro Val Val Arg
                245              250              255

Val Phe Ile Val Asp Thr Thr Tyr Pro His His Val Gly Pro Met Glu
            260              265              270

Val Pro Val Pro Glu Met Ile Ala Ser Ser Asp Tyr Tyr Phe Ser Trp
        275              280              285

Leu Thr Trp Val Ser Ser Glu Arg Val Cys Leu Gln Trp Leu Lys Arg
        290              295              300

Val Gln Asn Val Ser Val Leu Ser Ile Cys Asp Phe Arg Glu Asp Trp
305              310              315              320

His Ala Trp Glu Cys Pro Lys Asn Gln Glu His Val Glu Glu Ser Arg
                325              330              335

Thr Gly Trp Ala Gly Gly Phe Phe Val Ser Thr Pro Ala Phe Ser Gln
            340              345              350

Asp Ala Thr Ser Tyr Tyr Lys Ile Phe Ser Asp Lys Asp Gly Tyr Lys
        355              360              365

His Ile His Tyr Ile Lys Asp Thr Val Glu Asn Ala Ile Gln Ile Thr
    370              375              380

Ser Gly Lys Trp Glu Ala Ile Tyr Ile Phe Arg Val Thr Gln Asp Ser
385              390              395              400

Leu Phe Tyr Ser Ser Asn Glu Phe Glu Gly Tyr Pro Gly Arg Arg Asn
                405              410              415

Ile Tyr Arg Ile Ser Ile Gly Asn Ser Pro Pro Ser Lys Lys Cys Val
                420              425              430

Thr Cys His Leu Arg Lys Glu Arg Cys Gln Tyr Tyr Thr Ala Ser Phe
            435              440              445

Ser Tyr Lys Ala Lys Tyr Tyr Ala Leu Val Cys Tyr Gly Pro Gly Leu
        450              455              460

Pro Ile Ser Thr Leu His Asp Gly Arg Thr Asp Gln Glu Ile Gln Val
465              470              475              480

Leu Glu Glu Asn Lys Glu Leu Glu Asn Ser Leu Arg Asn Ile Gln Leu
                485              490              495

Pro Lys Val Glu Ile Lys Lys Leu Lys Asp Gly Gly Leu Thr Phe Trp
            500              505              510

Tyr Lys Met Ile Leu Pro Pro Gln Phe Asp Arg Ser Lys Lys Tyr Pro
        515              520              525
```

-continued

```
Leu Leu Ile Gln Val Tyr Gly Gly Pro Cys Ser Gln Ser Val Lys Ser
    530             535             540

Val Phe Ala Val Asn Trp Ile Thr Tyr Leu Ala Ser Lys Glu Gly Ile
545             550             555             560

Val Ile Ala Leu Val Asp Gly Arg Gly Thr Ala Phe Gln Gly Asp Lys
            565             570             575

Phe Leu His Ala Val Tyr Arg Lys Leu Gly Val Tyr Glu Val Glu Asp
            580             585             590

Gln Leu Thr Ala Val Arg Lys Phe Ile Glu Met Gly Phe Ile Asp Glu
        595             600             605

Glu Arg Ile Ala Ile Trp Gly Trp Ala Tyr Gly Gly Tyr Val Ser Ser
    610             615             620

Leu Ala Leu Ala Ser Gly Thr Gly Leu Phe Lys Cys Gly Ile Ala Val
625             630             635             640

Ala Pro Val Ser Ser Trp Glu Tyr Tyr Ala Ser Ile Tyr Ser Glu Arg
            645             650             655

Phe Met Gly Leu Pro Thr Lys Asp Asp Asn Leu Glu His Tyr Lys Asn
            660             665             670

Ser Thr Val Met Ala Arg Ala Glu Tyr Phe Arg Asn Val Asp Tyr Leu
            675             680             685

Leu Ile His Gly Thr Ala Asp Asp Asn Val His Phe Gln Asn Ser Ala
    690             695             700

Gln Ile Ala Lys Ala Leu Val Asn Ala Gln Val Asp Phe Gln Ala Met
705             710             715             720

Trp Tyr Ser Asp Gln Asn His Gly Ile Ser Ser Gly Arg Ser Gln Asn
            725             730             735

His Leu Tyr Thr His Met Thr His Phe Leu Lys Gln Cys Phe Ser Leu
            740             745             750

Ser Asp
```

<210> SEQ ID NO 13
<211> LENGTH: 15
<212> TYPE: PRT
<213> ORGANISM: Artificial sequence
<220> FEATURE:
<223> OTHER INFORMATION: Immunogenic Fragment of FAP

<400> SEQUENCE: 13

```
Lys Asp Gly Gly Leu Thr Phe Trp Tyr Lys Met Ile Leu Pro Pro
1               5               10              15
```

<210> SEQ ID NO 14
<211> LENGTH: 15
<212> TYPE: PRT
<213> ORGANISM: Artificial sequence
<220> FEATURE:
<223> OTHER INFORMATION: Immunogenic Fragment of FAP

<400> SEQUENCE: 14

```
Ala Val Asn Trp Ile Thr Tyr Leu Ala Ser Lys Glu Gly Ile Val
1               5               10              15
```

<210> SEQ ID NO 15
<211> LENGTH: 15
<212> TYPE: PRT
<213> ORGANISM: Artificial sequence
<220> FEATURE:
<223> OTHER INFORMATION: Immunogenic Fragment of FAP -continued

```
<400> SEQUENCE: 15

Tyr Leu Ala Ser Lys Glu Gly Ile Val Ile Ala Leu Val Asp Gly
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: Immunogenic Fragment of FAP

<400> SEQUENCE: 16

Leu Glu His Tyr Lys Asn Ser Thr Val Met Ala Arg Ala Glu Tyr
1               5                   10                  15

<210> SEQ ID NO 17
<211> LENGTH: 15
<212> TYPE: PRT
<213> ORGANISM: Artificial sequence
<220> FEATURE:
<223> OTHER INFORMATION: Immunogenic Fragment of FAP

<400> SEQUENCE: 17

His Gly Thr Ala Asp Asp Asn Val His Phe Gln Asn Ser Ala Gln
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: Immunogenic Fragment of FAP

<400> SEQUENCE: 18

Val Asp Phe Gln Ala Met Trp Tyr Ser Asp Gln Asn His Gly Ile
1               5                   10                  15

<210> SEQ ID NO 19
<211> LENGTH: 15
<212> TYPE: PRT
<213> ORGANISM: Artificial sequence
<220> FEATURE:
<223> OTHER INFORMATION: Immunogenic Fragment of FAP

<400> SEQUENCE: 19

Asn Ile Glu Thr Arg Glu Ser Tyr Ile Ile Leu Ser Asn Ser Thr
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: Immunogenic Fragment of FAP

<400> SEQUENCE: 20

Gly Leu Ser Pro Asp Arg Gln Phe Val Tyr Leu Glu Ser Asp Tyr
1               5                   10                  15

<210> SEQ ID NO 21
<211> LENGTH: 15
<212> TYPE: PRT
<213> ORGANISM: Artificial sequence
<220> FEATURE:
<223> OTHER INFORMATION: Immunogenic Fragment of FAP

<400> SEQUENCE: 21
```

```
Ala Thr Tyr Tyr Ile Tyr Asp Leu Gln Asn Gly Glu Phe Val Arg
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: Immunogenic Fragment of FAP

<400> SEQUENCE: 22

Glu Val Asp Gly Ile Thr Leu Trp Tyr Lys Met Ile Leu Pro Pro
1               5                   10                  15

<210> SEQ ID NO 23
<211> LENGTH: 15
<212> TYPE: PRT
<213> ORGANISM: Artificial sequence
<220> FEATURE:
<223> OTHER INFORMATION: Immunogenic Fragment of FAP

<400> SEQUENCE: 23

Ala Val Asn Trp Ile Ser Tyr Leu Ala Ser Lys Glu Gly Ile Val
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: Immunogenic Fragment of FAP

<400> SEQUENCE: 24

Asn Ile Glu Thr Gly Glu Ser Tyr Ile Ile Leu Ser Asn Ser Thr
1               5                   10                  15
```

OPTIMIZED SYNTHETIC CONSENSUS IMMUNOGENIC COMPOSITIONS TARGETING FIBROBLAST ACTIVATION PROTEIN

CROSS-REFERENCE TO RELATED APPLICATIONS

This application is a U.S. national phase application filed under 35 U.S.C. § 371 claiming priority to International Patent Application No. PCT/US17/52701, filed Sep. 21, 2017, which is entitled to priority under 35 U.S.C. § 119(e) to U.S. Provisional Patent Application No. 62/397,469, filed Sep. 21, 2016, the contents of each of which are incorporated by reference herein in their entireties.

STATEMENT REGARDING FEDERALLY SPONSORED RESEARCH OR DEVELOPMENT

This invention was made with government support under Grant Nos. P50 CA174523, U19 AI109646 and F32 CA213795 awarded by the National Institutes of Health and Grant No. W31P4Q-15-1-0003 awarded by the U.S. Department of Defense. The government has certain rights in the invention.

TECHNICAL FIELD

The present invention relates to immunogenic compositions targeting Fibroblast Activation Protein, and methods of administering the immunogenic compositions.

BACKGROUND OF THE INVENTION

Solid tumor pathophysiology is characterized by an abnormal microenvironment that guides tumor progression and poses barriers to the efficacy of cancer therapies. Several proteins are overexpressed in the tumor microenvironment, including Fibroblast Activation Protein (FAP). FAP is a membrane-bound enzyme with gelatinase and peptidase activity that is up-regulated in cancer-associated fibroblasts in over 90% of human carcinomas.

Breaking the body's tolerance to the tumor microenvironment has the potential to improve cancer therapy. Previous studies have shown that ablation of FAP-expressing cells from transgenic mice attenuates tumor growth and synergizes with other immune therapies such as immune checkpoint blockade. Groups have additionally shown that T cells expressing chimeric antigen receptors targeting FAP slow tumor progression; however, in some mouse strains these CARs cause lethal toxicity.

Thus, there is a need in the art for the development of safer therapies directed at breaking tolerance to the tumor microenvironment. The present invention satisfies this unmet need.

SUMMARY OF THE INVENTION

In one embodiment the invention relates to an immunogenic composition comprising a nucleic acid molecule, wherein the nucleic acid molecule encodes a peptide comprising an amino acid sequence of a) an amino acid sequence having at least about 90% identity over an entire length of the amino acid sequence of SEQ ID NO:2 or SEQ ID NO:6, b) an immunogenic fragment comprising at least about 90% identity over at least 60% of the amino acid sequence of SEQ ID NO:2 or SEQ ID NO:6, c) the amino acid sequence of SEQ ID NO:2 or SEQ ID NO:6, or d) an immunogenic fragment comprising at least 60% of the amino acid sequence of SEQ ID NO:2 or SEQ ID NO:6.

In one embodiment, the nucleic acid molecule is a DNA molecule. In one embodiment, the nucleic acid molecule is a RNA molecule.

In one embodiment, the nucleic acid molecule comprises a nucleotide sequence of a) a nucleotide sequence having at least about 90% identity over an entire length of a nucleotide sequence of SEQ ID NO:1 or SEQ ID NO:5, b) an immunogenic fragment of a nucleotide sequence having at least about 90% identity over at least 60% of the nucleotide sequence of SEQ ID NO:1 or SEQ ID NO:5, c) a nucleotide sequence of SEQ ID NO:1 or SEQ ID NO:5, or d) an immunogenic fragment of a nucleotide sequence of SEQ ID NO:1 or SEQ ID NO:5.

In one embodiment, the nucleotide sequence encoding the peptide is operably linked to at least one regulatory sequence. In one embodiment, the regulatory sequence is a start codon, an IgE leader sequence, a stop codon or a combination thereof.

In one embodiment, the nucleic acid molecule encodes a peptide comprising an amino acid sequence of a) an amino acid sequence having at least about 90% identity over an entire length of the amino acid sequence of SEQ ID NO:4 or SEQ ID NO:8, b) an immunogenic fragment comprising at least about 90% identity over at least 60% of the amino acid sequence of SEQ ID NO:4 or SEQ ID NO:8, c) the amino acid sequence of SEQ ID NO:4 or SEQ ID NO:8, or d) an immunogenic fragment comprising at least 60% of the amino acid sequence of SEQ ID NO:4 or SEQ ID NO:8.

In one embodiment, the nucleic acid molecule comprises a nucleotide sequence of a) a nucleotide sequence having at least about 90% identity over an entire length of a nucleotide sequence of SEQ ID NO:3 or SEQ ID NO:7, b) an immunogenic fragment of a nucleotide sequence having at least about 90% identity over at least 60% of the nucleotide sequence of SEQ ID NO:3 or SEQ ID NO:7, c) a nucleotide sequence SEQ D NO:3 or SEQ ID NO:7, or d) an immunogenic fragment of a nucleotide sequence of SEQ ID NO:3 or SEQ ID NO:7.

In one embodiment, the nucleic acid molecule is an expression vector. In one embodiment, the nucleic acid molecule is incorporated into a viral particle.

In one embodiment, the immunogenic composition comprises a pharmaceutically acceptable excipient.

In one embodiment, the immunogenic composition comprises an adjuvant.

In one embodiment the invention relates to a nucleic acid molecule encoding a peptide comprising an amino acid sequence of a) an amino acid sequence having at least about 90% identity over an entire length of the amino acid sequence of SEQ ID NO:2 or SEQ ID NO:6, b) a fragment comprising at least about 90% identity over at least 60% of the amino acid sequence of SEQ ID NO:2 or SEQ ID NO:6, c) the amino acid sequence of SEQ ID NO:2 or SEQ ID NO:6, or d) a fragment comprising at least 60% of the amino acid sequence of SEQ ID NO:2 or SEQ ID NO:6.

In one embodiment, the nucleic acid molecule is a DNA molecule or an RNA molecule.

In one embodiment, the nucleic acid molecule is a DNA molecule. In one embodiment, the nucleic acid molecule is a RNA molecule.

In one embodiment, the nucleic acid molecule comprises a nucleotide sequence of a) a nucleotide sequence having at least about 90% identity over an entire length of a nucleotide sequence of SEQ ID NO:1 or SEQ ID NO:5, b) an immunogenic fragment of a nucleotide sequence having at least about 90% identity over at least 60% of the nucleotide sequence of SEQ ID NO:1 or SEQ ID NO:5, c) a nucleotide sequence of SEQ ID NO:1 or SEQ ID NO:5, or d) an immunogenic fragment of a nucleotide sequence of SEQ ID NO:1 or SEQ ID NO:5.

In one embodiment, the nucleotide sequence encoding the peptide is operably linked to at least one regulatory sequence. In one embodiment, the regulatory sequence is a start codon, an IgE leader sequence, a stop codon or a combination thereof.

In one embodiment, the nucleic acid molecule encodes a peptide comprising an amino acid sequence of a) an amino acid sequence having at least about 90% identity over an entire length of the amino acid sequence of SEQ ID NO:4 or SEQ ID NO:8, b) an immunogenic fragment comprising at least about 90% identity over at least 60% of the amino acid sequence of SEQ ID NO:4 or SEQ ID NO:8, c) the amino acid sequence of SEQ ID NO:4 or SEQ ID NO:8, or d) an immunogenic fragment comprising at least 60% of the amino acid sequence of SEQ ID NO:4 or SEQ ID NO:8.

In one embodiment, the nucleic acid molecule comprises a nucleotide sequence of a) a nucleotide sequence having at least about 90% identity over an entire length of a nucleotide sequence of SEQ ID NO:3 or SEQ ID NO:7, b) an immunogenic fragment of a nucleotide sequence having at least about 90% identity over at least 60% of the nucleotide sequence of SEQ ID NO:3 or SEQ ID NO:7, c) a nucleotide sequence SEQ D NO:3 or SEQ ID NO:7, or d) an immunogenic fragment of a nucleotide sequence of SEQ ID NO:3 or SEQ ID NO:7.

In one embodiment, the nucleic acid molecule is an expression vector.

In one embodiment, the nucleic acid molecule is incorporated into a viral particle.

In one embodiment the invention relates to an immunogenic composition comprising a peptide, wherein the peptide comprises an amino acid sequence of a) an amino acid sequence having at least about 90% identity over an entire length of the amino acid sequence of SEQ ID NO:2, SEQ ID NO:4, SEQ ID NO:6 or SEQ ID NO:8, b) an immunogenic fragment comprising at least about 90% identity over at least 60% of the amino acid sequence of SEQ ID NO:2, SEQ ID NO:4, SEQ ID NO:6 or SEQ ID NO:8, c) the amino acid sequence of SEQ ID NO:2, SEQ ID NO:4, SEQ ID NO:6 or SEQ ID NO:8 or d) an immunogenic fragment comprising at least 60% of the amino acid sequence SEQ ID NO:2, SEQ ID NO:4, SEQ ID NO:6 or SEQ ID NO:8.

In one embodiment the invention relates to a peptide comprising an amino acid sequence of a) an amino acid sequence having at least about 90% identity over an entire length of the amino acid sequence of SEQ ID NO:2, SEQ ID NO:4, SEQ ID NO:6 or SEQ ID NO:8, b) an immunogenic fragment comprising at least about 90% identity over at least 60% of the amino acid sequence of SEQ ID NO:2, SEQ ID NO:4, SEQ ID NO:6 or SEQ ID NO:8, c) the amino acid sequence of SEQ ID NO:2, SEQ ID NO:4, SEQ ID NO:6 or SEQ ID NO:8, or d) an immunogenic fragment comprising at least 60% of the amino acid sequence of SEQ ID NO:2, SEQ ID NO:4, SEQ ID NO:6 or SEQ ID NO:8.

In one embodiment the invention relates to a method of inducing an immune response against Fibroblast Activation Protein (FAP) in a subject in need thereof, the method comprising administering an immunogenic composition comprising a nucleic acid molecule, wherein the nucleic acid molecule encodes a peptide comprising an amino acid sequence of a) an amino acid sequence having at least about 90% identity over an entire length of the amino acid sequence of SEQ ID NO:2 or SEQ ID NO:6, b) an immunogenic fragment comprising at least about 90% identity over at least 60% of the amino acid sequence of SEQ ID NO:2 or SEQ ID NO:6, c) the amino acid sequence of SEQ ID NO:2 or SEQ ID NO:6, or d) an immunogenic fragment comprising at least 60% of the amino acid sequence of SEQ ID NO:2 or SEQ ID NO:6 to the subject.

In one embodiment, administering includes at least one of electroporation or injection.

In one embodiment the invention relates to a method of treating or preventing a tumor associated pathology in a subject in need thereof, the method comprising administering an immunogenic composition comprising a nucleic acid molecule, wherein the nucleic acid molecule encodes a peptide comprising an amino acid sequence of a) an amino acid sequence having at least about 90% identity over an entire length of the amino acid sequence of SEQ ID NO:2 or SEQ ID NO:6, b) an immunogenic fragment comprising at least about 90% identity over at least 60% of the amino acid sequence of SEQ ID NO:2 or SEQ ID NO:6, c) the amino acid sequence of SEQ ID NO:2 or SEQ ID NO:6, or d) an immunogenic fragment comprising at least 60% of the amino acid sequence of SEQ ID NO:2 or SEQ ID NO:6 to the subject.

In one embodiment, administering includes at least one of electroporation or injection.

In one embodiment, the tumor associated pathology is at least one of tumor growth, tumor metastasis, or angiogenesis.

In one embodiment, the subject has been diagnosed with cancer.

In one embodiment, cancer is prostate cancer.

In one embodiment, the method comprises administering an immunogenic composition comprising one or more prostate cancer antigens to the subject. In one embodiment, the method comprises administering an immunogenic composition comprising PSMA to the subject.

In one embodiment, the cancer is lung cancer. In one embodiment, the method comprises administering an immunogenic composition comprising one or more lung cancer antigens to the subject. In one embodiment, the method comprises administering an immunogenic composition comprising TERT to the subject.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts a phylogenetic tree describing the genetic relationships between the optimized consensus sequences of the invention and the native human and mouse FAP sequences. FIG. 1B depicts a schematic of the Mouse FAP operably linked to an IgE leader sequence (IgELS) and having a S624A mutation to block dipeptidyl peptidase and gelatinolytic activities. FIG. 1C depicts a diagram of the mature murine FAP in natural homodimeric form, shown in cpk format. The endogenous membrane tether in the fully wild-type FAP is not present in this design. μCon changes relative to representative wild-type sequence are shown in red. One of two ablated active serine residues is visible in yellow located in a monomer active site pocket. FIG. 1D depicts an exemplary western blot showing expression of both native mouse FAP and μCon mouse FAP plasmids transfected into 293T cells. Non-transfected cells, and cells transfected with a GFP-expressing plasmid were used as negative controls.

FIG. 2, comprising FIG. 2A depicts the experimental design. Mice were immunized three times at two-week intervals, and were sacrificed one week follow-ing final vaccination. Splenocytes were analyzed to examine T cell responses. FIG. 2B and FIG. 2C depict exemplary results demonstrating IFN-γ ELISpot responses to native mouse FAP peptides (FIG. 2B) or μCon peptides matched to the vaccine sequence (FIG. 2C). FIG. 2D and FIG. 2E depict exemplary results demonstrating intracellular cytokine staining of CD8+(FIG. 2D) and CD4+(FIG. 2E) T cells following stimulation with native mouse FAP peptides for 5 hours. The 10 μg dose of FAP vaccine was used for this study. Significance was determined by a student's t-test for FIG. 2D and FIG. 2E. *p<0.05, p<0.01, *p<0.001. N=5 mice per group, shown is a representative of two indepen-dent experiments.

FIG. 3, comprising FIG. 3A depicts exemplary results demonstrating the IFN-γ ELISpot responses to native mouse FAP peptides from individual CD-1 outbred mice in naïve control group (top), native mouse FAP vaccine group (middle) or μCon mouse FAP vaccine group (bottom). Immunized mice received 10 μg of DNA plasmid. The immunization schedule for these mice was the same as in FIG. 2. FIG. 3B depicts exemplary results demonstrating the total IFN-γ ELISpot responses from the mice immunized in FIG. 3A, not separated by pool. FIG. 3C depicts exemplary results demonstrating the endpoint bind-ing titers from the mice in FIG. 3A against the native FAP protein (extracellular domain). Significance was determined by two-way ANOVA followed by Tukey's HSD test for FIG. 3B. *p<0.05, p<0.01, *p<0.001. 10 mice were used in the naïve group, and 15 mice each were used in the Native FAP and μCon FAP groups.

FIG. 4, comprising FIG. 4A depicts a diagram showing the experimental setup. C57Bl/6 mice were immunized three times at two-week intervals, and were sacrificed one week following final vaccination. Splenocytes were analyzed to examine T cell responses, and serum was collected to examine antibody responses. FIG. 4B depicts exemplary results demonstrating IFN-γ ELISpot responses to native mouse FAP peptides. FIG. 4C and FIG. 4D depict exemplary results demonstrating intracellular cytokine staining of CD8+(FIG. 4C) and CD4+(FIG. 4D) T cells following stimulation with native mouse FAP peptides for 5 hours. The 10 μg dose of native mouse FAP or μCon mouse FAP vaccine was used for this study. FIG. 4E depicts exemplary results demonstrating endpoint binding titers from the mice in FIG. 4A against the native FAP protein (extracellular domain). Significance was determined by a one-way ANOVA followed by Tukey's HSD test. *p<0.05, p<0.01, *p<0.001. N=4-10 mice per group.

FIG. 5, comprising FIG. 5A depicts a diagram showing the experimental setup. Balb/c mice were immunized three times at two-week intervals, and were sacrificed one week following final vaccination. Splenocytes were analyzed to examine T cell responses, and serum was collected to examine antibody responses. FIG. 5B depicts exemplary results demonstrating IFN-γ ELISpot responses to native mouse FAP peptides. FIG. 5C and FIG. 5D depict exemplary results demonstrating intracellular cytokine staining of CD8+(FIG. 5C) and CD4+(FIG. 5D) T cells following stimulation with native mouse FAP peptides for 5 hours. The 10 μg dose of native mouse FAP or μCon mouse FAP vaccine was used for this study. FIG. 5E depicts exemplary results demonstrating endpoint binding titers from the mice in FIG. 5A against the native FAP protein (extracellular domain). Significance was determined by a one-way ANOVA followed by Tukey's HSD test. *p<0.05, p<0.01, *p<0.001. N=4-10 mice per group.

FIG. 6, comprising FIG. 6A depicts a diagram showing the experimental setup. Mice were implanted with TC-1 cells on day 0, randomized on day 7 and immunized once weekly for a total of 4 immunizations. 10 μg of μCon FAP DNA and 25 μg of μCon mouse TERT DNA was used. FIG. 6B depicts exem-plary results demonstrating tumor volume measurements over time for indicated vaccination regimen for mice implanted with TC-1. FIG. 6C depicts exemplary results demonstrating mouse survival over time for indicated vac-cination regimen for mice implanted with TC-1. Signifi-cance for tumor volume measurements was determined by two-way ANOVA followed by Tukey's HSD test. Signifi-cance for mouse survival was determined by Gehan-Breslow-Wilcoxon test. *p<0.05, p<0.01, *p<0.001, ****p<0.0001. N=10 mice per group for TC-1 study. Shown is a representative of two independent experiments.

FIG. 7, comprising FIG. 7A depicts a diagram showing the experimental setup. Mice were implanted with TRAMP-C2 cells on day 0, randomized on day 4 and immunized once weekly for a total of 4 immunizations. 10 μg of μCon FAP DNA and 20 μg of μCon PSMA was used. FIG. 7B depicts exemplary results demonstrating tumor volume measure-ments over time for indicated vaccination regimen for mice implanted with TRAMP-C2. FIG. 7C depicts exemplary results demonstrating mouse survival over time for indicated vaccination regimen for mice implanted with TRAMP-C2. Significance for tumor volume measurements was deter-mined by two-way ANOVA followed by Tukey's HSD test. Significance for mouse survival was determined by Gehan-Breslow-Wilcoxon test. *p<0.05, p<0.01, *p<0.001, ****p<0.0001. N=15 mice per group for TRAMP-C2 study. Shown is a representative of two independent experiments for each tumor type.

FIG. 9, comprising FIG. 9A depicts a diagram showing the experimental setup. Mice were implanted with TC-1 tumor cells on day 0, randomized on day 7 and immunized once weekly for a total of 2 immunizations. 10 μg of μCon FAP DNA was used. Mice were sacrificed on day 21, and splenocytes and TILs were harvested. FIG. 9B depicts exemplary results demonstrating intracellular cytokine staining of CD8+ T cells in the spleen following stimulation with native mouse FAP peptides for 5 hours. FIG. 9C depicts exemplary results demonstrating intracellular cytokine staining of tumor infiltrating lymphocytes (TILs) that were stimulated with native mouse FAP peptides for 5 hours. FIG. 9D depicts exemplary results demonstrating the frequency of CD8+ T cells and CD4+/CD25+/FoxP3+ Tregs in each tumor, as a percentage of CD45+/CD3+ lymphocytes, assessed by flow cytometry staining. Significance was determined by a student's t-test for panels B-D. *p<0.05, p<0.01, *p<0.001. N=9-10 mice per group, shown is a representative of two independent experiments.

FIG. 10, comprising FIG. 10A and FIG. 10B depict exemplary results demonstrating intracellular cytokine staining of CD8+ TILs following stimulation with native mouse FAP peptides (FIG. 10A) or native mouse TERT peptides (FIG. 10B) for 5 hours. FIG. 10C and FIG. 10D depict exemplary results demonstrating intracellular cytokine staining of CD8+ splenocytes following stimulation with native mouse FAP peptides (FIG. 10C) or native mouse TERT peptides (FIG. 10D) for 5 hours. Significance was determined using a one-way ANOVA followed by Tukey's HSD test. *p<0.05, p<0.01, *p<0.001. N=8-10 mice per group.

FIG. 11, comprising FIG. 11A depicts representative immunohistochemical staining of tissues from control mice or μCon mouse FAP immunized mice for FAP expression. FIG. 11B depicts quantification of the percentage of area in the tumor covered by FAP-expressing cells. FIG. 11C depicts representative immunofluorescent images of tissues from control mice or μCon mouse FAP immunized mice for hyaluronan expression. FIG. 11D depicts quantification of the percentage of area in the tumor covered by hyaluronan. FIG. 11E depicts representative immunofluorescent image of tissues from control mice or μCon mouse FAP immunized mice for F4/80 and EpCAM expression. FIG. 11F depicts quantification of the percentage of area in the tumor covered by F4/80 expressing cells. FIG. 11G depicts representative immunofluorescent image of tissues from control mice or μCon mouse FAP immunized mice for CD8α and EpCAM expression. FIG. 11H depicts quantification of the percentage of area in the tumor covered by CD8α expressing cells. N=6-8 mice per group. Image quantification was performed for at least 5 images per mouse. Significance was determined by a student's t-test for FIG. 11B through FIG. 11D. *p<0.05, p<0.01, *p<0.001. Scale bar=100 μm.

FIG. 12, comprising FIG. 12A through FIG. 12D, depicts exemplary experimental results demonstrating the quantification of the total number of macrophages (FIG. 12A), B cells (FIG. 12B), natural killer cells (FIG. 12C) and dendritic cells (FIG. 12D) per tumor. Significance was determined by a student's t-test. N=9-10 mice per group, shown is a representative of two independent experiments.

FIG. 13, comprising FIG. 13A through FIG. 13D, depicts exemplary experimental results demonstrating the fraction of Arg1+ (FIG. 13A), MHCII+ (FIG. 13B), CD68+ (FIG. 13C), CD80+ (FIG. 13D) and CD86+ (FIG. 13E) macrophages were quantified. Significance was determined by a student's t-test. N=9-10 mice per group, shown is a representative of two independent experiments.

FIG. 14, comprising FIG. 14A through FIG. 14C, depicts characterization of the dominant epitopes for the optimized consensus mouse FAP vaccine. FIG. 14A depicts a matrix map of 122 peptides in native mouse FAP arranged in a matrix of 23 pools. FIG. 14B depicts stimulation of C57Bl/6 mice with each pool of synthetic consensus FAP peptides. FIG. 14C depicts stimulation of Balb/c mice with each pool of synthetic consensus FAP peptides.

FIG. 15 depicts a list of the dominant immunogenic epitopes for the native and synthetic consensus mouse FAP. The dominant immunogenic epitopes of native FAP are provided as SEQ ID NO: 13 through SEQ ID NO: 21. The dominant immunogenic epitopes of the optimized consensus FAP are provided as SEQ ID NO: 15 through SEQ ID NO: 18, and SEQ ID NO: 20 through SEQ ID NO: 24.

DETAILED DESCRIPTION

Figures 1A, 1B, 1C, 1D:
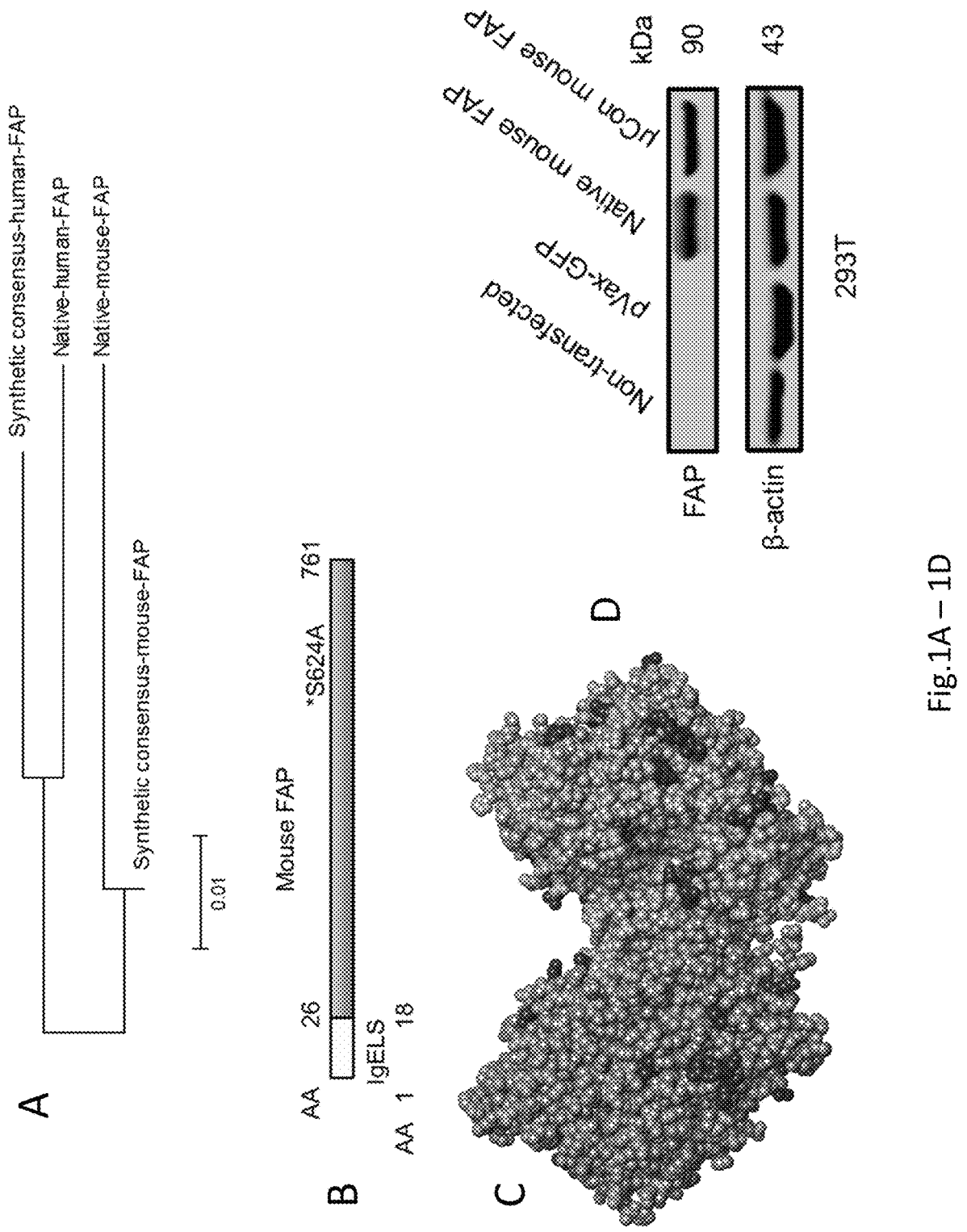
FIG. 1A through FIG. 1D, depicts the design of a FAP immunogenic composition using synthetic consensus technology for use in combination with tumor antigen-specific DNA based immunogenic composition constructs.

In one aspect, the present invention provides an immunogenic composition targeting FAP. Further aspects of the present invention are treatments and/or preventions of cancer growth or metastasis using the disclosed immunogenic composition alone or in combination with additional cancer vaccines or therapeutics.

The sequences encoding the antigens of the invention are genetically diverged from the sequences of their native proteins, and thus, the optimized consensus antigens of the invention are unique. The immunogenic composition of the present invention can be widely applicable to breaking tolerance to the tumor microenvironment, and reducing or preventing tumor growth or metastasis because of the unique sequences of the encoded antigens. These unique sequences allow the immunogenic composition to be universally protective against multiple types of cancer.

The immunogenic composition can be used to protect against and treat any number of cancers. The immunogenic composition can elicit both humoral and cellular immune responses that target the tumor microenvironment antigen. The immunogenic composition can elicit neutralizing antibodies and immunoglobulin G (IgG) antibodies that are reactive with the tumor microenvironment antigen. The immunogenic composition can also elicit a CD8+ T cell response that is reactive to the tumor microenvironment antigen and produce one or more of interferon-gamma (IFN-γ) and tumor necrosis factor alpha (TNF-α). In one embodiment, the immunogenic composition can also elicit a CD4$^+$ T cell response that is reactive to the tumor microenvironment antigen and produce one or more of IFN-γ and TNF-α.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein means any molecule added to the immunogenic composition described herein to enhance the immunogenicity of the antigen.

"Antibody" as used herein means an antibody of classes IgG, IgM, IgA, IgD or IgE, or fragments, fragments or derivatives thereof, including Fab, F(ab')$_2$, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means Watson-Crick (e.g., A-T/U and C-G) or Hoogsteen base pairing between nucleotides or nucleotide analogs of nucleic acid molecules.

"Consensus" or "Consensus Sequence" as used herein may mean a synthetic nucleic acid sequence, or corresponding polypeptide sequence, constructed based on analysis of an alignment of multiple subtypes of a particular antigen. The sequence may be used to induce broad immunity against multiple subtypes, serotypes, or strains of a particular antigen. Synthetic antigens, such as fusion proteins, may be manipulated to generate consensus sequences (or consensus antigens).

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

As used herein, the term "expressible form" refers to gene constructs that contain the necessary regulatory elements operably linked to a coding sequence that encodes a target protein or an immunomodulating protein, such that when present in the cell of the individual, the coding sequence will be expressed.

"Fragment" as used herein means a nucleotide sequence or a portion thereof that encodes a polypeptide capable of eliciting an immune response in a mammal. The fragments can be DNA fragments selected from at least one of the various nucleotide sequences that encode protein fragments set forth below.

"Fragment" or "immunogenic fragment" with respect to polypeptide sequences means a polypeptide capable of eliciting an immune response in a mammal that cross reacts with a full length endogenous antigen. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, or at least 240 amino acids or more of a consensus protein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity.

In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a tumor microenvironment protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Subject" as used herein can mean a mammal that is capable of being administered the immunogenic compositions described herein. The mammal can be, for example, a human, chimpanzee, dog, cat, horse, cow, mouse, or rat.

"Substantially identical" as used herein can mean that a first and second amino acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more amino acids. Substantially identical can also mean that a first nucleotide sequence and a second nucleotide sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides.

"Treatment" or "treating," as used herein can mean protecting of a subject from a disease through means of preventing, suppressing, repressing, or completely eliminating the disease. In one embodiment, preventing the disease involves administering an immunogenic composition of the present invention to a subject prior to onset of the disease. In one embodiment, preventing the disease involves administering an immunogenic composition of the present invention to a subject following a treatment so as to prevent reoccurrence or further progression of the disease. Suppressing the disease involves administering an immunogenic composition of the present invention to a subject after induction of the disease but before its clinical appearance. Repressing the disease involves administering an immunogenic composition of the present invention to a subject after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., 1982, J. Mol. Biol. 157:105-132. The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleotide sequence that is substantially identical over the full length of the full gene sequence or a fragment thereof. The nucleotide sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

DESCRIPTION

The invention provides an optimized consensus sequence of a tumor microenvironment antigen. In one embodiment, the antigen encoded by the optimized consensus sequence is capable of eliciting an immune response in a mammal. In one embodiment, the antigen encoded by the optimized consensus sequence can comprise an epitope(s) that makes it particularly effective as an immunogen against which an immune response can be induced.

The optimized consensus sequence can be a consensus sequence derived from two or more native FAP proteins. The optimized consensus sequence can comprise a consensus sequence and/or modification(s) for improved expression.

Modification can include codon optimization, RNA optimization, addition of a kozak sequence for increased translation initiation, and/or the addition of an immunoglobulin leader sequence to increase immunogenicity. The FAP antigen encoded by the optimized consensus sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized consensus sequence can comprise a hemagglutinin (HA) tag. The FAP antigen encoded by the optimized consensus sequence can be designed to elicit stronger cellular and/or humoral immune responses than a corresponding native antigen. The FAP antigen encoded by the optimized consensus sequence can be designed to break tolerance and synergize with anti-cancer immune therapy.

In one embodiment, an optimized consensus FAP is designed to break tolerance to native human FAP. In one embodiment, a human optimized consensus FAP encoding sequence is as set forth in SEQ ID NO:1 or SEQ ID NO:3. In one embodiment, a human optimized consensus FAP encoded antigen has an amino acid sequence as set forth in SEQ ID NO:2 or SEQ ID NO:4.

In one embodiment, an optimized consensus FAP is designed to break tolerance to native mouse FAP. In one embodiment, a mouse optimized consensus FAP encoding sequence is as set forth in SEQ ID NO:5 or SEQ ID NO:7. In one embodiment, a mouse optimized consensus FAP encoded antigen has an amino acid sequence as set forth in SEQ ID NO:6 or SEQ ID NO:8.

In one embodiment, an optimized consensus encoded FAP antigen is operably linked to one or more regulatory elements. In one embodiment, a regulatory element is a leader sequence. In one embodiment, the optimized consensus DNA sequence operably linked to an IgE leader encoding sequence is set forth in SEQ ID NO:3 or SEQ ID NO:7. In one embodiment, the optimized consensus-encoded FAP antigen operably linked to an IgE leader sequence is as set forth in SEQ ID NO:4 or SEQ ID NO:8.

In one embodiment, a regulatory element is a start codon. Therefore, in one embodiment, the invention relates to a nucleic acid sequence as set forth in SEQ ID NO:1 or SEQ ID NO:5, or a fragment or homolog thereof, operably linked to a nucleotide sequence comprising a start codon at the 5' terminus. In one embodiment, the invention relates to an amino acid sequence as set forth in SEQ ID NO:2 or SEQ ID NO:6, or a fragment or homolog thereof, operably linked to an amino acid encoded by a start codon (e.g., a Methionine) at the N-terminus.

In one embodiment, a regulatory element is at least one stop codon. Therefore, in one embodiment, the invention relates to a nucleic acid sequence as set forth in SEQ ID NO:1, SEQ ID NO:3, SEQ ID NO:5 or SEQ ID NO:7 or a fragment or homolog thereof, operably linked to a nucleotide sequence comprising at least one stop codon at the 3' terminus. In one embodiment, the nucleotide sequence is operably linked to two stop codons to increase the efficiency of translational termination.

In one embodiment, the optimized consensus sequence encoding a FAP antigen can encode a peptide having the amino acid sequence set forth in SEQ ID NO:2, SEQ ID NO:4, SEQ ID NO:6 or SEQ ID NO:8. In one embodiment, the optimized consensus sequence can have the nucleotide sequence set forth in SEQ ID NO:1, SEQ ID NO:3, SEQ ID NO:5 or SEQ ID NO:7. In some embodiments, the sequence can be the nucleotide sequence having at least about 90%, 91%, 92%, 93%, 94%, 95%, 96%, 97%, 98%, 99% or 100% identity over an entire length of the nucleotide sequence set forth in SEQ ID NO:1, SEQ ID NO:3, SEQ ID NO:5 or SEQ ID NO:7. In other embodiments, sequence can be the nucleotide sequence that encodes the amino acid sequence having at least about 90%, 91%, 92%, 93%, 94%, 95%, 96%, 97%, 98%, 99%, or 100% identity over an entire length of the amino acid sequence set forth in SEQ ID NO:2, SEQ ID NO:4, SEQ ID NO:6 or SEQ ID NO:8.

In some embodiments, the optimized consensus FAP antigen can be encoded by an RNA that is a transcript from a DNA sequence having at least about 96%, 97%, 98%, 99% or 100% identity over an entire length of the nucleic acid sequence set forth in the SEQ ID NO:1, SEQ ID NO:3, SEQ ID NO:5 or SEQ ID NO:7. In some embodiments, the optimized consensus FAP antigen can be encoded by an RNA that encodes an amino acid sequence having at least about 96%, 97%, 98%, 99% or 100% identity over an entire length of the amino acid sequence set forth in SEQ ID NO:2, SEQ ID NO:4, SEQ ID NO:6 or SEQ ID NO:8.

The optimized consensus-encoded FAP antigen can be a peptide having the amino acid sequence set forth in SEQ ID NO:2, SEQ ID NO:4, SEQ ID NO:6 or SEQ ID NO:8. In some embodiments, the antigen can have an amino acid sequence having at least about 90%, 91%, 92%, 93%, 94%, 95%, 96%, 97%, 98%, 99%, or 100% identity over an entire length of the amino acid sequence set forth in SEQ ID NO:2, SEQ ID NO:4, SEQ ID NO:6 or SEQ ID NO:8.

Immunogenic fragments of proteins with amino acid sequences homologous to immunogenic fragments of SEQ ID NO:2, SEQ ID NO:4, SEQ ID NO:6 or SEQ ID NO:8, can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:2, SEQ ID NO:4, SEQ ID NO:6 or SEQ ID NO:8. Some embodiments relate to immunogenic fragments that have 96% homology to the immunogenic fragments of consensus protein sequences herein.

Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

In one embodiment, an immunogenic fragment of an optimized consensus FAP antigen encodes at least one immunodominant or sub-immunodominant epitope of a full length optimized consensus FAP antigen. Exemplary immunodominant and sub-immunodominant epitopes of the full length optimized consensus FAP antigen set forth in SEQ ID NO:6 include, but are not limited to, peptides having an amino acid sequence as set forth in SEQ ID NO:15, SEQ ID NO:16, SEQ ID NO:17, SEQ ID NO:18, SEQ ID NO:20, SEQ ID NO:21, SEQ ID NO:22, SEQ ID NO:23, and SEQ ID NO:24.

Some embodiments relate to immunogenic fragments of SEQ ID NO:1, SEQ ID NO:3, SEQ ID NO:5 or SEQ ID NO:7 comprising at least 60%, at least 65%, at least 70%, at least 75%, at least 80%, at least 85%, at least 90%, at least 95%, at least 96%, at least 97%, at least 98% or at least 99% of the full length of SEQ ID NO:1, SEQ ID NO:3, SEQ ID NO:5 or SEQ ID NO:7. Immunogenic fragments can be at least 96%, at least 97% at least 98% or at least 99% homologous to fragments of SEQ ID NO:1, SEQ ID NO:3, SEQ ID NO:5 or SEQ ID NO:7. In some embodiments, immunogenic fragments include sequences that encode a leader sequence, such as for example an immunoglobulin leader, such as the IgE leader. In some embodiments, fragments are free of coding sequences that encode a leader sequence.

Immunogenic Composition

Provided herein are immunogenic compositions, such as vaccines, comprising an optimized consensus sequence, an optimized consensus-encoded antigen, a fragment thereof, a variant thereof, or a combination thereof. The immunogenic composition can be used to reduce tumor growth or metastasis or protect against tumor development, thereby treating, preventing, and/or protecting against cancer based pathologies. The immunogenic composition can significantly induce an immune response of a subject administered with the immunogenic composition, thereby protecting against and treating cancer based pathologies in the subject.

The immunogenic composition can be a DNA vaccine, a peptide vaccine, or a combination DNA and peptide vaccine. The DNA vaccine can include an optimized consensus nucleotide sequence encoding an antigen. The nucleotide sequence can be DNA, RNA, cDNA, a variant thereof, a fragment thereof, or a combination thereof. The nucleotide sequence can also include additional sequences that encode linker, leader, or tag sequences that are linked to the antigen by a peptide bond. The peptide vaccine can include an antigen, a variant thereof, a fragment thereof, or a combination thereof. The combination DNA and peptide vaccine can include the above described optimized consensus nucleotide sequence and the encoded antigen.

In one embodiment, immunogenic composition of the invention can be used to elicit protective anti-tumor immunity against, and prevent recurrence of, cancers characterized by tumor cells expressing FAP, e.g., cancer cells and metastatic tumor lesions.

In one embodiment, the compositions and methods described herein are useful for treatment of cancer and tumor cells, i.e., both malignant and benign tumors, so long as the cells to be treated express FAP. Thus, in various embodiments of the methods and compositions described herein, the cancer can include, without limitation, prostate cancer, lung carcinomas, non-small cell lung carcinoma, malignant sarcoma, breast cancer, pancreatic cancer, melanoma, blood cancers (e.g., leukemia, lymphoma, myeloma), esophageal squamous cell carcinomas, bladder cancer, colorectal cancer, esophagus, gastric cancer, hepatocarcinoma, head and neck cancer, brain cancer, anal cancer, synovial carcinoma, testicular cancer, liver cancer, cervical cancer, recurrent respiratory papillomatosis, skin cancer and stomach cancer.

In one embodiment, an immunogenic composition of the invention comprises a FAP antigen. In one embodiment, an immunogenic composition of the invention comprises a FAP antigen and one or more additional cancer antigens.

In one embodiment, the immunogenic composition can be a vaccine. The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510, 245; 4,797,368; 4,722,848; 4,790,987; 4,920,209; 5,017, 487; 5,077,044; 5,110,587; 5,112,749; 5,174,993; 5,223, 424; 5,225,336; 5,240,703; 5,242,829; 5,294,441; 5,294, 548; 5,310,668; 5,387,744; 5,389,368; 5,424,065; 5,451, 499; 5,453,364; 5,462,734; 5,470,734; 5,474,935; 5,482, 713; 5,591,439; 5,643,579; 5,650,309; 5,698,202; 5,955, 088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose.

Combinational Immunogenic Compositions for Treating Particular Cancers

Figure 6A:
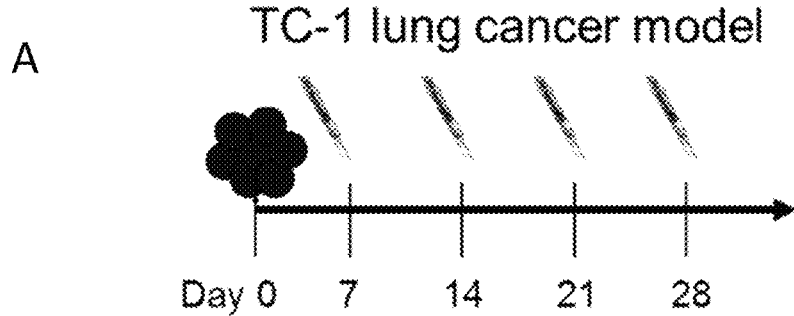
FIG. 6A through FIG. 6C, depicts experimental results demonstrating the efficacy of FAP vaccine and combination therapy in therapeutic lung tumor model.

The immunogenic composition can be in the form of various combinations of the antigens as described above with one or more cancer antigens to treat particular cancers or tumors. Depending upon the combination of one or more cancer antigens, various cancers or other tumor types may be targeted with the immunogenic composition. These cancers can include, but are not limited to prostate cancer, lung carcinomas, non-small cell lung carcinoma, malignant sarcoma, breast cancer, ovarian cancer, pancreatic cancer, melanoma, blood cancers (e.g., leukemia, lymphoma, myeloma), esophageal squamous cell carcinomas, bladder cancer, colorectal cancer, esophagus, gastric cancer, hepatocarcinoma, head and neck cancer, brain cancer, anal cancer, synovial carcinoma, testicular cancer, liver cancer, cervical cancer, recurrent respiratory papillomatosis, skin cancer and stomach cancer. FIG. 6 and FIG. 7 provide examples of particular combinations of optimized consensus antigens and tumor antigens that may be used to treat particular cancers.

Cancer Antigens

The immunogenic composition can comprise one or more cancer antigens such as WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase 3 (PR1), Bcr-abl, Tyrosinase, Survivin, PSA, hTERT, EphA2, PAP, ML-IAP, AFP, EpCAM, ERG, NA17, PAX3, ALK, Androgen Receptor, Cyclin B1, Polysialic Acid, MYCN, TRP-2, RhoC, GD3, Fucosyl GM1, Mesothelin, PSCA, MAGE A1, sLe(a), CYP1B1, PLAC1, GM3 ganglioside, BORIS, Tn, GloboH, ETV6-AML, NY-BR-1, RGSS, SART3, STn, Carbonic anhydrase IX, PAXS, OY-TES1, Sperm Protein 17, LCK, HMWMAA, Sperm fibrous sheath proteins, AKAP-4, SSX2, XAGE 1, B7H3, Legumain, Tie 2, Page4, VEGFR2, MAD-CT-1 (protamine 2), MAD-CT-2, and FOS-related antigen 1 to treat or prevent a tumor associated pathology. The immunogenic composition can further combine one or more cancer antigens WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase 3 (PR1), Bcr-abl, Tyrosinase, Survivin, PSA, hTERT, EphA2, PAP, ML-IAP, AFP, EpCAM, ERG, NA17, PAX3, ALK, Androgen Receptor, Cyclin B1, Polysialic Acid, MYCN, TRP-2, RhoC, GD3, Fucosyl GM1, Mesothelin, PSCA, MAGE A1, sLe(a), CYP1B1, PLAC1, GM3 ganglioside, BORIS, Tn, GloboH, ETV6-AML, NY-BR-1, RGSS, SART3, STn, Carbonic anhydrase IX, PAXS, OY-TES1, Sperm Protein 17, LCK, HMWMAA, Sperm fibrous sheath proteins, AKAP-4, SSX2, XAGE 1, B7H3, Legumain, Tie 2, Page4, VEGFR2, MAD-CT-1 (protamine 2), MAD-CT-2, and FOS-related antigen 1 with an optimized consensus FAP antigen for treating or preventing a tumor associated pathology. Other combinations of cancer antigens may also be applied for treating or preventing a tumor associated pathology.

Prostate Cancer Antigens

The immunogenic composition can comprise one or more cancer antigens such as PSA, PSMA, or STEAP to treat or prevent prostate cancer (see FIG. 12). The immunogenic composition can further combine one or more cancer antigens PSA, PSMA, or STEAP with a FAP antigen for treating or preventing prostate cancer. Other combinations of cancer antigens may also be applied for treating or preventing prostate cancer. Exemplary PSA, PSMA, and STEP antigens, as well as nucleic acid molecules encoding such antigens, are disclosed in PCT application no. PCT/US11/60592 and corresponding U.S. Pat. No. 8,927,692, which are incorporated herein by reference.

Lung Cancer Antigens

Figures 13A, 13B, 13C, 13D, 13E:
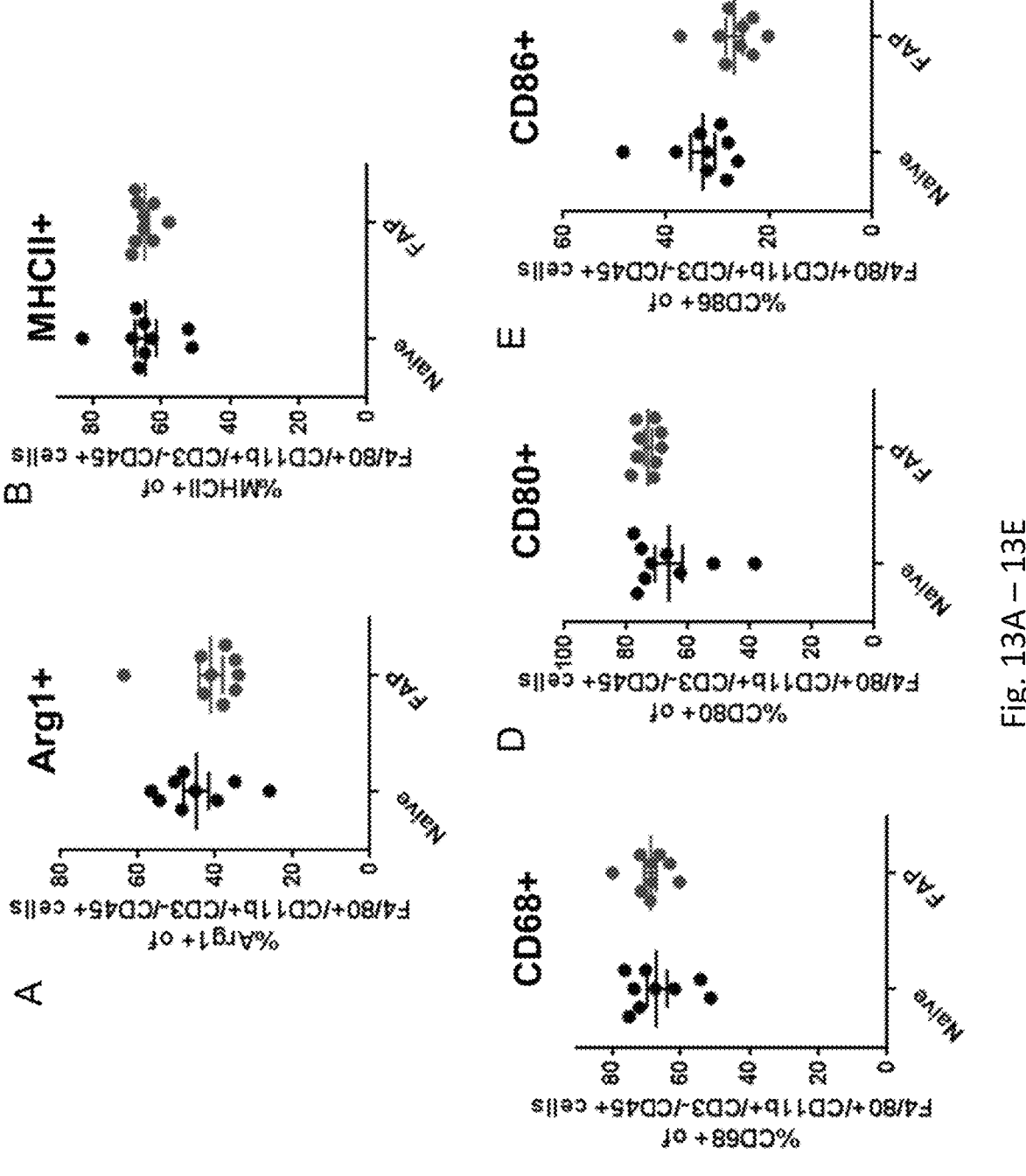
FIG. 13A through FIG. 13E, depicts experimental results demonstrating the impact of μCon FAP vaccine on properties of tumor infiltrating macrophages. Mice were implanted with TC-1 tumor cells and immunized according to the schedule in FIG. 9A. Tumors were harvested for surface staining of innate immune cell populations, according to the markers indicated in figure legend.

The immunogenic composition can comprise one or more cancer antigens such as TERT, CD22, MAGE-3 and NY-ESO-1 to treat or prevent lung cancer (see FIG. 13). The immunogenic composition can further combine one or more cancer antigens TERT, CD22, MAGE-3 and NY-ESO-1 with a FAP antigen for treating or preventing lung cancer. Other combinations of cancer antigens may also be applied for treating or preventing lung cancer.

Breast Cancer Antigens

The immunogenic composition can comprise one or more cancer antigens such as HER2, MUC-1, CEA, MAGE-3 and NY-ESO-1 to treat or prevent breast cancer. The immunogenic composition can further combine one or more cancer antigens HER2, MUC-1, CEA, MAGE-3 and NY-ESO-1 with a FAP antigen for treating or preventing breast cancer. Other combinations of cancer antigens may also be applied for treating or preventing breast cancer.

Pancreatic Cancer Antigens

The immunogenic composition can comprise one or more cancer antigens such as MUC-1, CEA, HER2, Mesothelin, Survivin, and VEGFR2 to treat or prevent pancreatic cancer. The immunogenic composition can further combine one or more cancer antigens MUC-1, CEA, HER2, Mesothelin, Survivin, and VEGFR2 with a FAP antigen for treating or preventing pancreatic cancer. Other combinations of cancer antigens may also be applied for treating or preventing pancreatic cancer.

Melanoma Antigens

The immunogenic composition can comprise one or more cancer antigens such as tyrosinase, PRAME, or GP100-Trp2 to treat or prevent melanoma. The immunogenic composition can further combine one or more cancer antigen tyrosinase, PRAME, or GP100-Trp2 with a FAP antigen for treating or preventing melanoma. Other combinations of cancer antigens may also be applied for treating or preventing melanoma.

Liver Cancer Antigens

The immunogenic composition can comprise one or more cancer antigens such as HBV core antigen, HBV surface antigen, HCVNS34A, HCVNSSA, HCV NS5B, or HCVNS4B to treat or prevent liver cancer. The immunogenic composition can further combine one or more cancer antigens HBV core antigen, HBV surface antigen, HCVNS34A, HCVNSSA, HCV NS5B, or HCVNS4B with a FAP antigen for treating or preventing liver cancer. Other combinations of cancer antigens may also be applied for treating or preventing liver cancer.

Glioblastoma Antigens

The immunogenic composition can comprise CMV to treat or prevent glioblastoma. The immunogenic composition can further combine CMV with a FAP antigen for treating or preventing glioblastoma. Other combinations of cancer antigens may also be applied for treating or preventing glioblastoma.

Blood Cancer Antigens (e.g., Leukemia, Lymphoma, Myeloma)

The immunogenic composition can comprise one or more cancer antigens such as PRAME, WT-1, hTERT to treat or prevent blood cancers such as leukemia, lymphoma and myeloma. The immunogenic composition can further combine one or more cancer antigens PRAME, WT-1, hTERT with a FAP antigen blood cancers such as leukemia, lymphoma and myeloma. Other combinations of cancer antigens may also be applied for treating or preventing blood cancers such as leukemia, lymphoma and myeloma cancer.

Immune Response

The immunogenic composition can induce an immune response in the subject administered the composition. The induced immune response can be specific for a native antigen. The induced immune response can be reactive with a native antigen related to the optimized consensus-encoded antigen. In various embodiments, related antigens include antigens having amino acid sequences having at least 90%, at least 91%, at least 92%, at least 93%, at least 94%, at least 95%, at least 96%, at least 97%, at least 98%, at least 99%, or 100% homology to the amino acid sequence of the optimized consensus-encoded antigen. In various embodiments, related antigens include antigens encoded by nucleotide sequences having at least 90%, at least 91%, at least 92%, at least 93%, at least 94%, at least 95%, at least 96%, at least 97%, at least 98%, at least 99%, or 100% homology to the optimized consensus nucleotide sequences disclosed herein.

The immunogenic composition can induce a humoral immune response in the subject administered the immunogenic composition. The induced humoral immune response can be specific for a native antigen. The induced humoral immune response can be reactive with the native antigen related to the optimized consensus-encoded antigen. The humoral immune response can be induced in the subject administered the immunogenic composition by about 1.5-fold to about 16-fold, about 2-fold to about 12-fold, or about 3-fold to about 10-fold. The humoral immune response can be induced in the subject administered the immunogenic composition by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized FAP antigen.

The humoral immune response induced by the immunogenic composition can include an increased level of neutralizing antibodies associated with the subject administered the immunogenic composition as compared to a subject not administered the immunogenic composition. The neutralizing antibodies can be specific for a native antigen related to the optimized consensus-encoded antigen. The neutralizing antibodies can be reactive with the native antigen genetically related to the optimized consensus antigen. The neutralizing antibodies can provide protection against and/or treatment of tumor growth, metastasis or tumor associated pathologies in the subject administered the immunogenic composition.

The humoral immune response induced by the immunogenic composition can include an increased level of IgG antibodies associated with the subject administered the immunogenic composition as compared to a subject not administered the immunogenic composition. These IgG antibodies can be specific for the native antigen genetically related to the optimized consensus antigen. These IgG antibodies can be reactive with the native antigen genetically related to the optimized consensus antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized FAP antigen.

The immunogenic composition can induce a cellular immune response in the subject administered the immunogenic composition. The induced cellular immune response can be specific for a native antigen related to the optimized consensus-encoded antigen. The induced cellular immune response can be reactive to the native antigen related to the optimized consensus-encoded antigen. The induced cellular immune response can include eliciting a CD8$^+$ T cell response. The elicited CD8$^+$ T cell response can be reactive with the native antigen genetically related to the optimized consensus antigen. The elicited CD8$^+$ T cell response can be polyfunctional. The induced cellular immune response can include eliciting a CD8$^+$ T cell response, in which the CD8$^+$ T cells produce interferon-gamma (IFN-$\gamma$), tumor necrosis factor alpha (TNF-$\alpha$), interleukin-2 (IL-2), or a combination of IFN-$\gamma$ and TNF-$\alpha$.

The induced cellular immune response can include an increased CD8$^+$ T cell response associated with the subject administered the immunogenic composition as compared to the subject not administered the immunogenic composition. The CD8$^+$ T cell response associated with the subject administered the immunogenic composition can be increased by about 2-fold to about 30-fold, about 3-fold to about 25-fold, or about 4-fold to about 20-fold as compared to the subject not administered the immunogenic composition. The CD8⁺ T cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition or a subject administered a non-optimized FAP antigen.

The induced cellular immune response can include an increased frequency of CD107a/IFNγ/T-bet triple-positive CD8 T cells that are reactive against the native antigen. The frequency of CD107a/IFNγ/T-bet triple-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized FAP antigen.

The induced cellular immune response can include an increased frequency of CD107a/IFNγ double-positive CD8 T cells that are reactive against the native antigen. The frequency of CD107a/IFNγ double-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic composition or a subject administered a non-optimized FAP antigen.

The cellular immune response induced by the immunogenic composition can include eliciting a CD4⁺ T cell response. The elicited CD4⁺ T cell response can be reactive with the native antigen genetically related to the optimized consensus antigen. The elicited CD4⁺ T cell response can be polyfunctional. The induced cellular immune response can include eliciting a CD4⁺ T cell response, in which the CD4⁺ T cells produce IFN-γ, TNF-α, IL-2, or a combination of IFN-γ and TNF-α.

The induced cellular immune response can include an increased frequency of CD4⁺ T cells that produce IFN-γ. The frequency of CD4⁺IFN-γ⁺ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized FAP antigen.

The induced cellular immune response can include an increased frequency of CD4⁺ T cells that produce TNF-α. The frequency of CD4⁺ TNF-α⁺ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic composition or a subject administered a non-optimized FAP antigen.

The induced cellular immune response can include an increased frequency of CD4⁺ T cells that produce both IFN-γ and TNF-α. The frequency of CD4⁺IFN-γ⁺ TNF-α⁺ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic composition or a subject administered a non-optimized FAP antigen.

The immunogenic composition of the present invention can have features required of effective vaccines such as being safe so the vaccine itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The immunogenic composition can further induce an immune response when administered to different tissues such as the muscle or skin. The immunogenic composition can further induce an immune response when administered via electroporation, or injection, or subcutaneously, or intramuscularly.

Fragments

In one embodiment, the immunogenic fragment is an immunogenic fragment of a full length antigen of the invention. As used herein, an immunogenic fragment is a fragment of a full length nucleic acid or amino acid sequence that can induce an immune response significantly similar to that of the full length sequence. In one embodiment, an immunogenic fragment comprises an immunogenic epitope of a full length sequence. In one embodiment, the immunogenic fragment induces an immune response at least about 0.7-fold, at least about 0.8-fold, at least about 0.9-fold, at least about 1.0-fold, at least about 1.1-fold, at least about 1.2-fold, at least about 1.3-fold, at least about 1.4-fold, at least about 1.5-fold, at least about 2.0-fold or greater than 2.0-fold as compared to the full length sequence.

The immunogenic fragment can induce a humoral immune response in the subject administered the immunogenic fragment. The humoral immune response can be induced in the subject administered the immunogenic fragment by about 1.5-fold to about 16-fold, about 2-fold to about 12-fold, or about 3-fold to about 10-fold. The humoral immune response can be induced in the subject administered the immunogenic fragment by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered immunogenic fragment.

The humoral immune response induced by the immunogenic fragment can include an increased level of IgG antibodies associated with the subject administered the immunogenic fragment as compared to a subject not administered the immunogenic fragment. The level of IgG antibody associated with the subject administered the immunogenic fragment can be increased by about 1.5-fold to about 16-fold, about 2-fold to about 12-fold, or about 3-fold to about 10-fold as compared to the subject not administered the immunogenic fragment. The level of IgG antibody associated with the subject administered the immunogenic fragment can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic fragment.

The immunogenic fragment can induce a cellular immune response in the subject administered the immunogenic fragment. The induced cellular immune response can be specific for a native antigen related to the optimized consensus-encoded antigen. The induced cellular immune response can be reactive to the native antigen related to the optimized consensus-encoded antigen. The induced cellular immune response can include eliciting a CD8$^+$ T cell response. The elicited CD8$^+$ T cell response can be reactive with the native antigen genetically related to the optimized consensus antigen. The elicited CD8$^+$ T cell response can be polyfunctional. The induced cellular immune response can include eliciting a CD8$^+$ T cell response, in which the CD8$^+$ T cells produce interferon-gamma (IFN-$\gamma$), tumor necrosis factor alpha (TNF-$\alpha$), interleukin-2 (IL-2), or a combination of IFN-$\gamma$ and TNF-$\alpha$.

The induced cellular immune response can include an increased CD8$^+$ T cell response associated with the subject administered the immunogenic fragment as compared to the subject not administered the immunogenic fragment. The CD8$^+$ T cell response associated with the subject administered the immunogenic fragment can be increased by about 2-fold to about 30-fold, about 3-fold to about 25-fold, or about 4-fold to about 20-fold as compared to the subject not administered the immunogenic fragment. The CD8$^+$ T cell response associated with the subject administered the immunogenic fragment can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic fragment.

The induced cellular immune response can include an increased frequency of CD107a/IFN$\gamma$/T-bet triple-positive CD8 T cells that are reactive against the native antigen. The frequency of CD107a/IFN$\gamma$/T-bet triple-positive CD8 T cells associated with the subject administered the immunogenic fragment can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic fragment.

The induced cellular immune response can include an increased frequency of CD107a/IFN$\gamma$ double-positive CD8 T cells that are reactive against the native antigen. The frequency of CD107a/IFN$\gamma$ double-positive CD8 T cells associated with the subject administered the immunogenic fragment can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic.

The cellular immune response induced by the immunogenic fragment can include eliciting a CD4$^+$ T cell response. The elicited CD4$^+$ T cell response can be reactive with the native antigen genetically related to the optimized consensus antigen. The elicited CD4$^+$ T cell response can be polyfunctional. The induced cellular immune response can include eliciting a CD4$^+$ T cell response, in which the CD4$^+$ T cells produce IFN-$\gamma$, TNF-$\alpha$, IL-2, or a combination of IFN-$\gamma$ and TNF-$\alpha$.

The induced cellular immune response can include an increased frequency of CD4$^+$ T cells that produce IFN-$\gamma$. The frequency of CD4$^+$IFN-$\gamma^+$ T cells associated with the subject administered the immunogenic fragment can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic fragment.

The induced cellular immune response can include an increased frequency of CD4$^+$ T cells that produce TNF-$\alpha$. The frequency of CD4$^+$ TNF-$\alpha^+$ T cells associated with the subject administered the immunogenic fragment can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic fragment.

The induced cellular immune response can include an increased frequency of CD4$^+$ T cells that produce both IFN-$\gamma$ and TNF-$\alpha$. The frequency of CD4$^+$IFN-$\gamma^+$ TNF-$\alpha^+$ associated with the subject administered the immunogenic fragment can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic fragment.

The immunogenic fragment of the present invention can have features required of effective vaccines such as being safe so the vaccine itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The immunogenic fragment can further induce an immune response when administered to different tissues such as the muscle or skin. The immunogenic fragment can further induce an immune response when administered via electroporation, or injection, or subcutaneously, or intramuscularly.

Vector

The immunogenic composition can comprise one or more vectors that include an optimized consensus nucleotide encoding the antigen. The one or more vectors can be capable of expressing the antigen. The vector can have a nucleotide sequence containing an origin of replication. The vector can be a plasmid, bacteriophage, bacterial artificial chromosome or yeast artificial chromosome. The vector can be either a self-replicating extrachromosomal vector or a vector which integrates into a host genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

(2) RNA Vectors

In one embodiment, the nucleic acid is an RNA molecule. Accordingly, in one embodiment, the invention provides an RNA molecule encoding one or more MAYV antigens. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

(3) Circular and Linear Vectors

The vector may be a circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid immunogenic composition, or linear expression cassette ("LEC"), that is capable of being efficiently delivered to a subject via electroporation and expressing one or more desired antigens.

The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleotide sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system.

The LEC can be perM2. The LEC can be perNP. perNP and perMR can be derived from pNP (Puerto Rico/34) and pM2 (New Caledonia/99), respectively.

(4) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleotide sequence encoding the antigen and signals required for efficient polyadenylation of the transcript, ribosome binding sites, and translation termination. The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

Multiple Vectors

The immunogenic composition may comprise a plurality of copies of a single nucleic acid molecule such a single plasmid, or a plurality of copies of two or more different nucleic acid molecules such as two or more different plasmids. For example an immunogenic composition may comprise plurality of two, three, four, five, six, seven, eight, nine or ten or more different nucleic acid molecules. Such compositions may comprise plurality of two, three, four, five, six, or more different plasmids.

Immunogenic compositions may comprise nucleic acid molecules, such as plasmids, that collectively contain coding sequence for a single antigen. In one embodiment, the antigen is FAP. Immunogenic compositions may comprise nucleic acid molecules, such as plasmids, that collectively contain coding sequence for multiple antigens. In one embodiment, the antigens are multiple antigens selected from FAP and an additional cancer antigen. In one exemplary embodiment, the antigens are FAP and TERT. In another exemplary embodiment, the antigens are FAP and PSMA. Immunogenic compositions may comprise nucleic acid molecules, such as plasmids, that collectively contain coding sequence for one or more antigen and one or more cancer antigen.

Excipients and Other Components of the Immunogenic Composition

The immunogenic composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the immunogenic composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid-based immunogenic compositions may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the immunogenic composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more adjuvants. An adjuvant may be other genes that are expressed from the same or from an alternative plasmid or are delivered as proteins in combination with the plasmid above in the immunogenic composition. The one or more adjuvants may be proteins and/or nucleic acid molecules that encode proteins selected from the group consisting of: CCL20, α-interferon (IFN-α), (3-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-18, IL-23, IL-28, MHC, CD80, CD86, IL-1, IL-2, IL-4, IL-5, IL-6, IL-10, IL-18, MCP-1, MIP-1α, MIP-1μ, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothe- lial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL- recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof, or a combination thereof. In some embodiments adjuvant may be one or more proteins and/or nucleic acid molecules that encode proteins selected from the group consisting of: RANTES, IL-12, IL-15, IL-23, IL-28, CTACK, TECK, MEC, OX40 and DR5. Examples of IL-12 constructs and sequences are disclosed in PCT appli- cation no. PCT/US12/69017 and corresponding U.S. Pat. No. 9,272,024, which are incorporated herein by reference. Examples of IL-15 constructs and sequences are disclosed in PCT application no. PCT/US04/18962 and corresponding U.S. Pat. No. 8,173,786, which are each incorporated herein by reference. Examples of IL-23 constructs and sequences are disclosed in PCT application no. PCT/US14/25348 and corresponding U.S. application Ser. No. 14/775,087, which are each incorporated herein by reference. Examples of IL-28 constructs and sequences are disclosed in PCT appli- cation no. PCT/US09/039648 and corresponding U.S. appli- cation Ser. No. 12/936,192, which are each incorporated herein by reference. Examples of IL-28 constructs and sequences are disclosed in PCT application no. PCT/US09/ 039648 and corresponding U.S. application Ser. No. 12/936, 192, which are each incorporated herein by reference. Examples of RANTES and other constructs and sequences are disclosed in PCT application no. PCT/US1999/004332 and corresponding U.S. Pat. No. 8,119,395, which are each incorporated herein by reference. Other examples of RANTES constructs and sequences are disclosed in PCT application no. PCT/US11/024098 and corresponding U.S. Pat. No. 9,034,313, which are incorporated herein by refer- ence. Examples of chemokines CTACK, TECK and MEC constructs and sequences are disclosed in PCT application no. PCT/US2005/042231 and corresponding U.S. applica- tion Ser. No. 11/719,646, which are each incorporated herein by reference. Examples of OX40 and other immunomodu- lators are disclosed in U.S. application Ser. No. 10/560,653, which is incorporated herein by reference. Examples of DR5 and other immunomodulators are disclosed in U.S. applica- tion Ser. No. 09/622,452, which is incorporated herein by reference.

The immunogenic composition may comprise the con- sensus antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical composi- tions contain about 10 nanograms to about 800 micrograms of DNA. In some preferred embodiments, the pharmaceu- tical compositions contain about 0.1 to about 500 micro- grams of DNA. In some preferred embodiments, the phar- maceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 micro- gram to about 10 milligrams; from about 0.1 microgram to about 10 milligrams; from about 1 milligram to about 2 milligram, from about 5 nanogram to about 1000 micro- grams, from about 10 nanograms to about 800 micrograms, from about 0.1 to about 500 micrograms, from about 1 to about 350 micrograms, from about 25 to about 250 micro- grams, from about 100 to about 200 microgram of the consensus antigen or plasmid thereof.

In some embodiments, pharmaceutical compositions according to the present invention comprise at least 10, 15, 20, 25, 30, 35, 40, 45, 50, 55, 60, 65, 70, 75, 80, 85, 90, 95 or 100 nanograms of nucleic acid of the vaccine. In some embodiments, the pharmaceutical compositions can com- prise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 or 1000 micrograms of nucleic acid of the vaccine. In some embodi- ments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of nucleic acid of the vaccine.

In other embodiments, the pharmaceutical composition can comprise up to and including 15, 20, 25, 30, 35, 40, 45, 50, 55, 60, 65, 70, 75, 80, 85, 90, 95 or 100 nanograms of nucleic acid of the vaccine. In some embodiments, the pharmaceutical composition can comprise up to and includ- ing 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 micrograms of nucleic acid of the vaccine. In some embodiments, the pharmaceutical composition can comprise up to and includ- ing 1.5, 2, 2.5, 3, 3.5, 4, 4.5, 5, 5.5, 6, 6.5, 7, 7.5, 8, 8.5, 9, 9.5 or 10 mg of nucleic acid of the vaccine.

The immunogenic composition may be formulated according to the mode of administration to be used. An injectable vaccine pharmaceutical composition may be ster- ile, pyrogen free and particulate free. An isotonic formula- tion or solution may be used. Additives for isotonicity may include sodium chloride, dextrose, mannitol, sorbitol, and lactose. The vaccine may comprise a vasoconstriction agent.

The isotonic solutions may include phosphate buffered saline. An immunogenic composition may further comprise stabilizers including gelatin and albumin. The stabilizing may allow the formulation to be stable at room or ambient temperature for extended periods of time such as LGS or polycations or polyanions to the vaccine formulation.

The immunogenic composition may be stable for is stable at room temperature (25° C.) for more than 1 week, in some embodiments for more than 2 weeks, in some embodiments for more than 3 weeks, in some embodiments for more than 4 weeks, in some embodiments for more than 5 weeks, and in some embodiments for more than 6 weeks. In some embodiments, the vaccine is stable for more than one month, more than 2 months, more than 3 months, more than 4 months, more than 5 months, more than 6 months, more than 7 months, more than 8 months, more than 9 months, more than 10 months, more than 11 months, or more than 12 months. In some embodiments, the vaccine is stable for more than 1 year, more than 2 years, more than years, or more than 5 years. In one embodiment, the immunogenic composition is stable under refrigeration (2-8° C.). Accordingly, in one embodiment, the immunogenic composition does not require frozen cold-chain. An immunogenic composition is stable if it retains its biological activity for a sufficient period to allow its intended use (e.g., to generate an immune response in a subject). For example, for immunogenic compositions that are to be stored, shipped, etc., it may be desired that the immunogenic compositions remain stable for months to years.

Method of Vaccination

Also provided herein is a method of treating, protecting against, and/or preventing disease in a subject in need thereof by administering the immunogenic composition to the subject. Administration of the immunogenic composition to the subject can induce or elicit an immune response in the subject. The induced immune response can be used to treat, prevent, and/or protect against disease, for example, one or more tumor associated pathologies.

The induced immune response can include an induced humoral immune response and/or an induced cellular immune response. The humoral immune response can be induced by about 1.5-fold to about 16-fold, about 2-fold to about 12-fold, or about 3-fold to about 10-fold. The induced humoral immune response can include IgG antibodies and/or neutralizing antibodies that are reactive to the antigen. The induced cellular immune response can include a CD8$^+$ T cell response, which is induced by about 2-fold to about 30-fold, about 3-fold to about 25-fold, or about 4-fold to about 20-fold.

The immunogenic composition dose can be between 1 μg to 10 mg active component/kg body weight/time, and can be 20 μg to 10 mg component/kg body weight/time. The immunogenic composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of immunogenic composition doses for effective treatment can be 1, 2, 3, 4, 5, 6, 7, 8, 9, or 10.

The immunogenic composition can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration.

The immunogenic composition can be administered prophylactically or therapeutically. In prophylactic administration, the immunogenic compositions can be administered in an amount sufficient to induce an immune response. In therapeutic applications, the immunogenic compositions are administered to a subject in need thereof in an amount sufficient to elicit a therapeutic effect. An amount adequate to accomplish this is defined as "therapeutically effective dose." Amounts effective for this use will depend on, e.g., the particular composition of the immunogenic composition regimen administered, the manner of administration, the stage and severity of the disease, the general state of health of the subject, and the judgment of the prescribing physician.

The immunogenic composition can be administered by methods well known in the art as described in Donnelly et al. (1997, Ann. Rev. Immunol. 15:617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the immunogenic composition can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The immunogenic composition can be delivered via a variety of routes. Typical delivery routes include parenteral administration, e.g., intradermal, intramuscular or subcutaneous delivery. Other routes include oral administration, intranasal, and intravaginal routes. For the DNA of the immunogenic composition in particular, the immunogenic composition can be delivered to the interstitial spaces of tissues of an individual (Feigner et al., U.S. Pat. Nos. 5,580,859 and 5,703,055, the contents of all of which are incorporated herein by reference in their entirety). The immunogenic composition can also be administered to muscle, or can be administered via intradermal or subcutaneous injections, or transdermally, such as by iontophoresis. Epidermal administration of the immunogenic composition can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The immunogenic composition can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the immunogenic composition.

The immunogenic composition can be a liquid preparation such as a suspension, syrup or elixir. The immunogenic composition can also be a preparation for parenteral, subcutaneous, intradermal, intramuscular or intravenous administration (e.g., injectable administration), such as a sterile suspension or emulsion.

The immunogenic composition can be incorporated into liposomes, microspheres or other polymer matrices (Feigner et al., U.S. Pat. No. 5,703,055; Gregoriadis, Liposome Technology, Vols. Ito III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The immunogenic composition can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the immunogenic composition described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the immunogenic composition into tissue without the use of a needle. The MID may inject the immunogenic composition as a small stream or jet with such force that the immunogenic composition pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520, 950; 7,171,264; 6,208,893; 6,009,347; 6,120,493; 7,245, 963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired immunogenic composition in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the immunogenic composition into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver immunogenic compositions to all types of tissues, particularly to skin and mucosa. In some embodiments, a needle-free injector may be used to propel a liquid that contains the immunogenic composition to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes.

A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle immunogenic composition injectors that deliver the immunogenic composition and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA® (electroporation device) (Inovio Pharmaceuticals, Blue Bell PA) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra® (electroporation device) device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described immunogenic composition herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so users have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

Method of Preparing Nucleic Acid Plasmids

Provided herein is methods for preparing the nucleic acid plasmids that comprise the nucleic acd based immunogenic compositions discussed herein. The nucleic acid plasmids, after the final subcloning step into the mammalian expression plasmid, can be used to inoculate a cell culture in a large scale fermentation tank, using known methods in the art.

The nucleic acid plasmids for use with the EP devices of the present invention can be formulated or manufactured using a combination of known devices and techniques. In some examples, the nucleic acid plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

Method of Treatment

The immunogenic composition can be used to generate or elicit an immune response in a mammal that is reactive or directed to FAP of a subject in need thereof. In one embodiment the immunogenic composition can be used to prevent or treat a cancer in the subject. In one embodiment, the cancer expresses FAP. Accordingly, the immunogenic composition can be used in a method that treats and/or prevents an FAP expressing cancer in the subject administered the immunogenic composition. In one embodiment, the immunogenic composition can be used to prevent a primary or initial occurrence of an FAP expressing cancer in a subject. In one embodiment, the immunogenic composition can be used to prevent recurrence of an FAP expressing cancer in a subject.

In some embodiments, the immune response can generate a humoral immune response and/or an antigen-specific cyto-toxic T lymphocyte (CTL) response that does not cause damage to or inflammation of various tissues or systems (e.g., brain or neurological system, etc.) in the subject administered the immunogenic composition.

In some embodiments, the administered immunogenic composition can increase survival of cancer, reduce tumor size, or a combination thereof in the subject. The administered immunogenic composition can increase survival of cancer by 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% or more in the subject. The administered immunogenic composition can reduce tumor size by 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% or more in the subject after immunization.

The administered immunogenic composition can increase a cellular immune response in the subject by about 5-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered immunogenic composition can increase the cellular immune response in the subject by about 5-fold, 10-fold, 20-fold, 30-fold, 40-fold, 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The administered vaccine can increase interferon gamma (IFN-γ) levels in the subject by about 5-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase IFN-γ levels in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The vaccine dose can be between 1 μg to 10 mg active component/kg body weight/time and can be 20 μg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

Routes of Administration

The immunogenic or pharmaceutical composition can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The immunogenic composition can be administered by traditional syringes, needleless injection devices, "microprojectile bombardment gene guns", or other physical methods such as electroporation ("EP"), "hydrodynamic method", or ultrasound.

The vector of the vaccine can be administering to the mammal by several well-known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The optimized consensus FAP antigen of the invention can be administered via DNA injection along with in vivo electroporation.

Kit

Provided herein is a kit, which can be used for treating a subject using the method of vaccination described above. The kit can comprise the immunogenic composition.

The kit can also comprise instructions for carrying out the vaccination method described above and/or how to use the kit. Instructions included in the kit can be affixed to packaging material or can be included as a package insert. While instructions are typically written or printed materials, they are not limited to such. Any medium capable of storing instructions and communicating them to an end user is contemplated by this disclosure. Such media include, but are not limited to, electronic storage media (e.g., magnetic discs, tapes, cartridges), optical media (e.g., CD ROM), and the like. As used herein, the term "instructions" can include the address of an internet site which provides instructions.

The present invention has multiple aspects, illustrated by the following non-limiting examples.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Synthetic Consensus FAP Immunogenic Composition

The FAP protein is a protease and gelatinase expressed on activated fibroblasts. FAP is expressed in >90% of cancer associated fibroblasts in human carcinomas, including in prostate cancer and pancreatic cancer. FAP is also expressed in fibroblasts associated with wound healing and malignant cells of bone and soft tissue sarcoma. Antibodies directed at FAP (e.g. sibrotuzumab) and small molecule inhibitors of FAP (e.g. talabostat) are safe, but show minimal efficacy in clinical trials.

In the past decade there has been a surge in interest in developing immune therapies targeting FAP-expressing cells (Fang et al., 2016, Mol Ther Oncolytics, 3:16007; Gottschalk et al., 2013, PLoS One, 8:e82658; Zhang and Ertl, 2016, Oncotarget, 7:23282-99; Xia et al., 2016, Cancer Immunol Immunother, 65:613-624; Wen et al., 2010, Cancer Sci, 101:2325-2332; Xia et al., 2016, 34:4526-4535; Chen et al., 2015, Sci Rep, 5:14421; Loeffler et al., 2006, J Clin Invest, 116:1955-1962). Here, a DNA vaccine targeting FAP has been developed that incorporates novel improvements to the DNA vaccine design strategy. An important recent improvement that is incorporated is the use of synthetic micro-consensus (μCon) sequences to help break tolerance. It was previously demonstrated for a different tumor associated antigen, Wilms tumor 1 (WT1), that a synthetic consensus vaccine sharing approximately 95% homology with native mouse WT1 was superior at breaking tolerance and generating anti-tumor immunity in C57Bl/6 mice (Walters et al., 2017, Mol Ther, 25:976-988). Here, this concept was extended using genetically diverse outbred mice to demonstrate that this consensus vaccine design for FAP is superior to the native mouse FAP vaccine sequence. While individual mice immunized with the native FAP vaccine did show responses and were able to break tolerance, the responses were more broad and higher overall in the μCon FAP immunized mouse group.

Importantly, the μCon FAP DNA vaccine that was developed synergized with both TERT and PSMA tumor-targeting vaccines in generating more robust anti-tumor immunity than each vaccine alone. The μCon FAP vaccine may alter the milieu of the tumor microenvironment to allow the PSMA vaccine to have a more robust anti-tumor effect (Yadav et al., 2014, Nature, 515:572-576).

This study demonstrates that FAP is a viable therapeutic vaccine target for cancer immunotherapy, and shows particular efficacy when used in combination with tumor antigen vaccine therapy. Other gene therapy approaches for targeting FAP, such as chimeric antigen receptor therapy, have some toxicity concerns (Wang et al., 2014, Cancer Immunol Res, 2:154-166). Thus, DNA based vaccine approaches may be a safer and more readily available alternative.

The Methods are Now Described.

DNA Plasmids

The synthetic micro-consensus (μCon) FAP sequence was generated by aligning over 20 FAP sequences from animals related to mouse and human, such as rat, macaque and hamster. These sequences were aligned using ClustalX2. Only the extracellular domain sequences (amino acids 26-761) were encoded in the plasmid and thus were used for the alignment (FIG. 1A). An additional mutation, S624A, was introduced to block the dipeptidyl peptidase and gelatinolytic activities of FAP. All sequences were RNA and codon optimized with a Kozak sequence at the N terminus, and an IgE leader sequence at the N terminus. All plasmids used were cloned into the modified pVax1 vector (GenScript). The final μCon mouse FAP sequence shares 95.1% sequence identity with native mouse FAP, calculated using Mega6.

Cell Culture and Transfection 293T cells (ATCC) and TC-1 cells (gift from Dr. Yvonne Paterson) were maintained in Dulbecco's Modified Eagle Medium (DMEM) supplemented with 10% fetal bovine serum (FBS). The TRAMP-C2 tumor cell line (ATCC) was maintained in DMEM (with Glutamax+4.5 g/L D-Glucose) supplemented with 5% FBS, 5% NuSerum IV, 10 nM dehydroisoandrosterone, and 0.005 mg/mL of bovine insulin. All cell lines were routinely tested for *Mycoplasma* contamination, and were maintained at a low passage (<20 passages for cell culture, <5 passages for implantation in mice). To confirm expression of FAP vaccine constructs, 293T cells were transfected with each plasmid using lipofectamine 3000 according to manufacturer's guidelines. Cell lysate was collected 48 hours after transfection. Cells were lysed with RIPA lysis buffer (Cell Signaling Technology) supplemented with EDTA-free protease inhibitor (Roche).

Animal Immunization

C57Bl/6, Balb/c and CD-1 outbred mice were purchased from Jackson Laboratory. Mice were immunized by injecting 30 μL of DNA (ug quantities of DNA are indicated in figure legends) into the tibialis interior (TA) muscle, followed by delivery of two 0.1 Amp electric constant current square-wave pulses using electroporation (EP) using the CELLECTRA®-3P electroporation device (Inovio Pharmaceuticals). The vaccine schedules used are indicated in each figure or figure legend.

Tumor Challenge Studies

For tumor challenge studies, 50,000 TC-1 cells or 1,000,000 TRAMP-C2 cells were implanted subcutaneously into the right flanks of female C57Bl/6 mice or male C57Bl/6 mice, respectively. One week (for TC-1 implantation) or four days (for TRAMP-C2 implantation) after implantation, mice were randomized into treatment groups. Mice were then immunized once weekly for a total of four immunizations. Tumors were monitored twice weekly, and measured using electronic calipers. Tumor volume was calculated using the formula:

$$Volume=(\pi/6)*(height)*(width2).$$

Mice were euthanized when tumor diameters exceeded 1.5 cm.

Splenocyte and Tumor Infiltrating Lymphocyte (TIL) Isolation

Spleens from immunized mice were harvested in RPMI medium supplemented with 10% FBS. Splenocytes were dissociated using a stomacher, filtered and Red Blood Cells were lysed using ACK Lysis Buffer (LifeTechnologies). Cells were filtered through a 40 μm filter, and counted and plated for staining or for ELISpots. Tumors were mechanically dissociated using a scalpel, and then incubated in a mixture of Collagenase I, II and IV (170 mg/L, ThermoFisher), DNAseI (12.5 mg/L, Roche), Elastase (25 mg/L, Worthington) in a 50/50 mixture of Hyclone L-15 Leibowitz medium (ThermoFisher) and RPMI+10% FBS+1% Penicillin/Streptomycin. Dissociated cells were then filtered twice through a 40 μm filter, and plated for stimulation and staining.

ELISpot Assay

ELISpot assays were performed using the MABTECH Mouse IFN-γ ELISpotPLUS plates. Briefly, 200,000 splenocytes were plated per well, and stimulated for 24 hours in the presence of peptides (15-mer peptides overlapping by 9 amino acids). Cells were stimulated with 5 μg/mL of each peptide in RPMI+10% FBS media. Spots were developed and quantified according to the manufacturer's instructions. Media alone and Concanavalin A stimulated cells were used as negative and positive controls, respectively. Spot forming units (SFU) per million cells was calculated by subtracting the media alone wells from the peptide stimulated wells. Spots were read using an ImmunoSpot CTL reader.

Intracellular Cytokine Staining and Flow Cytometry

Splenocytes or TILs were stimulated with native mouse FAP peptides for 5 hours with Protein Transport Inhibitor Cocktail (eBioscience). Cell stimulation cocktail (plus protein transport inhibitors) and complete media (R10) were used as positive and negative controls, respectively. During stimulation, cells were incubated with FITC α-mouse CD107a (clone 1D4B, Biolegend) to detect degranulation. After stimulation, cells were incubated with LIVE/DEAD violet to detect viability. Cells were then incubated with surface stain for 30 minutes at room temperature. Cells were then fixed and permeabilized using the FoxP3/transcription factor fixation/permeabilization kit (eBioscience). Cells were then incubated in intracellular stain for 1 hour at 4° C. A list of antibodies used is included in the Supplementary Methods. All samples were run on a 14- or 18-color LSRII flow cytometer (BD Bioscience), and analyzed using FlowJo software.

Flow Cytometry Staining Antibodies

The following antibodies were used in this study: PECy5 αCD3 (clone 145-2C11, BD Pharmingen), BV510 αCD4+ (clone RM4-5, Biolegend), BV605 αTNFα (clone MP6-XT22), PE αT-bet (clone 4B10, Biolegend), APC αFoxP3 (clone FJK-16s, eBioscience), APCCy7 αCD8+(clone 53-6.7, Biolegend), AF700 αCD44 (clone IM7, Biolegend), APC αIFNγ (clone XMG1.2, Biolegend), BV510 αCD11b (M1/70, Biolegend), BV605 αCD11c (N418, Biolegend), PE/Cy7 αCD68 (FA-11, Biolegend), AF700 αCD86 (GL-1, Biolegend), PE αArg1 (IC5868P, R&D), PE/Cy7 αCD86 (GL-1, Biolegend), PE/Cy7 αCD83 (Michel-19, Biolegend), BV650 αCD80 (16-10A1, Biolegend), APC αF4/80 (BM8, Biolegend), AF700 αF4/80 (BM8, Biolegend), PE αB220 (RA3-6B2, Biolegend), FITC αCD45 (30-F11, Biolegend), BV510 αNK1.1 (PK136, Biolegend), APC/Cy7 αMHCII (M5/114.15.2, Biolegend), and PE/Cy7 αCD25 (PC61.5, eBioscience).

Western Blot

Cell lysate was run on a 4-12% Bis-Tris NuPAGE gel (ThermoFisher Scientific) and subsequently transferred to a PVDF membrane (Millipore). The membrane was blocked with Odyssey Blocking Buffer for 1 hour at room temperature, and was incubated with primary antibody (Anti-FAP ABT11, Millipore, 1:1000 or Anti-Actin AC-15, Sigma, 1:10,000) overnight at 4° C. The membrane was washed with 0.1% Tween-20 in PBS, and incubated with 1:10,000 dilution of secondary antibodies IRDye 680RD goat anti-mouse and IRDye 800CW goat anti-rabbit (LiCor). The membrane was developed and analyzed using the LiCor Odyssey CLx Imaging System.

ELISA

Serum was collected from mice prior to sacrifice to determine antibody responses by enzyme-linked immunosorbent assay (ELISA). Maxisorp 96 well plates were coated with 1 μg/mL of mouse FAP protein (Separase recombinant protein, MyBiosource, 26-761 amino acid fragment) in PBS overnight at 4° C. Plates were blocked with 10% fetal calf serum (FCS) in PBS for 1 hour at room temperature. All washes were performed in 0.2% Tween-20 in PBS (PBST). For endpoint binding titers, a 1:50 dilution of serum was used in 1% FCS in PBST, followed by 4-four dilutions for the dilution curve. Anti-mouse IgG HRP (1:5000) was used as a secondary antibody for 1 hour at room temperature. Plates were developed for 10 minutes at room temperature using the Sigma Fast OPD tablets. The development was stopped using 1M H2SO4. Absorbance at 450 nm was read using a microplate reader.

Immunofluorescence/Immunohistochemistry Staining

For immunofluorescence or immunohistochemical staining, tissues were embedded and frozen in O.C.T. (Tissue-Tek) on dry ice and stored at −80° C., or fixed in 10% neutral-buffered formalin and subsequently paraffin-embedded. For hyaluronan staining, frozen tissues were sectioned onto PermaFrost slides, and then fixed in a mixture of 3.7% paraformaldehyde-PBS, 70% ethanol, 5% glacial acetic acid for 15 minutes at room temperature. Slides were then rinsed in PBS and blocked with 1% bovine serum albumin (BSA) in PBS for 30 minutes at room temperature. Biotinylated Hyaluronan Binding Protein (HABP, Millipore) was added to the blocker at a dilution of 1:1000 at 4° C. overnight. The slides were washed in PBS, and then Streptavidin AF488 conjugate was added in blocking solution at 1:500 for 1 hour in the dark at room temperature. Slides were washed with PBS and mounted with ProLong Gold Antifade with DAPI. For F4/80 and CD8+ staining, frozen sections were fixed in 4% paraformaldehyde-PBS for 15 minutes at room temperature. Slides were rinsed in PBS and permeabilized with 0.5% Triton™ X-100 for 15 minutes at room temperature. Slides were then blocked with 2.5% BSA and 5% goat serum in PBS for 1 hour, and then with the Avidin/Biotin Blocking Kit (Vector Labs). The primary F4/80 (F4/80-biotin, BM8 1:2000) and CD8+α (CD8+α-biotin, 53-6.7, 1:2000) antibodies were incubated in blocking buffer overnight at 4° C. After washing with PBS, slides were incubated with TSA-Biotin (PerkinElmer) for 8 minutes at room temperature for signal amplification, and then with Streptavidin AF488 (1:500) for 30 minutes at room temperature. Slides were subsequently washed and mounted with ProLong Gold Antifade with DAPI. For FAP staining, paraffin embedded tissues were sectioned onto PermaFrost slides. Sections were deparaffinized, rehydrated and incubated with primary antibody (FAP-biotin, R&D BAF3715, 1:40) overnight at 4° C. Slides were then incubated with secondary antibody (Streptavidin-HRP, 1:1000) for 1 hour at room temperature, and counterstained with hematoxylin. Staining of paraffin-embedded tissues was performed by the University of Pennsylvania Cancer Histology Core.

All slides were imaged using either a Zeiss™ LSM Confocal microscope (immunofluorescence images, University of Pennsylvania Cell and Developmental Biology Microscopy Core) or a Nikon 80i upright microscope for bright field images. At least 5 images were taken per tumor sample for quantification. Image analysis was performed using the Fiji/ImageJ software.

Statistical Analysis

For animal experiments, error bars represent the mean±standard error of the mean (SEM). For experiments with more than two experimental groups, statistical significance was determined by one- or two-way ANOVA, followed by Tukey's post-hoc HSD test. For animal experiments with only two groups, significance was determined using a two-tailed student's t-test. For mouse tumor survival studies, significance was determined by Gehan-Breslow-Wilcoxon test.

The Results are Now Described

Design and In Vitro Expression of Micro-Consensus (μCon) FAP DNA Vaccine

FAP is a membrane-bound enzyme with a large extracellular domain and a small cytoplasmic tail and transmembrane domain. For the vaccine design, a plasmid was constructed that contains only the extracellular domain of FAP (amino acids 26-761) fused to an immunoglobulin E (IgE) leader sequence at the N terminus for efficiency of protein production and to facilitate secretion (FIG. 1B). To facilitate breaking tolerance to the native mouse FAP (mFAP) sequence, a micro-consensus (μCon) sequence was designed using sequence alignment from various related species in the NCBI database, which provides some sequence diversity, but conserves structure. This μCon sequence shares 95.1% homology to the native protein sequence (FIG. 1A). Further, the optimized consensus FAP contains a S624A substitution in the catalytic domain to block to block both dipeptidyl peptidase and gelatinolytic activities of the soluble FAP enzyme (FIG. 1B and FIG. 1C). Similarly a mFAP plasmid was generated for comparison purposes which shares 100% homology to the mFAP sequence, and otherwise contains the same sequence optimizations, including addition of an IgE leader sequence and RNA/codon optimization. Expression of both the native and μCon FAP plasmids was detected in vitro in the lysates of transfected 293T cells (FIG. 1D).

Immunogenicity of μCon FAP DNA Vaccine in C57Bl/6 Mice

Figures 2A, 2B, 2C, 2D, 2E:
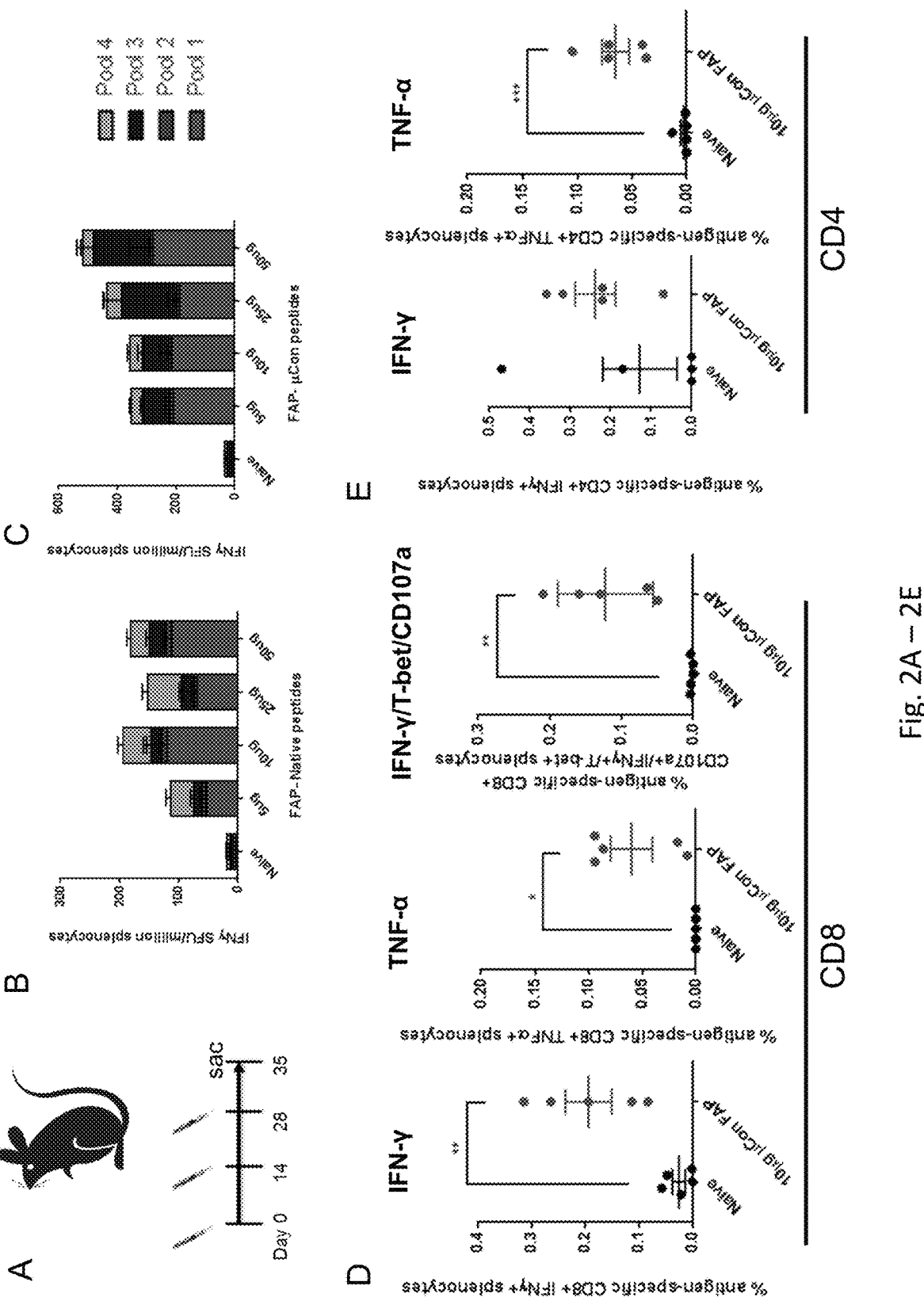
FIG. 2A through FIG. 2E, depicts experimental results demonstrating the immunogenicity of μCon mouse FAP vaccine in C57Bl/6 mice.

In order to determine whether the μCon FAP DNA vaccine was immunogenic and capable of breaking tolerance in mice, C57Bl/6 mice were immunized with different doses of μCon FAP DNA vaccine (5 μg, 10 μg, 25 μg and 50 μg) by intramuscular injection with EP (FIG. 2A). Mice were immunized three times at two week intervals, and splenocytes were harvested for analysis one week after final immunization (FIG. 2A). Interferon α (IFN-γ) ELISpots were performed using peptides exactly matched to the vaccine sequence (μCon peptides), or peptides matched to the mFAP sequence (native peptides). C57Bl/6 mice generated robust IFN-γ ELISpots to both native FAP and μCon FAP peptides, indicating that the μCon FAP vaccine is capable of breaking tolerance in mice (FIG. 2B and FIG. 2C). There was a dose-dependent effect of the vaccine against μCon peptides; however, the dose-dependence for the native peptides reached maximum responses at the 10 μg dose (FIG. 2B and FIG. 2C). Therefore, a 10 μg dose was used for the remaining experiments, and only responses to mFAP peptides (which match mouse FAP 100%) are shown.

To further evaluate the CD8+ and CD4+ cytokine responses generated against native FAP peptides, intracellular cytokine staining was performed on stimulated splenocytes (FIG. 2D and FIG. 2E). A significant increase in observed in IFN-γ and TNF-α production in CD8+ T cells in μCon FAP immunized mice compared to naïve control mice (FIG. 2D). Next the cytolytic potential of the CD8+ T cells generated by the μCon FAP vaccine was evaluated using the degranulation marker CD107a and the transcription factor T-bet, which is expressed in activated T cells (FIG. 2D). A significant increase in CD8+ T cells that were simultaneously positive for IFN-γ, CD107a and T-bet in μCon FAP vaccinated mice was seen as compared to naïve control mice, indicating that this vaccine induces production of effector T cells with cytolytic killing potential (FIG. 2D). A significant increase in TNF-α production in CD4+ T cells was also observed in μCon FAP immunized mice compared to naïve control mice (FIG. 2E). There was a trend towards increased IFN-γ production in CD4+ T cells as well; however, this trend was not statistically significant (FIG. 2E).

Figures 3A, 3B, 3C:
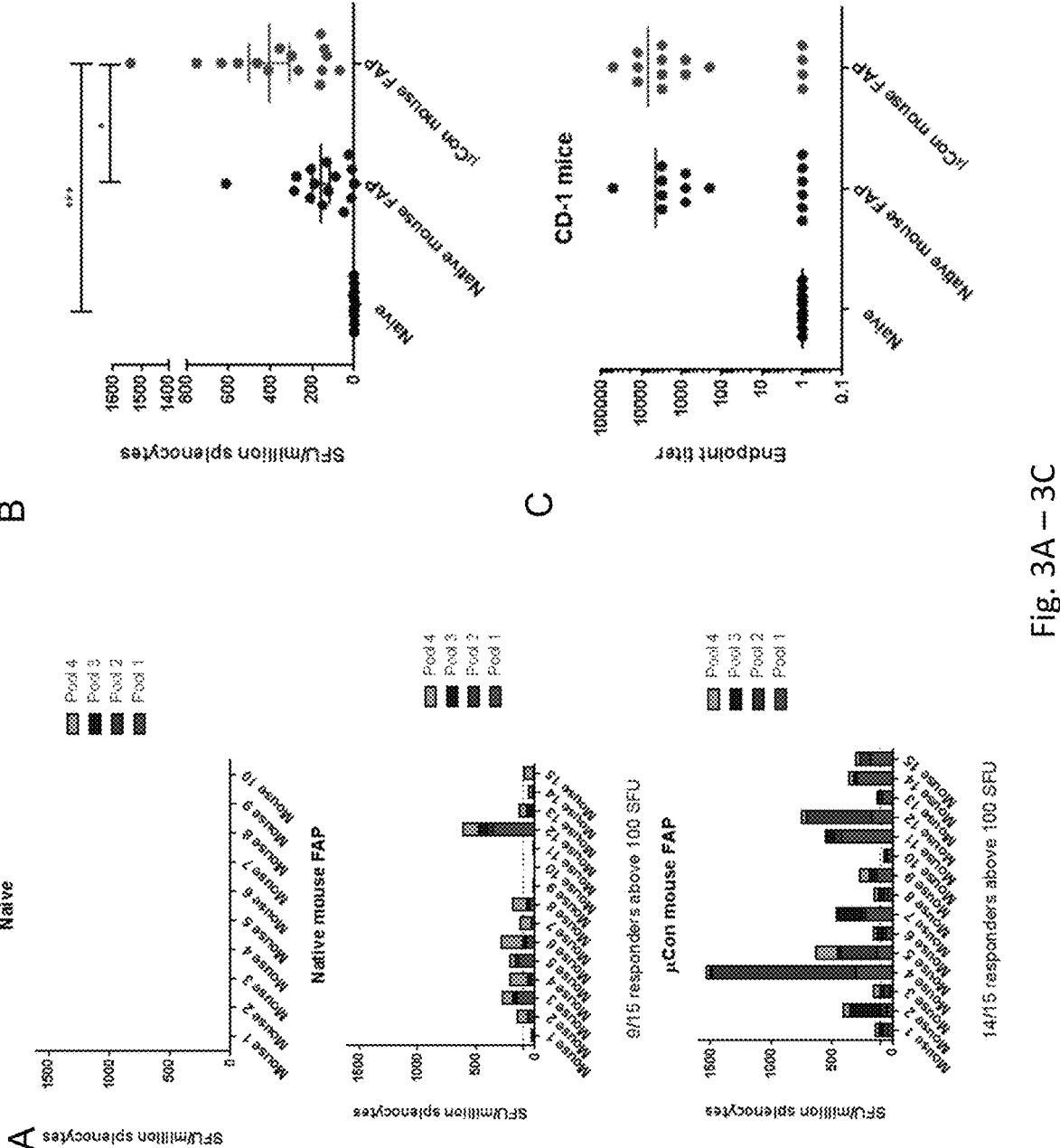
FIG. 3A through FIG. 3C, depicts experimental results demonstrating a comparison of native and μCon FAP vaccines in CD-1 outbred mice.

Micro-Consensus DNA Vaccine Design is Superior to the Native FAP DNA in Breaking Tolerance and Generating a CD8+ T Cell Response in a Genetically Diverse Population of Mice The capacity of the μCon FAP DNA vaccine to generate immune responses in outbred mice (CD-1 ICR "Swiss" mice) was evaluated in comparison to a mFAP DNA vaccine (FIG. 3). These genetically diverse mice were used as an important indication of immune potency in a more relevant tolerance model for extrapolation to outbred populations such as humans. Mice were immunized with 10 μg of mFAP DNA vaccine or μCon FAP DNA vaccine according to the schedule in FIG. 2A, and evaluated immune responses by IFN-γ ELISpot (FIG. 3A). While variability was observed between the mice, due to the outbred nature of these mice, the overall immune response was higher for the μCon FAP immunized group compared to the native FAP immunized group (FIG. 3A and FIG. 3B). Overall, 14/15 mice in the μCon FAP group, compared to 9/15 mice in the native FAP group, generated an immune response above 100 SFU/ million splenocytes (FIG. 3A). Responses observed in outbred mice (average of 407 SFU) were more diverse and higher than those observed in C57Bl/6 mice (average 195 SFU) (FIG. 2B, FIG. 3B).

The antibody responses were also evaluated in these mice using mFAP protein corresponding to the extracellular domain (amino acids 26-761) by ELISA (FIG. 3C). Interestingly the majority of the mice immunized with either native FAP vaccine or μCon FAP vaccine generated robust antibody responses (FIG. 3C). The percentage of mice in the μCon FAP group that generated antibody responses was higher compared to the native FAP group (11/15 mice compared to 9/15 mice). However, the difference was not statistically significant.

Micro-Consensus FAP DNA Vaccine Comparison to Native FAP DNA Vaccine in C57Bl/6 and Balb/c Mice Next, the difference in immune responses generated from the μCon FAP vaccine was compared to the native FAP vaccine in the commonly used mouse strains C57Bl/6 and Balb/c mice. The same comparison in these mice, with the same immunization schedule and vaccine dose was performed (FIG. 4A, 5A).

Figures 4A, 4B, 4C, 4D, 4E:
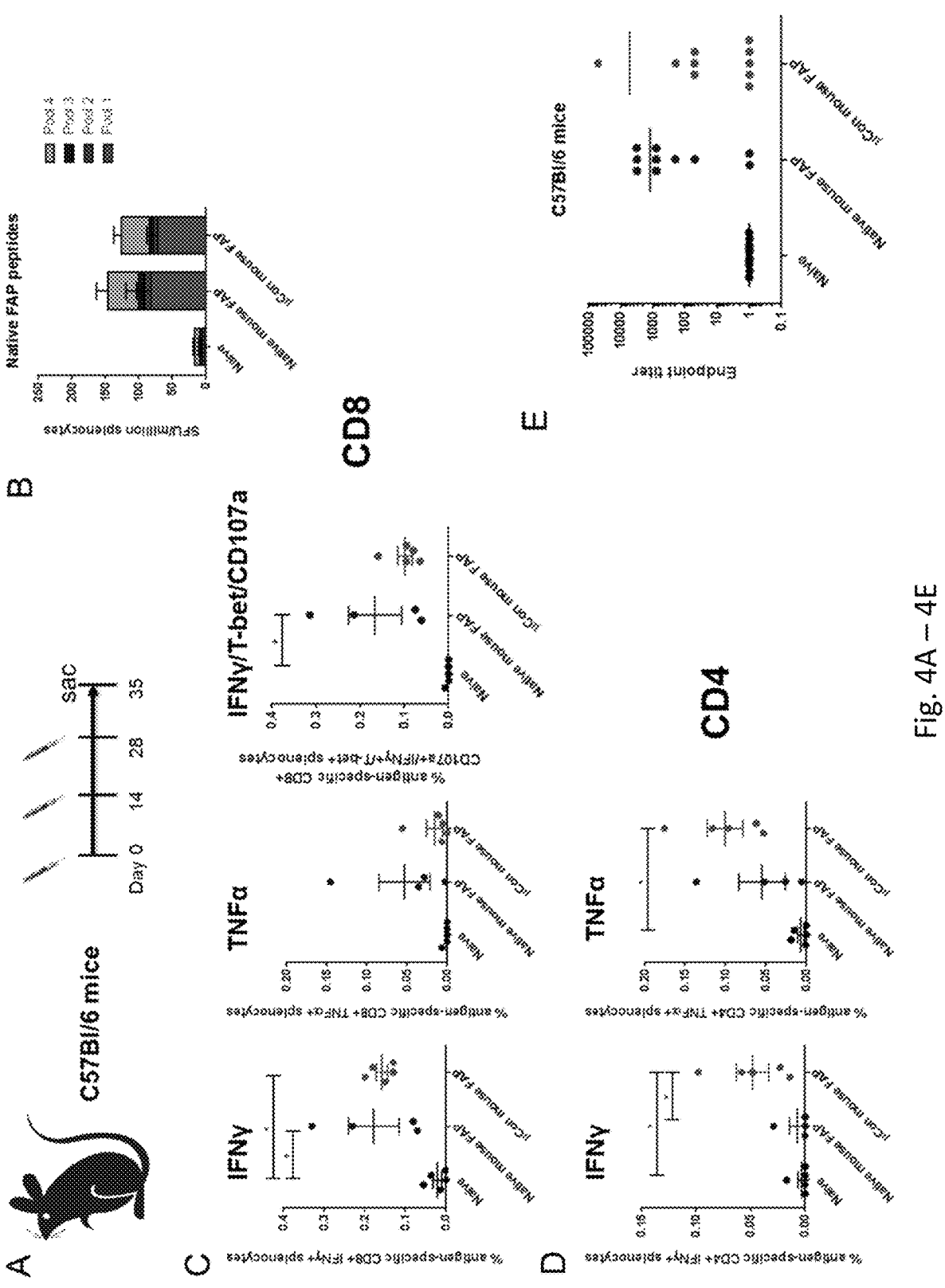
FIG. 4A through FIG. 4E, depicts experimental results demonstrating a comparison of native and μCon FAP vaccines in C57Bl/6 mice.

In the C57Bl/6 strain, which tend to generate better Th1 responses over Th2 responses, it was found that the μCon FAP vaccine generated a similar IFN-γ ELISpot response compared to the native FAP vaccine (FIG. 4B). These mice generated similar IFN-γ, TNF-α and IFN-γ/T-bet/CD107a triple-positive CD8+ T cell responses to both native and μCon FAP vaccines (FIG. 4C). However, the C57Bl/6 mice generated improved IFN-γ and TNF-α CD4+ T cell responses to the μCon vaccine compared to the native vaccine (FIG. 4D). In C57Bl/6 mice, the μCon FAP vaccine did not improve antibody responses compared to native FAP vaccine (FIG. 4E). In fact, native FAP trended towards better antibody responses; however, this trend was not statistically significant.

Figures 5A, 5B, 5C, 5D, 5E:
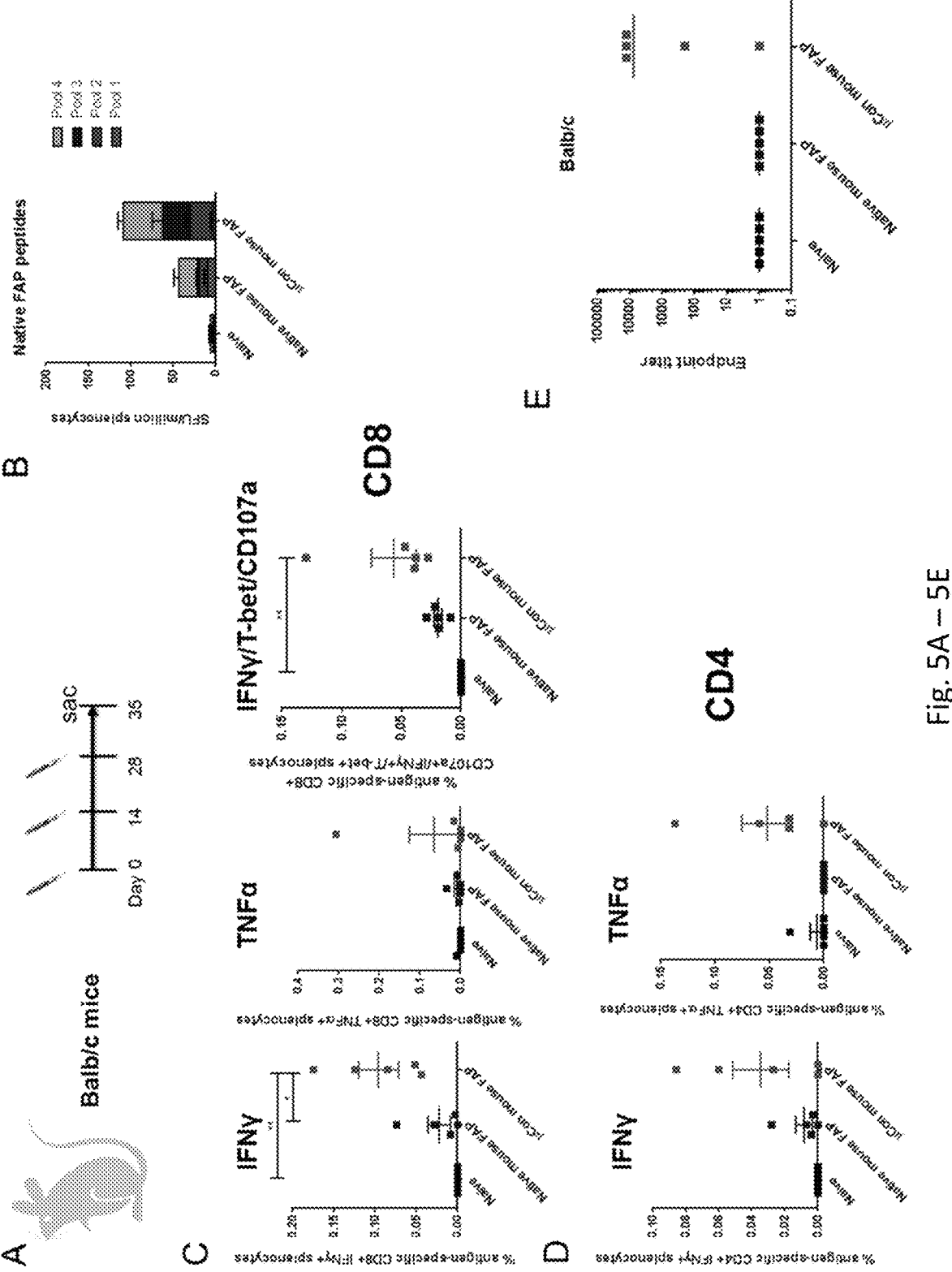
FIG. 5A through FIG. 5E, depicts experimental results demonstrating a comparison of native and μCon FAP vaccines in Balb/c mice.

In the Balb/c strain, which tend to generate better Th2 responses over Th1 responses, the μCon FAP vaccine generated superior IFN-γ ELISpot responses compared to the native FAP vaccine (FIG. 5B). Balb/c mice generated better IFN-γ and TNF-α responses in both CD8+ and CD4+ T cells (however, this was only statistically significant for IFN-γ production in CD8+ T cells) (FIG. 5C and FIG. 5D). In addition, Balb/c mice generated more robust IFN-γ/T-bet/CD107a triple-positive CD8+ T cells upon immunization with μCon FAP DNA vaccine compared to native FAP DNA vaccine (FIG. 5C). Strikingly, in Balb/c mice the native FAP vaccine did not generate any detectable antibody titers, while the μCon FAP vaccine generated robust antibody levels in 4/5 mice (FIG. 5E).

These results indicate that the commonly used strains of mice may skew the results of immune based studies, and that use of a genetically diverse population will be important for clinical application of an immune therapy. Overall, the μCon vaccine showed improvements in some immune aspect of breaking tolerance to native FAP antigen compared to the native FAP vaccine, both in the more immune tolerant Balb/c model and the immune responsive C57Bl/6 model.

Micro-Consensus FAP DNA Vaccine Synergizes with Tumor Antigen DNA Vaccines in Multiple Tumor Models

Figure 6B:
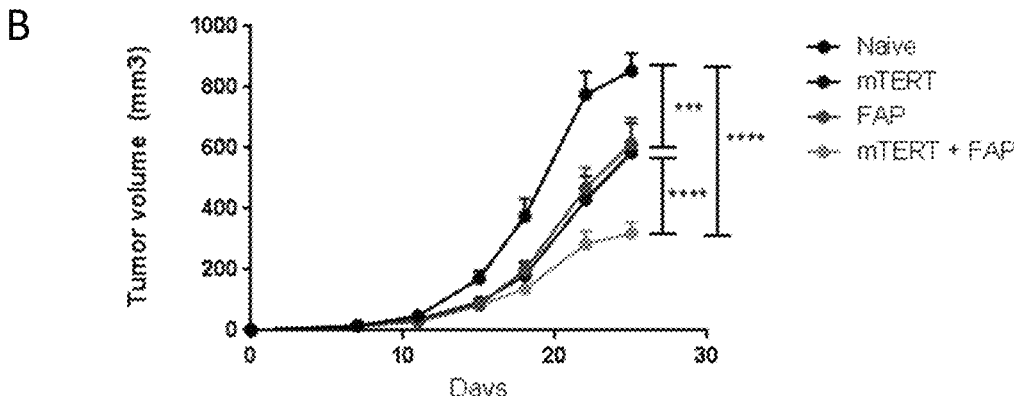
Figure 6C:
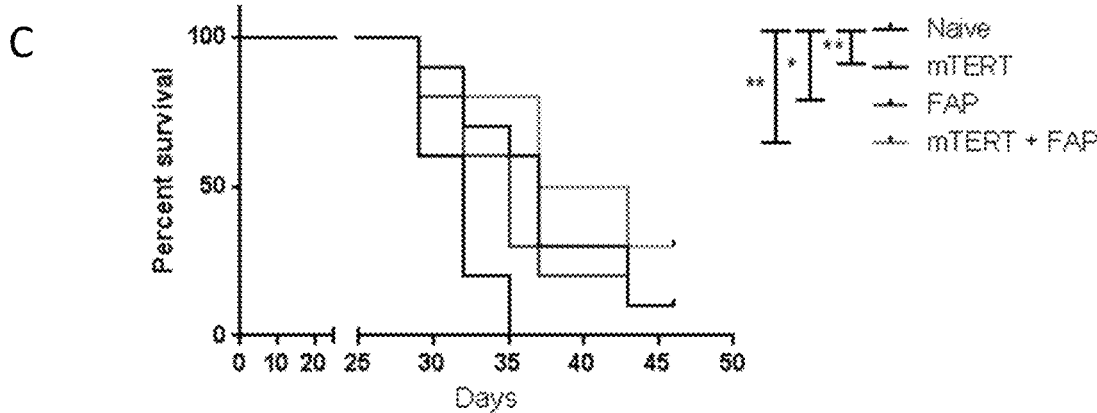
Figure 7A:
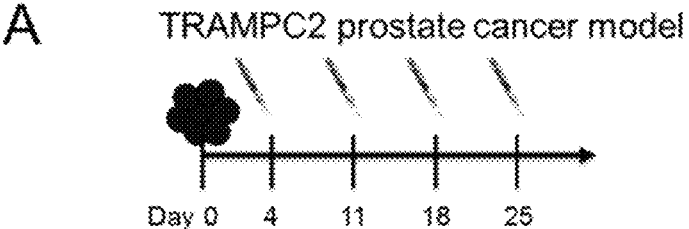
FIG. 7A through FIG. 7C, depicts exemplary experimental results demonstrating the efficacy of FAP vaccine and combination therapy in therapeutic prostate tumor model.
Figure 7B:
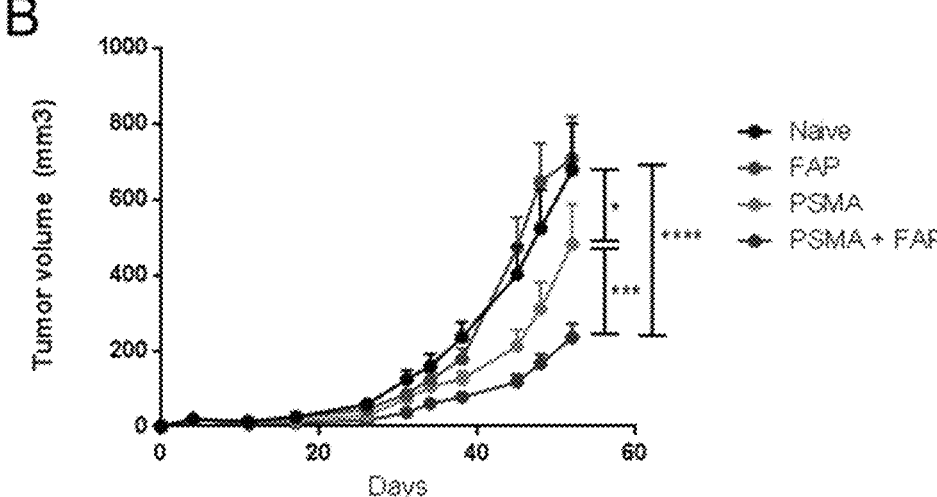
Figure 7C:
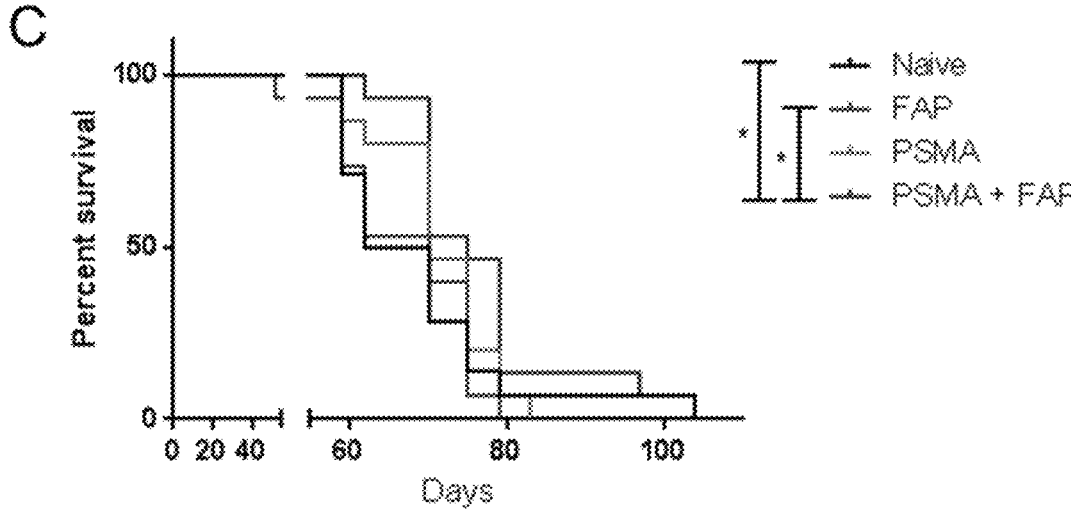

After establishing that robust IFN-γ and TNF-α immune responses are generated with increased frequency against native antigen for the μCon FAP DNA vaccine, the therapeutic efficacy of μCon FAP was evaluated in conjunction with a tumor associated antigen vaccine in a tumor challenge models. Combination therapies were tested with two vaccines that have been previously studied that target the tumor antigens PSMA or TERT (FIG. 6, FIG. 7) (Yan et al., 2013, Cancer Immunol Res, 1:179-189; Ferraro et al., 2011, 7 Suppl:120-7). Female C57Bl/6 mice were implanted with the lung tumor cell line TC-1 (FIG. 6A), and began immunizations on day 7 after tumor implantation. Mice were either immunized with μCon FAP DNA vaccine alone, mTERT (mouse TERT) vaccine alone, or a combination of μCon FAP and mTERT tumor antigen vaccine, injected into the same leg. Mice were immunized once weekly for a total of four immunizations. For the TC-1 tumor model, the combination of FAP and mTERT generated the most robust anti-tumor activity and improvement in mouse survival compared to either vaccine alone (FIG. 6B and FIG. 6C). To verify these results in a different tumor model, a similar experiment was performed using the μCon FAP vaccine in combination with a PSMA vaccine in the TRAMPC2 prostate tumor model (FIG. 7). Male C57Bl/6 mice were implanted with TRAMPC2 tumor cells, and began immunizations on day 4 after tumor implantation (FIG. 7A). For the TRAMPC2 tumor model, μCon FAP DNA vaccine alone had no impact on tumor growth, while the PSMA vaccine alone decreased tumor volume (FIG. 7B). However, the combination of PSMA and FAP decreased tumor volume and improved tumor survival more than the PSMA vaccine alone, indicating synergy between the two vaccines (FIG. 7B FIG. 7C).

Figure 8:
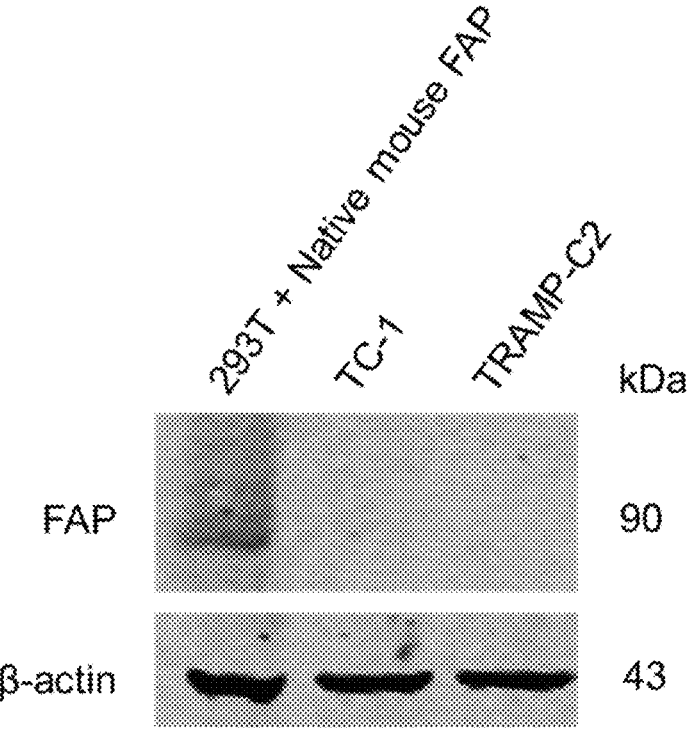
FIG. 8 depicts exemplary experimental results demon-strating the expression of FAP in tumor cell lines. Western blot expression of mouse FAP in the mouse tumor cell lines TC-1 and TRAMP-C2. 293T cells transfected with native mouse FAP plasmid were used as a positive control.

It was confirmed that the μCon FAP vaccine would only target cancer-associated fibroblasts by probing for expression of FAP in both the TC-1 and TRAMP-C2 cell lines (FIG. 8), two cell lines that do not express FAP.

Micro-Consensus FAP DNA Vaccine Induces FAP-Specific Tumor Infiltrating Lymphocytes

Figures 9A, 9B, 9C, 9D:
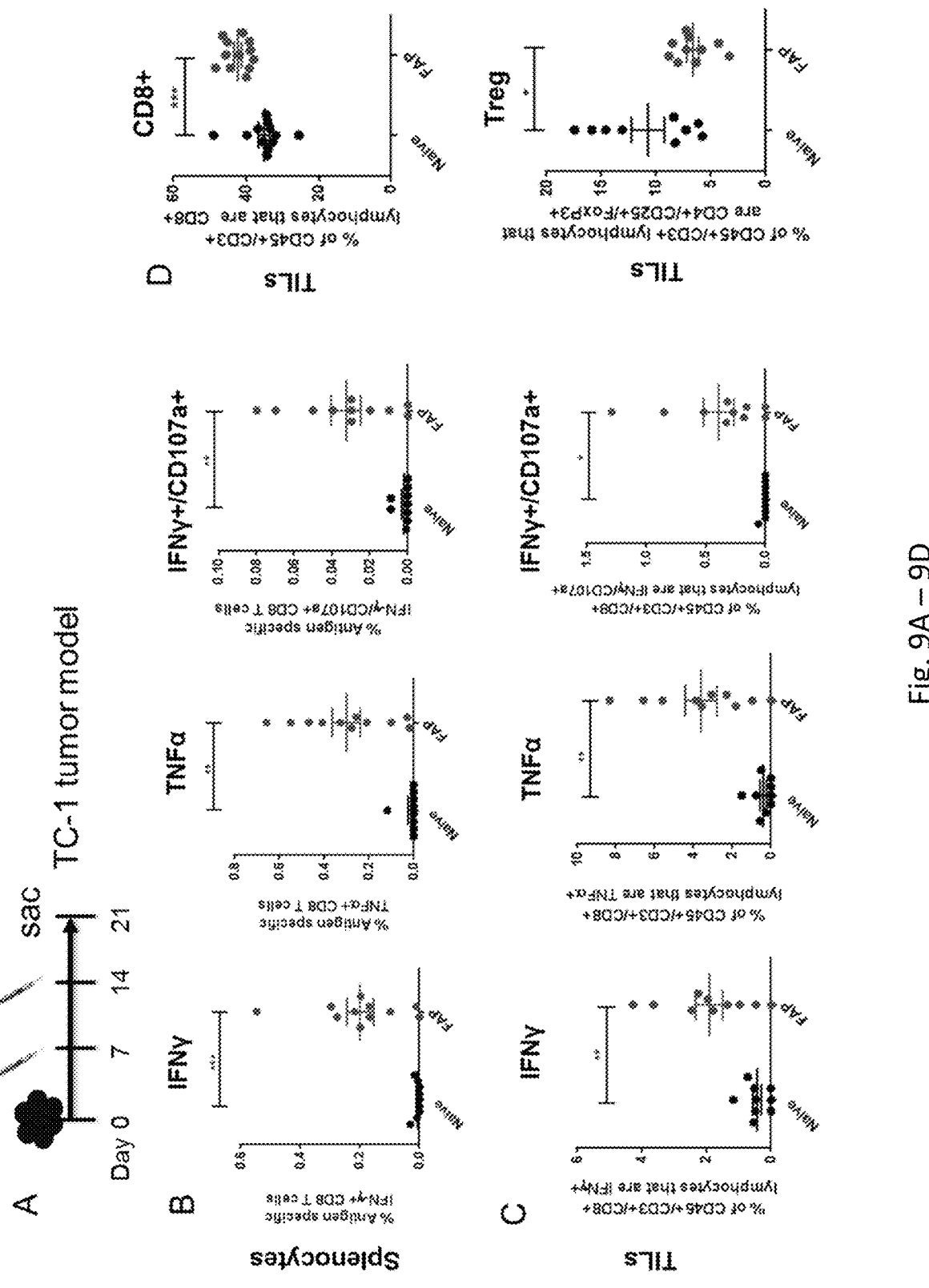
FIG. 9A through FIG. 9D, depicts exemplary experimental results demonstrating that the FAP vaccine induces FAP-specific TILs.
Figures 10A, 10B, 10C, 10D:
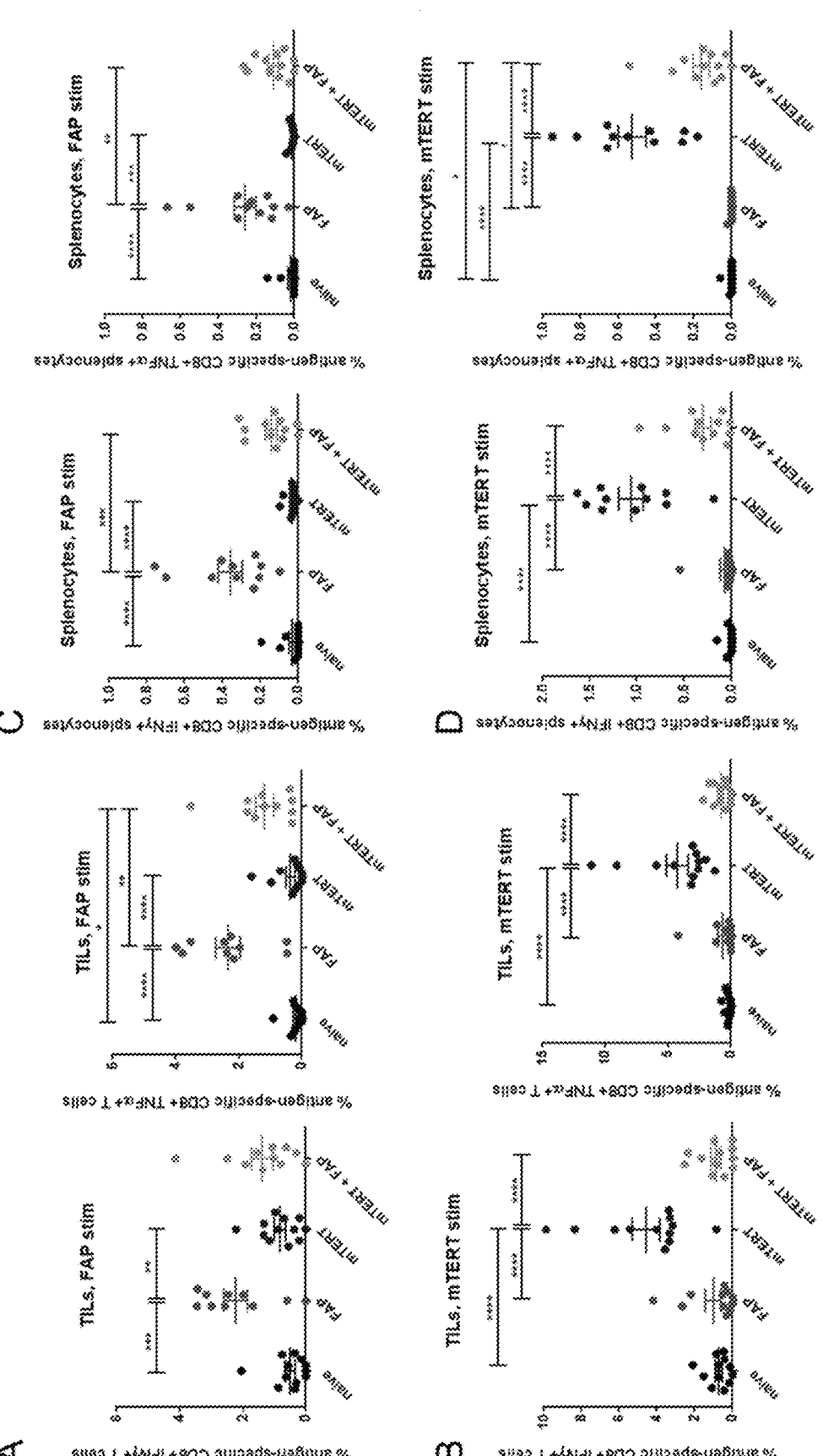
FIG. 10A through FIG. 10D, depicts exemplary experimental results demonstrating the immune responses from mice receiving combination mTERT+FAP vaccination. Mice were implanted with TC-1 tumor cells on day 0, randomized on day 7 and immunized once weekly for a total of 2 immunizations. 10 μg of μCon FAP DNA or 25 μg of mTERT DNA was used. Mice were sacrificed on day 21, and splenocytes and TILs were harvested.

Immune responses systemically and in the tumors of FAP-immunized tumor bearing mice. Mice were implanted with TC-1 tumors, and began immunizations 7 days after tumor implant (FIG. 9A). The mice were immunized twice at a one-week interval, and then sacrificed the mice one week after the final immunization (on day 21). The antigen-specific immune responses were evaluated in both splenocytes and in tumor-infiltrating lymphocytes from these mice. Despite giving the mice fewer immunizations over a shorter period of time, the mice exhibited superior CD8+IFN-γ and TNF-α production, as well as robust co-expression of CD107a and IFN-γ (FIG. 9B). Furthermore, a robust FAP-specific T cell response was observed in tumor infiltrating lymphocytes as well, with a significant increase in IFN-γ, TNF-α and IFN-γ/CD107a co-production in CD8+ T cells within the tumor (FIG. 9C). Furthermore, when the relative proportion of CD8+ T cells and regulatory T cells (CD3+/CD4+/CD25+/FoxP3+ cells) was examined an increase in CD8+ T cells and a decrease in Tregs was observed upon FAP immunization (FIG. 9D).

Immune responses were compared in TC-1 tumor bearing mice receiving treatment with FAP vaccine alone, mTERT vaccine alone, or the combination therapy (FIG. 10A through FIG. 10D). As expected, mice receiving either FAP vaccine alone or mTERT vaccine alone induce robust CD8+ IFN-γ and TNF-α responses in both the spleen and tumor to FAP peptides or mTERT peptides, respectively (FIG. 10A through FIG. 10D). Interestingly, in mice receiving combination therapy with mTERT and FAP simultaneously, the responses were diminished compared to mice receiving each vaccine alone, suggesting antigen interference (FIG. 10A through FIG. 10D). Despite this antigen interference, there was still improvement in anti-tumor responses in the combination therapy group compared to each vaccine alone, suggesting that dual-targeting of fibroblasts and tumor cells is an important strategy for cancer immune therapy.

Synthetic Consensus FAP DNA Vaccine Alters the Immune Microenvironment of TC-1 Tumors, Increasing the Proportion of CD8+ T Cells and Reducing the Proportion of Macrophages in the Tumor

Figures 11A, 11B, 11C, 11D, 11E, 11F, 11G, 11H:
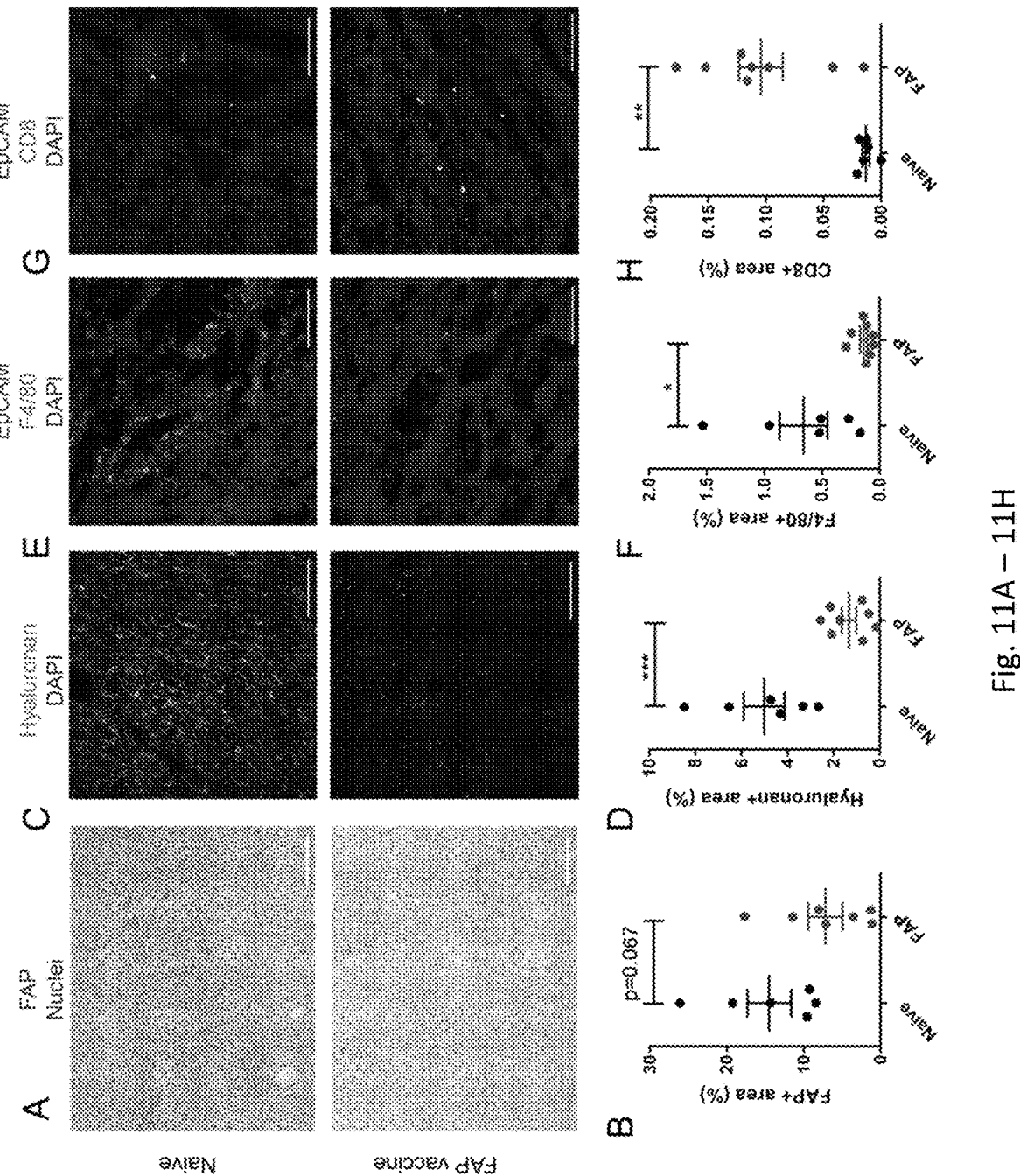
FIG. 11A through FIG. 11H, depicts exemplary experimental results demonstrating that the FAP vaccine alters the tumor microenvironment.
Figure 12A:
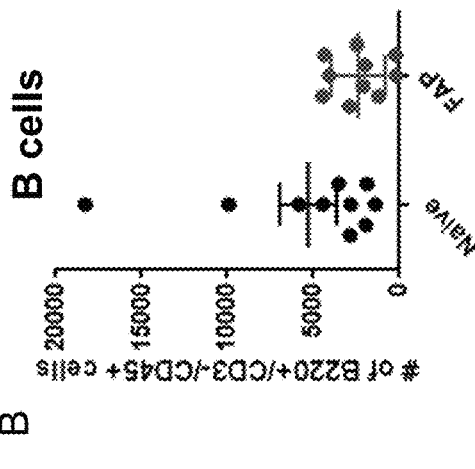
FIG. 12A through FIG. 12D, depicts exemplary experimental results demonstrating the impact of μCon FAP vaccine on immune cell subsets by flow cytometry. Mice were implanted with TC-1 tumor cells and immunized according to the schedule in FIG. 9A. Tumors were harvested for surface staining of innate immune cell populations, according to the markers indicated in figure legend.
Figure 12B:
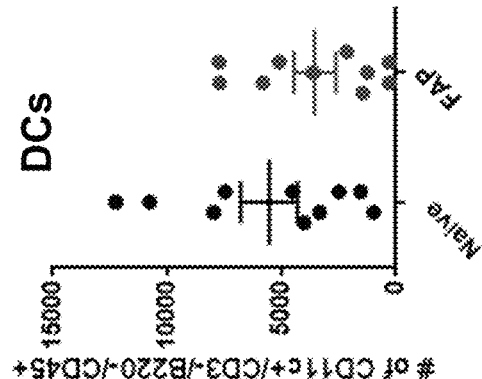
Figure 12C:
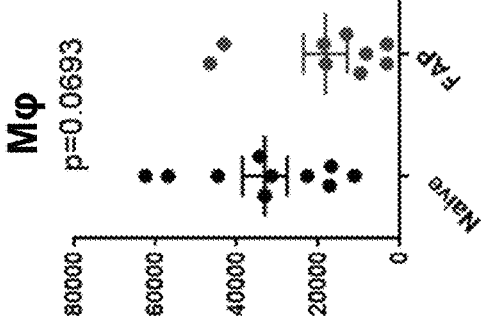
Figure 12D:
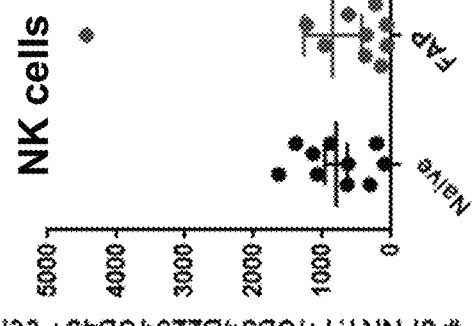

Other studies have reported alterations in the immune microenvironment upon immunization with vector-based, cell-based or DNA vaccines (Zhang and Ertl, 2016, Oncotarget, 7:23282-99; Xia et al., 2016, Cancer Immunol Innmother, 65:613-624; Chen et al., 2015, Sci Rep, 5:14421). Therefore, the tumor microenvironment of TC-1 tumors was evaluated upon immunization with μCon FAP using both immunohistochemical approaches as well as flow cytometry (FIG. 11, FIG. 12). A decrease in the area of tumor sections covered by FAP-expressing cells and the amount of hyaluronan, an extracellular matrix glycosaminoglycan secreted by both fibroblasts and tumor cells, was observed upon vaccination with μCon FAP DNA (FIG. 11A through FIG. 11D). A decrease in F4/80+ macrophage infiltration and an increase in CD8+ T cell infiltration was also observed upon FAP vaccination (FIG. 11E through FIG. 11H). A decrease in the frequency of F4/80+/CD11b+ macrophages per tumor was also observed upon FAP vaccination by flow cytometry, but no change in the frequency of B cells, NK cells or dendritic cells was observed upon FAP vaccination (FIG. 12A through FIG. 12D). In order to distinguish between the relative proportions of M1 polarized and M2 polarized macrophages upon FAP vaccination, surface marker expression was examined on the tumor infiltrating macrophages, including examination of expression of Arg1, MHCII, CD68, CD80 and CD86. No differences in marker expression was observed on these infiltrating macrophages, suggesting that there was no skewing in macrophage polarization upon vaccination with μCon FAP vaccine (FIG. 13A through FIG. 13E).

Example 2: Immunogenic Fragments of FAP

Figures 14A, 14B, 14C:
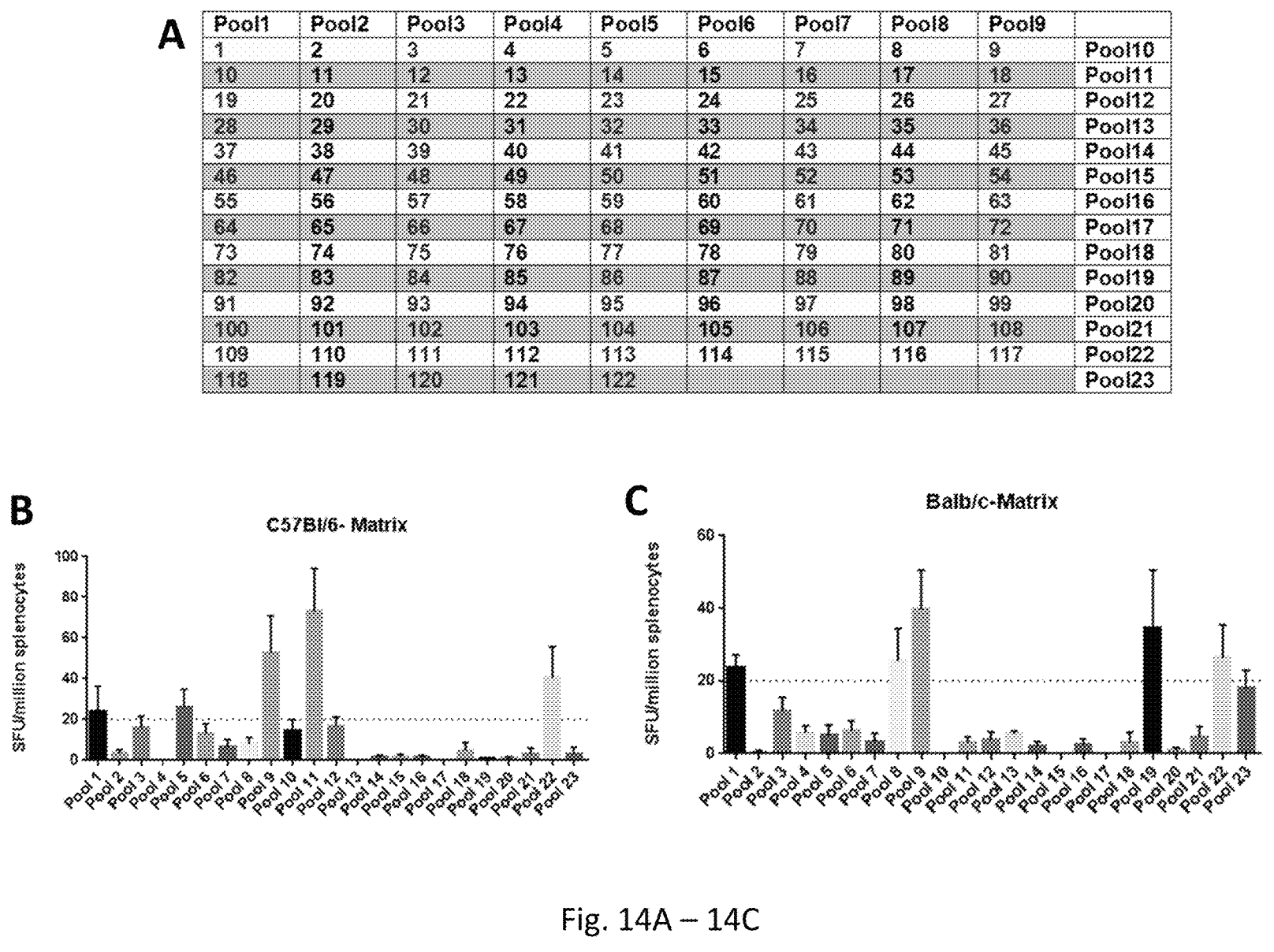

To characterize the responses that the mouse strains were having to native FAP peptides and to determine the dominant epitopes, 122 peptides representing different epitopes of FAP were generated for the optimized consensus FAP (FIG. 14A). When cells were stimulated with each pool, there was a large variety of responses (FIG. 14B and FIG. 14C), leading to the conclusion that there is not one dominant epitope, but rather multiple sub-dominant epitopes (FIG. 15). Several of the sub-dominant epitopes (e.g. SEQ ID NO: 22, SEQ ID NO: 23 and SEQ ID NO: 24) comprise mutations in the optimized consensus FAP with respect to the native FAP (FIG. 15).

Example 3: Sequence Information

| SEQ ID NO | Sequence Type | Description |
|---|---|---|
| 1 | nucleotide | synthetic consensus human FAP |
| 2 | amino acid | synthetic consensus human FAP |
| 3 | nucleotide | synthetic consensus human FAP operably linked to sequence encoding an IgE leader |
| 4 | amino acid | synthetic consensus human FAP operably linked to an IgE leader |
| 5 | nucleotide | synthetic consensus mouse FAP |
| 6 | amino acid | synthetic consensus mouse FAP |

-continued

| SEQ ID NO | Sequence Type | Description |
|---|---|---|
| 7 | nucleotide | synthetic consensus mouse FAP operably linked to sequence encoding an IgE leader |
| 8 | amino acid | synthetic consensus mouse FAP operably linked to an IgE leader |
| 9 | nucleotide | native mouse FAP |
| 10 | amino acid | native mouse FAP |
| 11 | nucleotide | native mouse FAP operably linked to an IgE leader sequence |
| 12 | amino acid | native mouse FAP operably linked to an IgE leader sequence |
| 13 | amino acid | immunodominant epitope of FAP |
| 14 | amino acid | immunodominant epitope of FAP |
| 15 | amino acid | immunodominant epitope of FAP |
| 16 | amino acid | immunodominant epitope of FAP |
| 17 | amino acid | immunodominant epitope of FAP |
| 18 | amino acid | immunodominant epitope of FAP |
| 19 | amino acid | immunodominant epitope of FAP |
| 20 | amino acid | immunodominant epitope of FAP |
| 21 | amino acid | immunodominant epitope of FAP |
| 22 | amino acid | immunodominant epitope of FAP |
| 23 | amino acid | immunodominant epitope of FAP |
| 24 | amino acid | immunodominant epitope of FAP |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. An isolated nucleic acid molecule encoding a single polypeptide, wherein the single polypeptide comprises the amino acid sequence of SEQ ID NO:4.

2. The nucleic acid molecule of claim 1, wherein the nucleic acid molecule is selected from the group consisting of a DNA molecule and an RNA molecule.

3. The nucleic acid molecule of claim 1, wherein the nucleic acid encoding the single polypeptide comprises a nucleic acid sequence encoding the amino acid sequence of SEQ ID NO: 4 comprises a nucleotide sequence comprising SEQ ID NO: 3.

4. The nucleic acid molecule of claim 1, wherein the encoded polypeptide is operably linked to at least one regulatory sequence selected from the group consisting of a start codon, an IgE leader sequence and a stop codon.

5. An isolated expression vector comprising the nucleic acid molecule of claim 1.

6. An isolated viral particle comprising the nucleic acid molecule of claim 1.

7. An isolated peptide consisting of the amino acid sequence of SEQ ID NO:4.

8. An immunogenic composition consisting of a peptide of claim 7 and a pharmaceutically acceptable excipient.

9. An immunogenic composition comprising a nucleic acid molecule of claim 1.

* * * * *